United States Patent
Tsuyama et al.

(10) Patent No.: US 10,651,400 B2
(45) Date of Patent: May 12, 2020

(54) ORGANIC SEMICONDUCTOR ELEMENT, MANUFACTURING METHOD THEREOF, COMPOSITION FOR FORMING ORGANIC SEMICONDUCTOR FILM, AND METHOD OF MANUFACTURING ORGANIC SEMICONDUCTOR FILM

(71) Applicants: FUJIFILM CORPORATION, Minato-ku, Tokyo (JP); THE UNIVERSITY OF TOKYO, Bunkyo-ku, Tokyo (JP)

(72) Inventors: Hiroaki Tsuyama, Kanagawa (JP); Yoshihisa Usami, Kanagawa (JP); Toshihiro Okamoto, Tokyo (JP); Junichi Takeya, Tokyo (JP)

(73) Assignees: FUJIFILM CORPORATION, Tokyo (JP); THE UNIVERSITY OF TOKYO, Bunkyo-Ku, Tokyo (JP)

(*) Notice: Subject to any disclaimer, the term of this patent is extended or adjusted under 35 U.S.C. 154(b) by 24 days.

(21) Appl. No.: 15/665,449

(22) Filed: Aug. 1, 2017

(65) Prior Publication Data
US 2017/0338425 A1    Nov. 23, 2017

Related U.S. Application Data

(63) Continuation of application No. PCT/JP2016/053221, filed on Feb. 3, 2016.

(30) Foreign Application Priority Data

Feb. 9, 2015  (JP) .................................. 2015-023358

(51) Int. Cl.
*H01B 1/12*    (2006.01)
*H01L 51/00*    (2006.01)
(Continued)

(52) U.S. Cl.
CPC ........ *H01L 51/0074* (2013.01); *C07D 495/14* (2013.01); *C09B 57/00* (2013.01); (Continued)

(58) Field of Classification Search
CPC ........ C07D 495/14; C09B 57/00; C09D 5/24; H01L 51/0004; H01L 51/0028; (Continued)

(56) References Cited

U.S. PATENT DOCUMENTS

2014/0034915 A1* 2/2014 Lee .................... H01L 51/0074
257/40
2015/0333265 A1  11/2015  Welker et al.
(Continued)

FOREIGN PATENT DOCUMENTS

CN    103570653 A    2/2014
CN    106232593 A    12/2016
(Continued)

OTHER PUBLICATIONS

International Search Report issued in International Application No. PCT/JP2016/053221 dated Apr. 26, 2016.
(Continued)

*Primary Examiner* — Mark Kopec
*Assistant Examiner* — Jaison P Thomas
(74) *Attorney, Agent, or Firm* — Solaris Intellectual Property Group, PLLC

(57) ABSTRACT

Objects of the present invention is to provide an organic semiconductor element having high mobility and to provide a composition for forming an organic semiconductor film with which an organic semiconductor film having high mobility can be formed, a method of manufacturing an organic semiconductor element formed from the composition for forming an organic semiconductor film, and a method of manufacturing an organic semiconductor film.

(Continued)

The organic semiconductor element according to the present invention has a semiconductor active layer including a compound that is represented by Formula 1 and has a molecular weight of 3,000 or less. The composition for forming an organic semiconductor film according to the present invention contains a compound that is represented by Formula 1 and has a molecular weight of 3,000 or less, and a solvent.

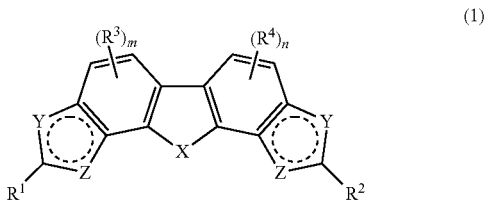

(1)

14 Claims, 3 Drawing Sheets

(51) Int. Cl.
C07D 495/14 (2006.01)
H01L 51/05 (2006.01)
C09B 57/00 (2006.01)
H01B 1/00 (2006.01)
C09D 5/24 (2006.01)

(52) U.S. Cl.
CPC .............. C09D 5/24 (2013.01); H01B 1/00 (2013.01); H01B 1/12 (2013.01); H01L 51/0004 (2013.01); H01L 51/0028 (2013.01); H01L 51/05 (2013.01); H01L 51/0545 (2013.01); H01L 51/0566 (2013.01)

(58) Field of Classification Search
CPC . H01L 51/0074; H01L 51/05; H01L 51/0545; H01L 51/0566; H01B 1/12
See application file for complete search history.

(56) References Cited

U.S. PATENT DOCUMENTS

2016/0104842 A1*  4/2016  Takeya ............... H01L 51/0003
                                                            257/40
2016/0365519 A1* 12/2016  Jiao .................... C07D 495/14
2017/0237005 A1   8/2017  Weitz et al.
2017/0250347 A1   8/2017  Vladimirov et al.

FOREIGN PATENT DOCUMENTS

CN       107004768 A     8/2017
JP       2013-235903 A  11/2013
JP       2015-195361 A  11/2015
JP       2015-195362 A  11/2015
KR       20140017400 A   2/2014
WO       2014/057685 A1  4/2014
WO       2014/086722 A1  6/2014
WO       2014/175351 A1 10/2014
WO       2015/128779 A1  9/2015
WO       2016/027217 A1  2/2016

OTHER PUBLICATIONS

Written Opinion of the ISA issued in International Application No. PCT/JP2016/053221 dated Apr. 26, 2016.
Office Action against a same family Japanese Application dated Apr. 4, 2017.
Koichi Imamura et al., "Application of flash vacuum pyrolysis to the synthesis of sulfur-containing heteroaromatic systems", Tetrahedron Letters, vol. 40, Apr. 2, 1999, pp. 2789-2792.
English language translation of the following: Office action dated Sep. 17, 2018 from the KIPO in a Korean patent application No. 10-2017-7021805 corresponding to the instant patent application. The office action translation is submitted now in order to supplement the understanding of the cited reference which is being disclosed in the instant Information Disclosure Statement.
Extended European Search Report dated Dec. 15, 2017, issued in corresponding EP Patent Application No. 16749122.4.
Koichi Mitsudo et al., "Synthesis and Properties of Ethene-Bridged Terthiophenes", Organic Letters, vol. 17, No. 19, American Chemical Society, US, Sep. 18, 2015, pp. 4858-4861. X055426401, D01:10.1021/acs.orglett.5b02417.
Database Registry[Online], Chemical Abstracts Service, Columbus, OH, US, Mar. 4, 2014. XP-002775971, retrieved from STN Database accession No. 1562157-36-1 *RN: 1562157-36-1*.
Brigitte Wex et al., "End-capping of conjugated thiophene-benzene aromatic systems", Tetrahedron, vol. 66, No. 45, Elsevier Science Publishers, Amsterdam, NL, Nov. 6, 2010, pp. 8778-8784. X027415307, ISSN: 0040-4020.
Office Action dated Mar. 13 2019, issued by the KIPO in corresponding Korean Patent Application No. 10-2017-7021805.
English language translation of the following: Office action dated Jan. 28, 2019 from the SIPO in a Chinese patent application No. 201680008803.9 corresponding to the instant patent application. This office action translation is submitted now in order to supplement the understanding of the cited reference which are being disclosed in the instant Information Disclosure Statement.
Search Report of the Chinese office action dated Jan. 14, 2019, from the SIPO in a Chinese patent application corresponding to the instant patent application.
English language translation of the following: Office action dated Jun. 19, 2019 from the TIPO in a Taiwan patent application No. 105103088 corresponding to the instant patent application.

* cited by examiner

ORGANIC SEMICONDUCTOR ELEMENT, MANUFACTURING METHOD THEREOF, COMPOSITION FOR FORMING ORGANIC SEMICONDUCTOR FILM, AND METHOD OF MANUFACTURING ORGANIC SEMICONDUCTOR FILM

CROSS-REFERENCE TO RELATED APPLICATIONS

This application is a Continuation of International Application No. PCT/JP2016/053221 filed on Feb. 3, 2016, which claims priority to Japanese Patent Application No. 2015-023358 filed on Feb. 9, 2015. The entire contents of these applications are incorporated herein by reference.

BACKGROUND OF THE INVENTION

1. Field of the Invention

The present invention relates to an organic semiconductor element, a manufacturing method thereof, a composition for forming an organic semiconductor film, and a method of manufacturing an organic semiconductor film.

2. Description of the Related Art

An organic transistor having an organic semiconductor film (semiconductor active layer) is used in a field effect transistor (FET) used in a liquid crystal display or an organic EL display, a RFID (RF Tag), and the like, because lightening of weight, cost reduction, and flexibilization can be achieved.

As an organic semiconductor in the related art, those disclosed in JP2013-235903A or WO2014/057685A are known.

SUMMARY OF THE INVENTION

An object to be achieved by the present invention is to provide an organic semiconductor element having high mobility.

Another object to be achieved by the present invention is to provide a composition for forming an organic semiconductor film with which an organic semiconductor film having high mobility can be formed, a method of manufacturing an organic semiconductor element formed from the composition for forming an organic semiconductor film, and a method of manufacturing an organic semiconductor film.

The object of the present invention is solved by the means described in <1> or <11> to <13> below.<2> to <10> which are preferable embodiments are also described below.<1> An organic semiconductor element comprising: a semiconductor active layer including a compound that is represented by Formula 1 and has a molecular weight of 3,000 or less,

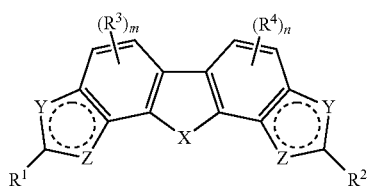
(1)

in which, in Formula 1, X represents an oxygen atom, a sulfur atom, a selenium atom, or a tellurium atom, Y and Z each independently represent $CR^5$, an oxygen atom, a sulfur atom, a selenium atom, a nitrogen atom, or $NR^6$, two Y's may be identical to or different from each other, and two Z's may be identical to or different from each other, all rings including Y and Z are aromatic hetero ring, the aromatic hetero rings including $R^1$ and $R^2$ and Y and Z may be bonded to each other via the following group A of divalent linking groups, $R^3$, $R^4$, and a benzene ring may be bonded to each other via the following group A of divalent linking groups, the group A of divalent linking groups represents any one divalent linking group of —O—, —S—, —$NR^7$—, —CO—, —SO—, and —$SO_2$— or a divalent linking group obtained by bonding two or more of these divalent linking groups, m and n each independently represent an integer of 0 to 2, $R^1$, $R^2$, $R^5$, $R^6$, and $R^7$ each independently represent a hydrogen atom, an alkyl group, an alkenyl group, an alkynyl group, an aryl group, or a heteroaryl group, and $R^3$ and $R^4$ each independently represent an alkyl group, an alkenyl group, an alkynyl group, an aryl group, or a heteroaryl group, in a case where there are two $R^3$'s, the two $R^3$'s may be identical to or different from each other, and in a case where there are two $R^4$'s, the two $R^4$'s may be identical to or different from each other.

<2> The organic semiconductor element according to <1>, in which the aromatic hetero rings including Y and Z are each independently a thiophene ring, a furan ring, a pyrrole ring, a selenophene ring, a thiazole ring, or an oxazole ring.

<3> The organic semiconductor element according to <1> or <2>, in which the numbers of carbon atoms of $R^1$ and $R^2$ are each independently 1 to 30.

<4> The organic semiconductor element according to any one of <1> to <3>, in which both of m and n are 0.

<5> The organic semiconductor element according to any one of <1> to <4>, in which $R^1$ and $R^2$ each independently represent an alkyl group having 1 to 20 carbon atoms, an aryl group having 6 to 20 carbon atoms, and an heteroaryl group having 3 to 20 carbon atoms.

<6> The organic semiconductor element according to any one of <1> to <5>, in which $R^1$ and $R^2$ identical to each other, $R^3$ and $R^4$ are identical to each other, and m and n are identical to each other.

<7> The organic semiconductor element according to any one of <1> to <6>, in which the compound that is represented by Formula 1 and has a molecular weight of 3,000 or less is a compound that is represented by Formula 2 or 3 and has a molecular weight of 3,000 or less,

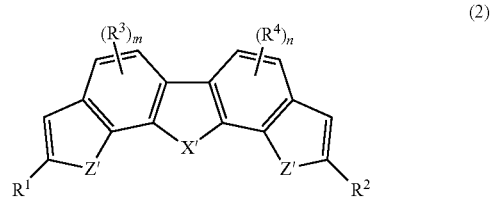
(2)

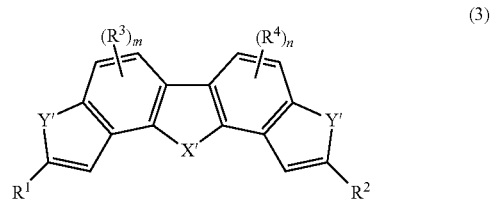
(3)

in Formulae 2 and 3, X"s each independently represent an oxygen atom, a sulfur atom, or a selenium atom, Y' and Z' each independently represent $NR^8$, an oxygen atom, a sulfur atom, or a selenium atom, $R^1$ and $R^2$ and an aromatic hetero ring including Y' or Z' may be bonded to each other via the group A of divalent linking groups, $R^3$, $R^4$, and a benzene ring may be bonded to each other via the following group A of divalent linking groups, the group A of divalent linking groups represents any one divalent linking group of —O—, —S—, —$NR^9$—, —CO—, —SO—, and —$SO_2$— or a divalent linking group obtained by bonding two or more of these divalent linking groups, m and n each independently represent an integer of 0 to 2, $R^1$, $R^2$, $R^8$, and $R^9$ each independently represent a hydrogen atom, an alkyl group, an alkenyl group, an alkynyl group, an aryl group, or a heteroaryl group, and $R^3$ and $R^4$ each independently represent an alkyl group, an alkenyl group, an alkynyl group, an aryl group, or a heteroaryl group, in a case where there are two $R^3$'s, the two $R^3$'s may be identical to or different from each other, and in a case where there are two $R^4$'s, the two $R^4$'s may be identical to or different from each other.

<8> The organic semiconductor element according to any one of <1> to <7>, in which the compound that is represented by Formula 1 and has a molecular weight of 3,000 or less is a compound that is represented by Formula 4 or 5 and has a molecular weight of 3,000 or less,

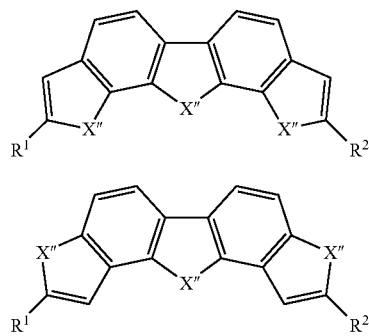

in Formulae 4 and 5, X'''s each independently represent an oxygen atom, a sulfur atom, or a selenium atom, $R^1$ and $R^2$ and an aromatic hetero ring including X'' may be bonded to each other via the following group A of divalent linking groups, the group A of divalent linking groups represents any one divalent linking group of —O—, —S—, —$NR^{10}$—, —CO—, —SO—, and —$SO_2$— or a divalent linking group obtained by bonding two or more of these divalent linking groups, and $R^1$, $R^2$, and $R^{10}$ each independently represent a hydrogen atom, an alkyl group, an alkenyl group, an alkynyl group, an aryl group, or a heteroaryl group.

<9> The organic semiconductor element according to any one of <1> to <8>, in which $R^1$ and $R^2$ are each independently a group at least having an alkyl group, an alkenyl group, or an alkynyl group.

<10> The organic semiconductor element according to any one of <1> to <9>, in which $R^1$ and $R^2$ are each independently a linear alkyl group.

<11> A composition for forming an organic semiconductor film, comprising: a compound that is represented by Formula 1 and has a molecular weight of 3,000 or less, and a solvent,

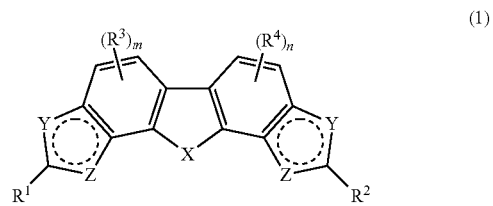

in which, in Formula 1, X represents an oxygen atom, a sulfur atom, a selenium atom, or a tellurium atom, Y and Z each independently represent $CR^5$, an oxygen atom, a sulfur atom, a selenium atom, a nitrogen atom, or $NR^6$, two Y's may be identical to or different from each other, and two Z's may be identical to or different from each other, all rings including Y and Z are aromatic hetero rings, the aromatic hetero rings including $R^1$ and $R^2$ and Y and Z may be bonded to each other via the following group A of divalent linking groups, $R^3$, $R^4$, and a benzene ring may be bonded to each other via the following group A of divalent linking groups, the group A of divalent linking groups represents any one divalent linking group of —O—, —S—, —$NR^7$—, —CO—, —SO—, and —$SO_2$— or a divalent linking group obtained by bonding two or more of these divalent linking groups, m and n each independently represent an integer of 0 to 2, $R^1$, $R^2$, $R^5$, $R^6$, and $R^7$ each independently represent a hydrogen atom, an alkyl group, an alkenyl group, an alkynyl group, an aryl group, or a heteroaryl group, and $R^3$ and $R^4$ each independently represent an alkyl group, an alkenyl group, an alkynyl group, an aryl group, or a heteroaryl group, in a case where there are two $R^3$'s, the two $R^3$'s may be identical to or different from each other, and in a case where there are two $R^4$'s, the two $R^4$'s may be identical to or different from each other.

<12> A method of manufacturing an organic semiconductor element, comprising: a step of manufacturing a semiconductor active layer by coating a substrate with the composition for forming an organic semiconductor film according to <11> and drying the composition.

<13> A method of manufacturing an organic semiconductor film, comprising: a step of dropwise adding the composition for forming an organic semiconductor film according to <11> to a portion of an in-plane of a substrate A so as to be in contact with both of the substrate A and a member B that is not in contact with the substrate A, while maintaining a state in which a distance between the substrate A and the member B is maintained to be constant or a state in which the substrate A and the member B are brought into contact with each other; and a step of precipitating crystals of the compound by drying the dropwise added composition to form a semiconductor active layer.

According to the present invention, it is possible to provide an organic semiconductor element having high mobility.

According to the present invention, a composition for forming an organic semiconductor film with which an organic semiconductor film having high mobility can be formed, a method of manufacturing an organic semiconductor element formed from the composition for forming an organic semiconductor film, and a method of manufacturing an organic semiconductor film.

DESCRIPTION OF THE PREFERRED EMBODIMENTS

Figure 1:
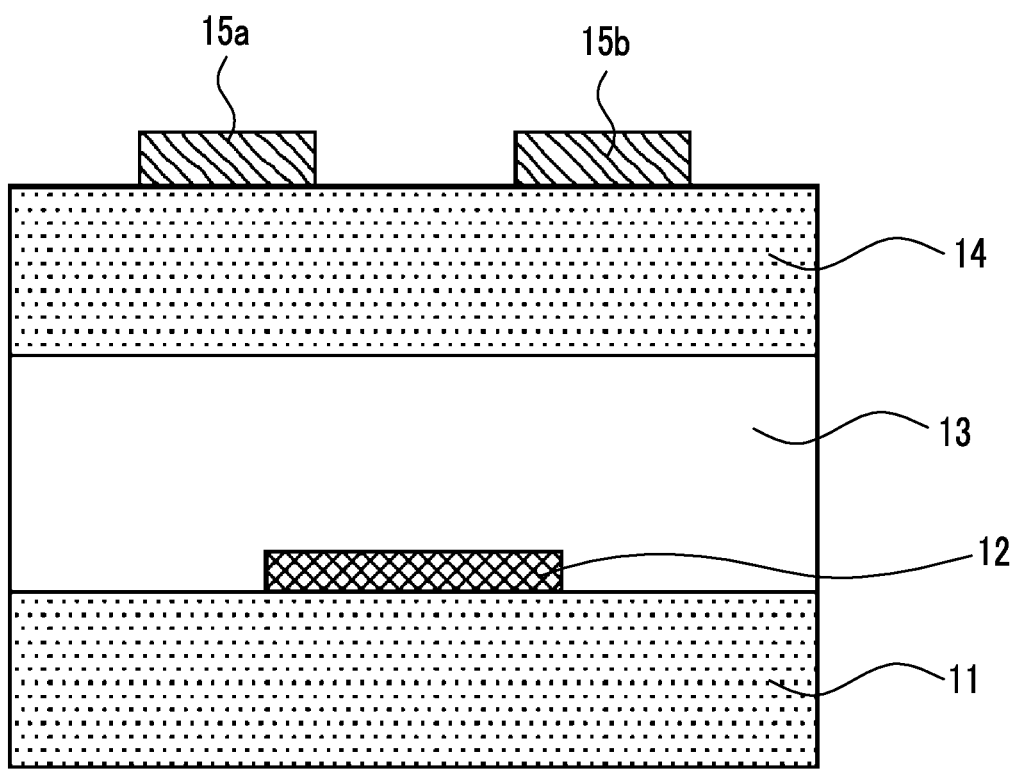
FIG. 1 is a schematic cross-sectional view of an aspect of an organic semiconductor element according to the present invention.

Hereinafter, the contents of the present invention will be specifically described. The constituents in the following description will be explained based on typical embodiments of the present invention, but the present invention is not limited to the embodiments. In the specification of the present application, "to" is used to mean that the numerical values listed before and after "to" are a lower limit and an upper limit respectively. The organic EL element according to the present invention refers to an organic electroluminescence element.

In the present specification, in a case where there is no description regarding whether a group (atomic group) is substituted or unsubstituted, the group includes both of a group having a substituent and a group not having a substituent. For example, an "alkyl group" includes not only an alkyl group not having a substituent (unsubstituted alkyl group) but also an alkyl group having a substituent (substituted alkyl group).

In the present specification, in some cases, a chemical structural formula is described as a simplified structural formula in which a hydrogen atom is omitted.

In the present invention, "mobility" refers to "carrier mobility" and means any one or both of electron mobility and hole mobility.

In the present invention, "mass %" and "weight %" have the same definition, and "part by mass" and "part by weight" have the same definition.

In the present invention, a combination of preferred aspects is more preferable.

(Organic semiconductor element and compound)

The organic semiconductor element according to the present invention has a semiconductor active layer including a compound (hereinafter, simply referred to as a "compound represented by Formula 1" or a "specific compound") that is represented by Formula 1 and has a molecular weight of 3,000 or less.

The compound according to the present invention is a compound that is represented by Formula 1 and has a molecular weight of 3,000 or less.

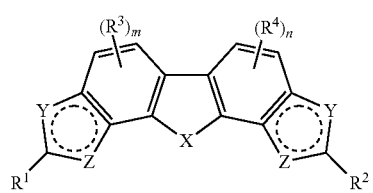

(1)

In Formula 1,

X represents an oxygen atom, a sulfur atom, a selenium atom, or a tellurium atom, Y and Z each independently represent $CR^5$, an oxygen atom, a sulfur atom, a selenium atom, a nitrogen atom, or $NR^6$, two Y's may be identical to or different from each other, and two Z's may be identical to or different from each other, all rings including Y and Z are aromatic hetero rings, the aromatic hetero rings including $R^1$ and $R^2$ and Y and Z may be bonded to each other via a group A of divalent linking groups, $R^3$, $R^4$, and a benzene ring may be bonded to each other via the group A of divalent linking groups, the group A of divalent linking groups represents any one divalent linking group of —O—, —S—, —$NR^7$—, —CO—, —SO—, and —$SO_2$— or a divalent linking group obtained by bonding two or more of these divalent linking groups, m and n each independently represent an integer of 0 to 2, $R^1$, $R^2$, $R^5$, $R^6$, and $R^7$ each independently represent a hydrogen atom, an alkyl group, an alkenyl group, an alkynyl group, an aryl group, or a heteroaryl group, and $R^3$ and $R^4$ each independently represent an alkyl group, an alkenyl group, an alkynyl group, an aryl group, or a heteroaryl group, in a case where there are two $R^3$'s, the two $R^3$'s may be identical to or different from each other, and in a case where there are two $R^4$'s, the two $R^4$'s may be identical to or different from each other.

It is preferable that the compound represented by Formula 1 is not a multimer such as an oligomer and a polymer.

In the semiconductor active layer, it is preferable that the compounds represented by Formula 1 are not bonded to each other by a covalent bond, and it is preferable that a crystal structure such as a polycrystal structure and/or an amorphous structure is formed.

The compound according to the present invention can be suitably used as an organic semiconductor compound and can be suitably contained in an organic semiconductor material for forming an organic semiconductor element, a composition for forming an organic semiconductor film, and an organic semiconductor film for an organic semiconductor element.

<Compound that is represented by Formula 1 and has molecular weight of 3,000 or less>

The compound according to the present invention that is represented by Formula 1 and has a molecular weight of 3,000 or less is a novel compound and can be suitably used as an organic semiconductor compound.

The molecular weight of the compound represented by Formula 1 is 3,000 or less, preferably 250 to 2,000, more preferably 300 to 1,000, and even more preferably 350 to 800.

X in Formula 1 represents an oxygen atom, a sulfur atom, a selenium atom, or a tellurium atom. In view of mobility, stability, and cost, an oxygen atom, a sulfur atom, or a selenium atom is preferable, a sulfur atom or a selenium atom is more preferable, and a sulfur atom is even more preferable.

Y and Z in Formula 1 each independently represent $CR^5$, an oxygen atom, a sulfur atom, a selenium atom, a nitrogen atom, or $NR^6$. In view of mobility and film formability, it is preferable that any one of Y and Z is an oxygen atom, a sulfur atom, a selenium atom, and $NR^6$ and the other is $CR^5$ or a nitrogen atom, it is more preferable that any one of Y and Z is an oxygen atom, a sulfur atom, a selenium atom, or $NR^6$ and the other is $CR^5$, and it is even more preferable that any one of Y and Z is a sulfur atom and the other is $CR^5$.

$R^5$ and $R^6$ each independently represent a hydrogen atom, an alkyl group, an alkenyl group, an alkynyl group, an aryl group, or a heteroaryl group.

$R^5$ is preferably a hydrogen atom.

$R^6$ is preferably a hydrogen atom, an alkyl group, or an aryl group, more preferably a hydrogen atom or an alkyl group, even more preferably a hydrogen atom or an alkyl group having 1 to 20 carbon atoms, and particularly preferably an alkyl group having 1 to 20 carbon atoms.

Two Y's may be identical to or different from each other but are preferably identical to each other.

Two Z's may be identical to or different from each other but are preferably identical to each other.

All rings including Y and Z in Formula 1 are aromatic hetero rings, the rings including Y and Z are each independently and preferably a thiophene ring, a furan ring, a pyrrole ring, a selenophene ring, and a thiazole ring or oxazole ring, more preferably a thiophene ring, a furan ring, a pyrrole ring, or a selenophene ring, and even more preferably a thiophene ring.

Here, in Formula 1, it is preferable that a case where both of Y and Z are $CR^5$, a case where Y is a nitrogen atom or $NR^6$ and Z is a nitrogen atom or $NR^6$, and a case where Y and Z are bonded to carbon atoms at two or more positions other than positions at which benzene rings are fused to aromatic hetero rings including Y and Z are excluded.

$R^1$ and $R^2$ in Formula 1 each independently represent a hydrogen atom, an alkyl group, an alkenyl group, an alkynyl group, an aryl group, or a heteroaryl group, is preferably an alkyl group, an alkenyl group, an alkynyl group, an aryl group, or a heteroaryl group, is more preferably an alkyl group having 1 to 20 carbon atoms, an aryl group having 6 to 20 carbon atoms, and a heteroaryl group having 3 to 20 carbon atoms, even more preferably an alkyl group having 1 to 20 carbon atoms, particularly preferably an alkyl group having 2 to 15 carbon atoms, and most preferably an alkyl group having 3 to 10 carbon atoms. In this aspect, mobility is more excellent.

The numbers of carbon atoms of $R^1$ and $R^2$ are each independently and preferably 0 to 30, more preferably 2 to 25, even more preferably 4 to 20, and particularly preferably 6 to 16. In this range, mobility is more excellent.

$R^1$ and $R^2$ in Formula 1 are preferably the same groups. In this aspect, mobility is more excellent.

Alkyl groups in $R^1$ and $R^2$ are preferably linear alkyl groups.

$R^3$ and $R^4$ in Formula 1 each independently represent an alkyl group, an alkenyl group, an alkynyl group, an aryl group, or a heteroaryl group. In a case where there are two $R^3$'s, $R^3$'s may be identical to or different from each other, and in a case where there are two $R^4$'s, $R^4$'s may be identical to or different from each other.

The numbers of carbon atoms of $R^3$ and $R^4$ are each independently and preferably 1 to 30 and more preferably 1 to 20.

$R^3$ and $R^4$ in Formula 1 are preferably the same groups.

m and n in Formula 1 are each independently an integer of 0 to 2 and preferably 0 or 1, and it is more preferable that both of m and n are 0.

m and n in Formula 1 are preferably identical to each other.

In Formula 1, $R^1$ and $R^2$ and aromatic hetero rings including Y and Z may be bonded to each other via the group A of divalent linking groups, and $R^3$, $R^4$, and benzene rings are may be bonded to each other via the group A of divalent linking groups.

The group A of divalent linking groups represents any one divalent linking group of —O—, —S—, —$NR^7$—, —CO—, —SO—, and —$SO_2$—, or a divalent linking group obtained by bonding two or more of these divalent linking groups, is preferably —O—, —S—, —$NR^7$—, —CO—, —O—CO—, —CO—O—, —$NR^7$—CO—, —CO—$NR^7$—, —O—CO—O—, —$NR^7$—O—, —O—CO—$NR^7$—, or —$NR^7$—CO—$NR^7$—, and more preferably —O—, —S—, —$NR^7$—, —CO—, —O—CO—, or —CO—O—.

It is preferable that $R^1$ and $R^2$ are not bonded via A, that is, $R^1$ and $R^2$ do not have A.

$R^7$'s each independently represent a hydrogen atom, an alkyl group, an alkenyl group, an alkynyl group, an aryl group, or a heteroaryl group, preferably a hydrogen atom, an alkyl group, or an aryl group, more preferably a hydrogen atom or an alkyl group, and even more preferably an alkyl group having 1 to 8 carbon atoms.

In Formula 1, an alkyl group, an alkenyl group, an alkynyl group, an aryl group, and a heteroaryl group in $R^1$ to $R^7$ may further have substituents.

Examples of the substituent include a halogen atom, an alkyl group (including a cycloalkyl group, a bicycloalkyl group, and a tricycloalkyl group), an aryl group, a heterocyclic group, a cyano group, a hydroxy group, a nitro group, a carboxy group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkyl and arylsulfonylamino group, a mercapto group, an alkylthio group, an arylthio group, a heterocyclic thio group, a sulfamoyl group, a sulfo group, an alkyl and arylsulfinyl group, an alkyl and arylsulfonyl group, an acyl group, an aryloxycarbonyl group, an alkoxycarbonyl group, a carbamoyl group, an aryl and heterocyclic azo group, an imido group, a phosphino group, a phosphinyl group, a phosphinyloxy group, a phosphinylamino group, a phosphono group, a silyl group, a hydrazino group, a ureido group, a boronic acid group (—$B(OH)_2$), a phosphato group (—$OPO(OH)_2$), a sulfato group (—$OSO_3H$), and other well-known substituents. The substituents may be further substituted with sub stituents.

Among these, the substituent is preferably a halogen atom, an alkyl group, an alkoxy group, an alkylthio group, and an aryl group, more preferably a fluorine atom, a substituted or unsubstituted alkyl group having 1 to 10 carbon atoms, a substituted or unsubstituted alkoxy group having 1 to 10 carbon atoms, a substituted or unsubstituted methylthio group, and a phenyl group, particularly preferably a fluorine atom, a substituted or unsubstituted alkyl group having 1 to 10 carbon atoms, a substituted or unsubstituted alkoxy group having 1 to 10 carbon atoms, and a substituted or unsubstituted methylthio group.

It is preferable that the compound represented by Formula 1 is represented by Formula 2 or 3 and is a compound having a molecular weight of 3,000 or less.

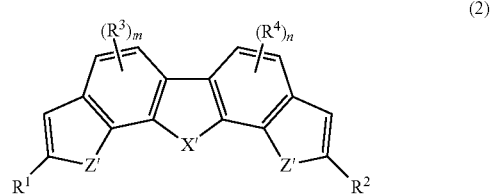

(2)

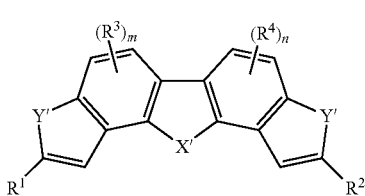

(3)

In Formulae 2 and 3,

X"'s each independently represent an oxygen atom, a sulfur atom, or a selenium atom, Y' and Z' each independently represent $NR^8$, an oxygen atom, a sulfur atom, or a selenium atom, $R^1$ and $R^2$ and aromatic hetero rings including Y' or Z' may be bonded to each other via the group A of divalent linking groups, $R^3$, $R^4$, and benzene rings may be bonded to each other via the group A of divalent linking groups, the group A of divalent linking groups represents any one divalent linking group of —O—, —S—, —$NR^9$—, —CO—, —SO—, and —$SO_2$— or a divalent linking group obtained by bonding two or more of these divalent linking groups, m and n each independently represent an integer of 0 to 2, $R^1$, $R^2$, $R^8$, and $R^9$ each independently represent a hydrogen atom, an alkyl group, an alkenyl group, an alkynyl group, an aryl group, or a heteroaryl group, $R^3$ and $R^4$ each independently represent an alkyl group, an alkenyl group, an alkynyl group, an aryl group, or a heteroaryl group, in a case where there are two $R^3$'s, $R^3$'s may be identical to or different from each other, and in a case where there are two $R^4$'s, $R^4$'s may be identical to or different from each other.

$R^1$ to $R^4$, and m and n in Formulae 2 and 3 are identical to $R^1$ to $R^4$, and m and n in Formula 1, and preferable aspects are also identical.

X"'s in Formulae 2 and 3 each independently represent an oxygen atom, a sulfur atom, or a selenium atom. In view of mobility, X' is preferably a sulfur atom or a selenium atom and more preferably a sulfur atom.

Y' and Z' in Formulae 2 and 3 each independently represent $NR^8$, an oxygen atom, a sulfur atom, or a selenium atom. In view of mobility and film formability, Y' and Z' each are preferably an oxygen atom, a sulfur atom, or a selenium atom, more preferably a sulfur atom or a selenium atom, and even more preferably a sulfur atom.

$R^8$ represents a hydrogen atom, an alkyl group, an alkenyl group, an alkynyl group, an aryl group, or a heteroaryl group, preferably a hydrogen atom, an alkyl group, or an aryl group, more preferably a hydrogen atom or an alkyl group, even more preferably a hydrogen atom or an alkyl group having 1 to 20 carbon atoms, and particularly preferably a hydrogen atom.

Two Y"'s in Formula 2 are preferably the same group, and Two Z"'s in Formula 3 are preferably the same group.

In Formulae 2 and 3, $R^1$ and $R^2$ and aromatic hetero rings including Y' and Z' may be bonded to each other via the group A of divalent linking groups, it is preferable that $R^1$ is not bonded via A, that is, does not have A. It is preferable that $R^2$ is not bonded via A, that is, does not have A.

In Formulae 2 and 3, $R^3$, $R^4$, and benzene rings may be bonded via the group A of divalent linking groups.

The groups A of divalent linking groups in Formulae 2 and 3 represent any one divalent linking group of —O—, —S—, —$NR^9$—, —CO—, —SO—, and —$SO_2$— or a divalent linking group obtained by bonding two or more of these divalent linking groups, preferably —O—, —S—, —$NR^9$—, —CO—, —O—CO—, —CO—O—, —$NR^9$—CO—, —CO—$NR^9$—, —O—CO—O—, —$NR^9$—CO—O—, —O—CO—$NR^9$—, or —$NR^9$—CO—$NR^9$—, and more preferably —O—, —S—, —$NR^9$—, —CO—, —O—CO—, or —CO—O—.

$R^9$ represents a hydrogen atom, an alkyl group, an alkenyl group, an alkynyl group, an aryl group, or a heteroaryl group, preferably a hydrogen atom, an alkyl group, or an aryl group, more preferably a hydrogen atom or an alkyl group, and even more preferably an alkyl group having 1 to 8 carbon atoms.

An alkyl group, an alkenyl group, an alkynyl group, an aryl group, and a heteroaryl group in $R^1$, $R^2$, $R^8$, and $R^9$ in Formulae 2 and Formula 3 may further have substituents.

The substituent in $R^1$, $R^2$, $R^8$, and $R^9$ in Formulae 2 and 3 is preferably the substituents described above.

It is more preferable that the compound represented by Formula 1 is represented by Formula 4 or 5 and is a compound having a molecular weight of 3,000 or less.

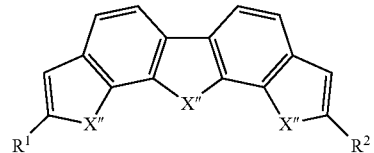

(4)

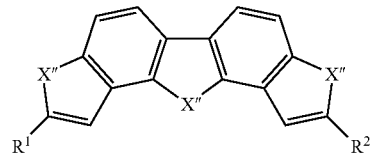

(5)

In Formulae 4 and 5,

X"''s each independently represent an oxygen atom, a sulfur atom, or a selenium atom, $R^1$ and $R^2$ and aromatic hetero rings including X" may be bonded via the group A of divalent linking groups, the group A of divalent linking groups represents any one divalent linking group of —O—, —S—, —$NR^{10}$—, —CO—, —SO—, and —$SO_2$— or a divalent linking group obtained by bonding two or more of these divalent linking groups, and $R^1$, $R^2$, and $R^{10}$ each independently represent a hydrogen atom, an alkyl group, an alkenyl group, an alkynyl group, an aryl group, or a heteroaryl group.

$R^1$ and $R^2$ in Formulae 4 and 5 are identical to $R^1$ and $R^2$ in Formula 1, and preferable aspects thereof are also identical to each other.

X"''s in Formulae 4 and 5 each independently represent an oxygen atom, a sulfur atom, or a selenium atom. In view of mobility and film formability, X" is preferably a sulfur atom or a selenium atom and more preferably a sulfur atom.

It is preferable that all X"''s in Formulae 4 and 5 are identical to each other. $R^1$ and $R^2$ and aromatic hetero rings including X" may be bonded to each other via the group A of divalent linking groups.

The group A of divalent linking groups represents any one divalent linking group of —O—, —S—, —$NR^{10}$—, —CO—, —SO—, and —SO$_2$— or a divalent linking group obtained by bonding two or more of these divalent linking groups, is preferably —O—, —S—, —NR$^{10}$—, —CO—, —O—CO—, —CO—O—, —NR$^{10}$—CO—, —CO—NR$^{10}$—, —O—CO—O—, —NR$^{10}$—CO—O—, —O—CO—NR$^{10}$—, or —NR$^{10}$—CO—NR—, and is more preferably —O—, —S—, —NR$^{10}$—, —CO—, —O—CO—, or —CO—O—.

R$^{10}$ represents a hydrogen atom, an alkyl group, an alkenyl group, an alkynyl group, an aryl group, or a heteroaryl group, preferably a hydrogen atom, an alkyl group, or an aryl group, more preferably a hydrogen atom or an alkyl group, and even more preferably an alkyl group having 1 to 8 carbon atoms.

An alkyl group, an alkenyl group, an alkynyl group, an aryl group, and a heteroaryl group in R$^1$, R$^2$, and R$^{10}$ of Formulae 4 and 5 may further have substituents.

As the substituent in R$^1$, R$^2$, and R$^{10}$ in Formulae 4 and 5, substituents described above are preferable.

Preferable and specific examples of the compound represented by Formula 1 are provided below, but the invention is not limited thereto.

Respective columns in Tables 2 to 35 are identical to those in provided on the first row of Table 1. That is, the respective columns in Tables 2 to 35 represent specific examples, X, Y, Z, m, n, R$^1$, R$^2$, R$^3$, and R$^4$. An example in which Z in the table represents NR$^7$ is presented as N(n-C$_{10}$H$_{21}$).

Both of R$^3$ and R$^4$ in Specific Examples 77, 78, 155, and 156 are groups obtained by substituting hydrogen atoms on benzene rings on the side close to a ring including Y and Z.

TABLE 1

| SPECIFIC EXAMPLE | X | Y | Z | m | n | R$^1$ | R$^2$ | R$^3$ | R$^4$ |
|---|---|---|---|---|---|---|---|---|---|
| 1 | O | CH | O | 0 | 0 | CH$_3$ | CH$_3$ | — | — |
| 2 | O | CH | O | 0 | 0 | n-C$_4$H$_9$ | n-C$_4$H$_9$ | — | — |
| 3 | O | CH | O | 0 | 0 | n-C$_5$H$_{11}$ | n-C$_5$H$_{11}$ | — | — |
| 4 | O | CH | O | 0 | 0 | n-C$_6$H$_{13}$ | n-C$_6$H$_{13}$ | — | — |
| 5 | O | CH | O | 0 | 0 | n-C$_7$H$_{15}$ | n-C$_7$H$_{15}$ | — | — |
| 6 | O | CH | O | 0 | 0 | n-C$_8$H$_{17}$ | n-C$_8$H$_{17}$ | — | — |
| 7 | O | CH | O | 0 | 0 | n-C$_9$H$_{19}$ | n-C$_9$H$_{19}$ | — | — |
| 8 | O | CH | O | 0 | 0 | n-C$_{10}$H$_{21}$ | n-C$_{10}$H$_{21}$ | — | — |
| 9 | O | CH | O | 0 | 0 | n-C$_{11}$H$_{23}$ | n-C$_{11}$H$_{23}$ | — | — |
| 10 | O | CH | O | 0 | 0 | n-C$_{12}$H$_{25}$ | n-C$_{12}$H$_{25}$ | — | — |
| 11 | O | CH | O | 0 | 0 | —O—nC$_6$H$_{13}$ | —O—nC$_6$H$_{13}$ | — | — |
| 12 | O | CH | O | 0 | 0 | —O—nC$_{10}$H$_{21}$ | —O—nC$_{10}$H$_{21}$ | — | — |
| 13 | O | CH | O | 0 | 0 | 2-ethylhexyl | 2-ethylhexyl | — | — |
| 14 | O | CH | O | 0 | 0 | —CH=CH$_2$ (allyl-type) | —CH=CH$_2$ (allyl-type) | — | — |
| 15 | O | CH | O | 0 | 0 | —C≡CH (alkynyl) | —C≡CH (alkynyl) | — | — |
| 16 | O | CH | O | 0 | 0 | —C≡C—Si(iPr)$_3$ | —C≡C—Si(iPr)$_3$ | — | — |
| 17 | O | CH | O | 0 | 0 | phenyl | phenyl | — | — |
| 18 | O | CH | O | 0 | 0 | nC$_6$H$_{13}$-phenyl | nC$_6$H$_{13}$-phenyl | — | — |

TABLE 1-continued
| SPECIFIC EXAMPLE | X | Y | Z | m | n | R¹ | R² | R³ | R⁴ |
|---|---|---|---|---|---|---|---|---|---|
| 19 | O | CH | O | 0 | 0 | 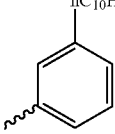 | 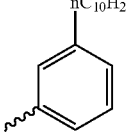 | — | — |
| 20 | O | CH | O | 0 | 0 | 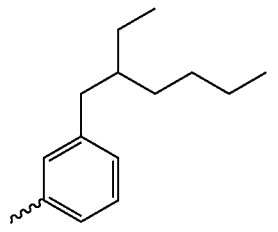 | 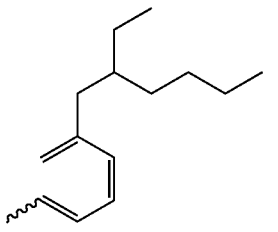 | — | — |
TABLE 2
| | | | | | | | | | |
|---|---|---|---|---|---|---|---|---|---|
| 21 | O | CH | O | 0 | 0 | 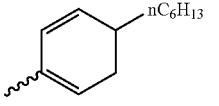 | 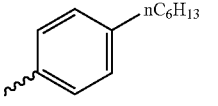 | — | — |
| 22 | O | CH | O | 0 | 0 | 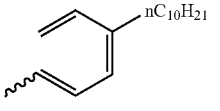 | 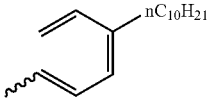 | — | — |
| 23 | O | CH | O | 0 | 0 | 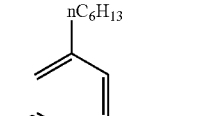 | 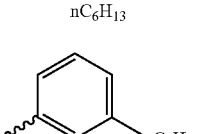 | — | — |
| 24 | O | CH | O | 0 | 0 | 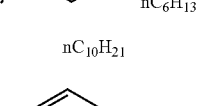 | 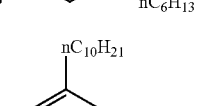 | — | — |
| 25 | O | CH | O | 0 | 0 | 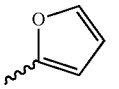 | 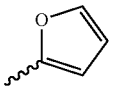 | — | — |
| 26 | O | CH | O | 0 | 0 | 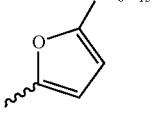 | 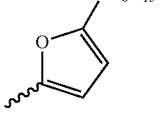 | — | — |
| 27 | O | CH | O | 0 | 0 | 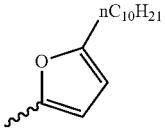 | 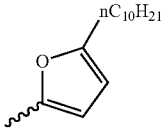 | — | — |
| 28 | O | CH | O | 0 | 0 | 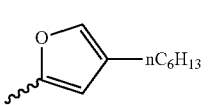 | 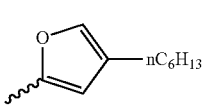 | — | — |

TABLE 2-continued

| | | | | | | | | | | |
|---|---|---|---|---|---|---|---|---|---|---|
| 29 | O | CH | O | 0 | 0 | furan-nC₁₀H₂₁ | furan-nC₁₀H₂₁ | — | — |
| 30 | O | CH | O | 0 | 0 | NH-pyrrole | NH-pyrrole | — | — |
| 31 | O | CH | O | 0 | 0 | N-methylpyrrole-nC₆H₁₃ | N-methylpyrrole-nC₆H₁₃ | — | — |
| 32 | O | CH | O | 0 | 0 | nC₆H₁₃-N-pyrrole | nC₆H₁₃-N-pyrrole | — | — |
| 33 | O | CH | O | 0 | 0 | nC₁₀H₂₁-N-pyrrole | nC₁₀H₂₁-N-pyrrole | — | — |
| 34 | O | CH | O | 0 | 0 | thiophene | thiophene | — | — |
| 35 | O | CH | O | 0 | 0 | thiophene(3) | thiophene(3) | — | — |
| 36 | O | CH | O | 0 | 0 | thiophene-nC₅H₁₁ | thiophene-nC₅H₁₁ | — | — |
| 37 | O | CH | O | 0 | 0 | thiophene-nC₆H₁₃ | thiophene-nC₆H₁₃ | — | — |
| 38 | O | CH | O | 0 | 0 | thiophene-nC₈H₁₇ | thiophene-nC₈H₁₇ | — | — |
| 39 | O | CH | O | 0 | 0 | thiophene-nC₁₀H₂₁ | thiophene-nC₁₀H₂₁ | — | — |
| 40 | O | CH | O | 0 | 0 | thiophene-nC₁₂H₂₅ | thiophene-nC₁₂H₂₅ | — | — |

TABLE 3

| | | | | | | | | | | |
|---|---|---|---|---|---|---|---|---|---|---|
| 41 | O | CH | O | 0 | 0 | thiophene-nC₆H₁₃ | thiophene-nC₆H₁₃ | — | — |

TABLE 3-continued

| 42 | O | CH | O | 0 | 0 | 5-nC₁₀H₂₁-thiophen-2-yl | 5-nC₁₀H₂₁-thiophen-2-yl | — | — |
| 43 | O | CH | O | 0 | 0 | 5-nC₅H₁₁-thiophen-3-yl | 5-nC₅H₁₁-thiophen-3-yl | — | — |
| 44 | O | CH | O | 0 | 0 | 5-nC₆H₁₃-thiophen-3-yl | 5-nC₆H₁₃-thiophen-3-yl | — | — |
| 45 | O | CH | O | 0 | 0 | 5-nC₈H₁₇-thiophen-3-yl | 5-nC₈H₁₇-thiophen-3-yl | — | — |
| 46 | O | CH | O | 0 | 0 | 5-nC₁₀H₂₁-thiophen-3-yl | 5-nC₁₀H₂₁-thiophen-3-yl | — | — |
| 47 | O | CH | O | 0 | 0 | 5-nC₁₂H₂₅-thiophen-3-yl | 5-nC₁₂H₂₅-thiophen-3-yl | — | — |
| 48 | O | CH | O | 0 | 0 | thiazol-2-yl | thiazol-2-yl | — | — |
| 49 | O | CH | O | 0 | 0 | 5-nC₆H₁₃-thiazol-2-yl | 5-nC₆H₁₃-thiazol-2-yl | — | — |
| 50 | O | CH | O | 0 | 0 | 5-nC₁₀H₂₁-thiazol-2-yl | 5-nC₁₀H₂₁-thiazol-2-yl | — | — |
| 51 | O | CH | O | 0 | 0 | 4-nC₆H₁₃-thiazol-2-yl | 4-nC₆H₁₃-thiazol-2-yl | — | — |
| 52 | O | CH | O | 0 | 0 | 4-nC₁₀H₂₁-thiazol-2-yl | 4-nC₁₀H₂₁-thiazol-2-yl | — | — |
| 53 | O | CH | O | 0 | 0 | thieno[3,2-b]thiophen-2-yl | thieno[3,2-b]thiophen-2-yl | — | — |
| 54 | O | CH | O | 0 | 0 | 5-nC₆H₁₃-thieno[3,2-b]thiophen-2-yl | 5-nC₆H₁₃-thieno[3,2-b]thiophen-2-yl | — | — |

TABLE 3-continued

| # | | | | | | Ar1 | Ar2 | | |
|---|---|---|---|---|---|---|---|---|---|
| 55 | O | CH | O | 0 | 0 | thienothiophene-nC10H21 | thienothiophene-nC10H21 | — | — |
| 56 | O | CH | O | 0 | 0 | benzothiophene | benzothiophene | — | — |
| 57 | O | CH | O | 0 | 0 | benzothiophene-nC6H13 | benzothiophene-nC6H13 | — | — |
| 58 | O | CH | O | 0 | 0 | benzothiophene-nC10H21 | benzothiophene-nC10H21 | — | — |
| 59 | O | CH | O | 0 | 0 | benzothiophene-nC6H13 | benzothiophene-nC6H13 | — | — |
| 60 | O | CH | O | 0 | 0 | benzothiophene-nC10H21 | benzothiophene-nC10H21 | — | — |

TABLE 4

| # | | | | | | Ar1 | Ar2 | | |
|---|---|---|---|---|---|---|---|---|---|
| 61 | O | CH | O | 0 | 0 | benzothiophene | benzothiophene | — | — |
| 62 | O | CH | O | 0 | 0 | benzothiophene-nC6H13 | benzothiophene-nC6H13 | — | — |
| 63 | O | CH | O | 0 | 0 | benzothiophene-nC10H21 | benzothiophene-nC10H21 | — | — |

TABLE 4-continued

| 64 | O | CH | O | 0 | 0 | benzothiophene-3-yl with nC6H13 | benzothiophene-3-yl with nC6H13 | — | — |
| 65 | O | CH | O | 0 | 0 | benzothiophene-3-yl with nC10H21 | benzothiophene-3-yl with nC10H21 | — | — |
| 66 | O | CH | O | 0 | 0 | pyridin-2-yl | pyridin-2-yl | — | — |
| 67 | O | CH | O | 0 | 0 | pyridin-4-yl | pyridin-4-yl | — | — |
| 68 | O | CH | O | 0 | 0 | pyridin-3-yl | pyridin-3-yl | — | — |
| 69 | O | CH | O | 0 | 0 | 4-(nC6H13)-pyridin-2-yl | 4-(nC6H13)-pyridin-2-yl | — | — |
| 70 | O | CH | O | 0 | 0 | 4-(nC10H21)-pyridin-2-yl | 4-(nC10H21)-pyridin-2-yl | — | — |
| 71 | O | CH | O | 0 | 0 | 5-(nC6H13)-pyridin-2-yl | 5-(nC6H13)-pyridin-2-yl | — | — |
| 72 | O | CH | O | 0 | 0 | 5-(nC10H21)-pyridin-2-yl | 5-(nC10H21)-pyridin-2-yl | — | — |
| 73 | O | CH | O | 0 | 0 | 2-(nC6H13)-pyridin-4-yl | 2-(nC6H13)-pyridin-4-yl | — | — |
| 74 | O | CH | O | 0 | 0 | 2-(nC10H21)-pyridin-4-yl | 2-(nC10H21)-pyridin-4-yl | — | — |
| 75 | O | CH | O | 0 | 0 | 5-(nC6H13)-pyridin-3-yl | 5-(nC6H13)-pyridin-3-yl | — | — |

TABLE 4-continued
| 76 | O | CH | O | 0 | 0 | 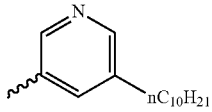 | 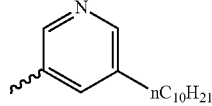 | — | — |
| 77 | O | CH | O | 2 | 2 | H | H | n-C$_6$H$_{13}$ | n-C$_6$H$_{13}$ |
| 78 | O | CH | O | 2 | 2 | H | H | n-C$_{10}$H$_{21}$ | n-C$_{10}$H$_{21}$ |
| 79 | S | CH | O | 0 | 0 | CH$_3$ | CH$_3$ | — | — |
| 80 | S | CH | O | 0 | 0 | n-C$_4$H$_9$ | n-C$_4$H$_9$ | — | — |
TABLE 5
| 81 | S | CH | O | 0 | 0 | n-C$_5$H$_{11}$ | n-C$_5$H$_{11}$ | — | — |
| 82 | S | CH | O | 0 | 0 | n-C$_6$H$_{13}$ | n-C$_6$H$_{13}$ | — | — |
| 83 | S | CH | O | 0 | 0 | n-C$_7$H$_{15}$ | n-C$_7$H$_{15}$ | — | — |
| 84 | S | CH | O | 0 | 0 | n-C$_8$H$_{17}$ | n-C$_8$H$_{17}$ | — | — |
| 85 | S | CH | O | 0 | 0 | n-C$_9$H$_{19}$ | n-C$_9$H$_{19}$ | — | — |
| 86 | S | CH | O | 0 | 0 | n-C$_{10}$H$_{21}$ | n-C$_{10}$H$_{21}$ | — | — |
| 87 | S | CH | O | 0 | 0 | n-C$_{11}$H$_{23}$ | n-C$_{11}$H$_{23}$ | — | — |
| 88 | S | CH | O | 0 | 0 | n-C$_{12}$H$_{25}$ | n-C$_{12}$H$_{25}$ | — | — |
| 89 | S | CH | O | 0 | 0 | 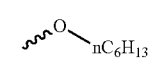 | 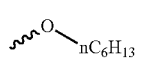 | — | — |
| 90 | S | CH | O | 0 | 0 | 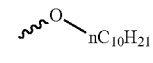 | 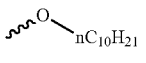 | — | — |
| 91 | S | CH | O | 0 | 0 | 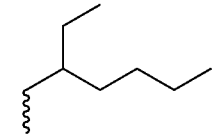 | 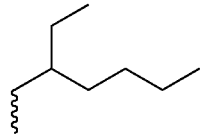 | — | — |
| 92 | S | CH | O | 0 | 0 | 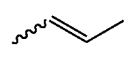 | 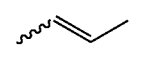 | — | — |
| 93 | S | CH | O | 0 | 0 |  |  | — | — |
| 94 | S | CH | O | 0 | 0 | 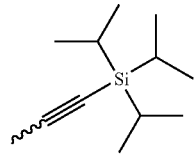 | 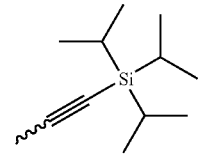 | — | — |
| 95 | S | CH | O | 0 | 0 | 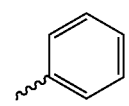 | 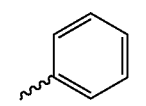 | — | — |
| 96 | S | CH | O | 0 | 0 | 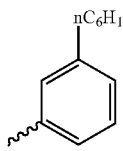 | 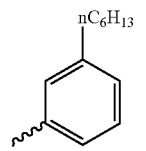 | — | — |
| 97 | S | CH | O | 0 | 0 | 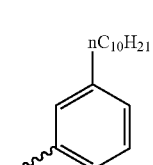 | 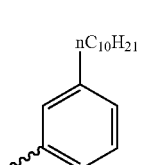 | — | — |

TABLE 5-continued

| 98 | S | CH | O | 0 | 0 | (2-ethylhexyl)benzyl | (2-ethylhexyl)benzyl | — | — |
| 99 | S | CH | O | 0 | 0 | 4-$nC_6H_{13}$-phenyl | 4-$nC_6H_{13}$-phenyl | — | — |
| 100 | S | CH | O | 0 | 0 | 4-$nC_{10}H_{21}$-phenyl | 4-$nC_{10}H_{21}$-phenyl | — | — |

TABLE 6

| 101 | S | CH | O | 0 | 0 | 3,5-di-$nC_6H_{13}$-phenyl | 3,5-di-$nC_6H_{13}$-phenyl | — | — |
| 102 | S | CH | O | 0 | 0 | 3,5-di-$nC_{10}H_{21}$-phenyl | 3,5-di-$nC_{10}H_{21}$-phenyl | — | — |
| 103 | S | CH | O | 0 | 0 | furan-2-yl | furan-2-yl | — | — |
| 104 | S | CH | O | 0 | 0 | 5-$nC_6H_{13}$-furan-2-yl | 5-$nC_6H_{13}$-furan-2-yl | — | — |
| 105 | S | CH | O | 0 | 0 | 5-$nC_{10}H_{21}$-furan-2-yl | 5-$nC_{10}H_{21}$-furan-2-yl | — | — |
| 106 | S | CH | O | 0 | 0 | 4-$nC_6H_{13}$-furan-2-yl | 4-$nC_6H_{13}$-furan-2-yl | — | — |
| 107 | S | CH | O | 0 | 0 | 4-$nC_{10}H_{21}$-furan-2-yl | 4-$nC_{10}H_{21}$-furan-2-yl | — | — |
| 108 | S | CH | O | 0 | 0 | 1H-pyrrol-2-yl | 1H-pyrrol-2-yl | — | — |

TABLE 6-continued
| | | | | | | | | |
|---|---|---|---|---|---|---|---|---|
| 109 | S | CH | O | 0 | 0 | 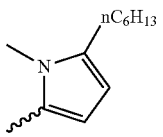 | 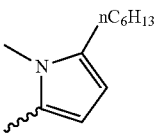 | — — |
| 110 | S | CH | O | 0 | 0 | 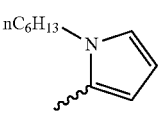 | 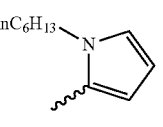 | — — |
| 111 | S | CH | O | 0 | 0 | 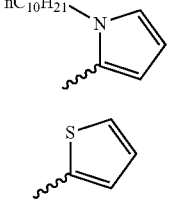 | 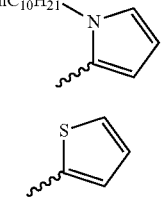 | — — |
| 112 | S | CH | O | 0 | 0 |  |  | — — |
| 113 | S | CH | O | 0 | 0 |  | 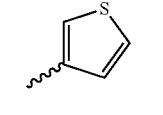 | — — |
| 114 | S | CH | O | 0 | 0 | 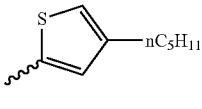 | 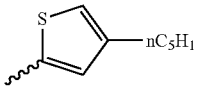 | — — |
| 115 | S | CH | O | 0 | 0 | 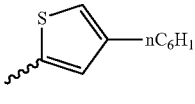 | 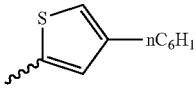 | — — |
| 116 | S | CH | O | 0 | 0 | 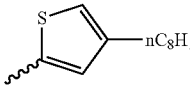 | 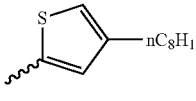 | — — |
| 117 | S | CH | O | 0 | 0 | 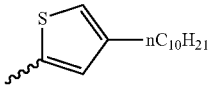 | 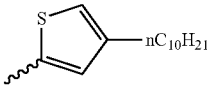 | — — |
| 118 | S | CH | O | 0 | 0 | 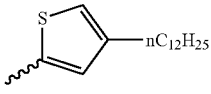 | 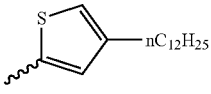 | — — |
| 119 | S | CH | O | 0 | 0 | 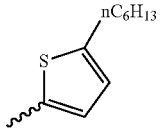 | 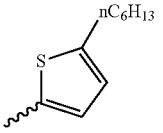 | — — |
| 120 | S | CH | O | 0 | 0 | 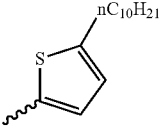 | 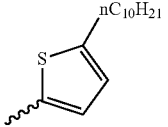 | — — |
TABLE 7
| | | | | | | | | |
|---|---|---|---|---|---|---|---|---|
| 121 | S | CH | O | 0 | 0 | 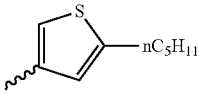 | 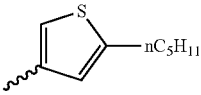 | — — |

TABLE 7-continued
| 122 | S | CH | O | 0 | 0 | 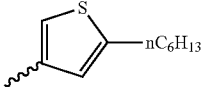 | 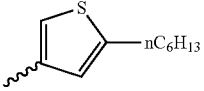 | — | — |
| 123 | S | CH | O | 0 | 0 | 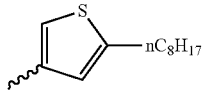 | 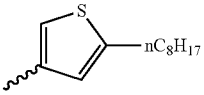 | — | — |
| 124 | S | CH | O | 0 | 0 | 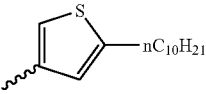 | 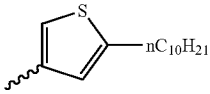 | — | — |
| 125 | S | CH | O | 0 | 0 | 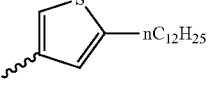 | 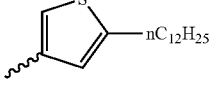 | — | — |
| 126 | S | CH | O | 0 | 0 |  |  | — | — |
| 127 | S | CH | O | 0 | 0 | 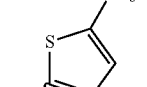 | 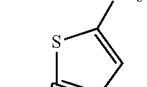 | — | — |
| 128 | S | CH | O | 0 | 0 | 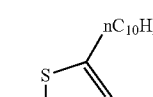 | 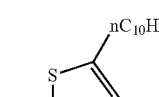 | — | — |
| 129 | S | CH | O | 0 | 0 | 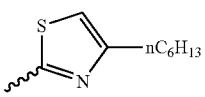 | 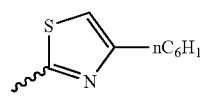 | — | — |
| 130 | S | CH | O | 0 | 0 | 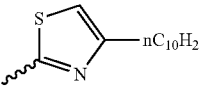 | 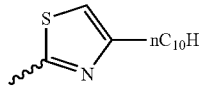 | — | — |
| 131 | S | CH | O | 0 | 0 | 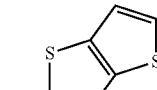 | 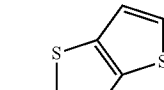 | — | — |
| 132 | S | CH | O | 0 | 0 | 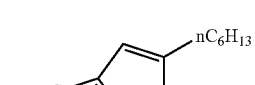 | 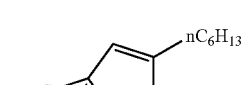 | — | — |
| 133 | S | CH | O | 0 | 0 | 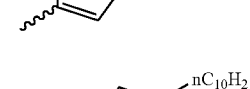 |  | — | — |

US 10,651,400 B2
31                                                                                              32
TABLE 7-continued
| 134 | S | CH | O | 0 | 0 | 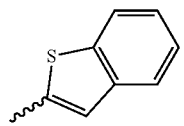 | 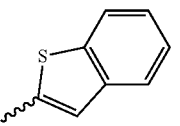 | — | — |
| 135 | S | CH | O | 0 | 0 | 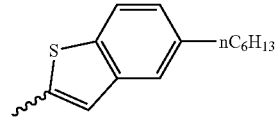 | 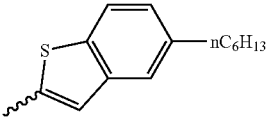 | — | — |
| 136 | S | CH | O | 0 | 0 | 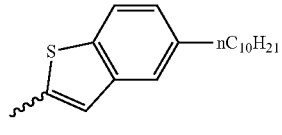 | 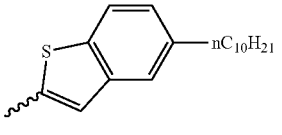 | — | — |
| 137 | S | CH | O | 0 | 0 | 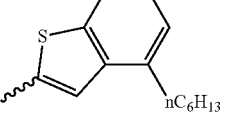 | 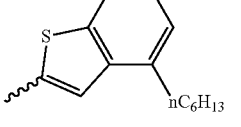 | — | — |
| 138 | S | CH | O | 0 | 0 | 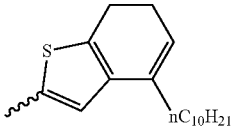 | 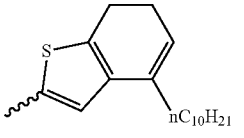 | — | — |
| 139 | S | CH | O | 0 | 0 | 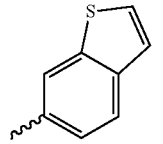 | 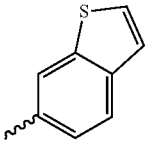 | — | — |
| 140 | S | CH | O | 0 | 0 | 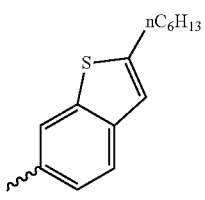 | 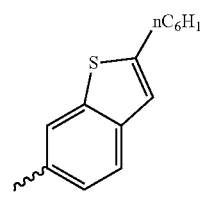 | — | — |
TABLE 8
| 141 | S | CH | O | 0 | 0 | 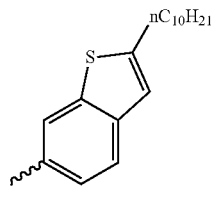 | 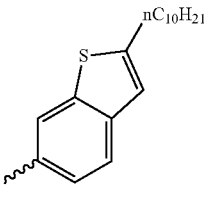 | — | — |
| 142 | S | CH | O | 0 | 0 | 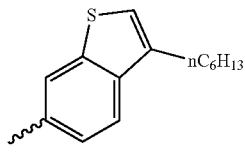 | 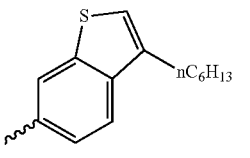 | — | — |

TABLE 8-continued
| | | | | | | | | | |
|---|---|---|---|---|---|---|---|---|---|
| 143 | S | CH | O | 0 | 0 | 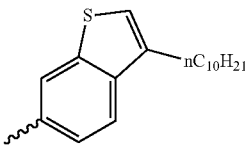 | 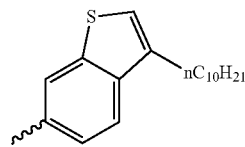 | — | — |
| 144 | S | CH | O | 0 | 0 | 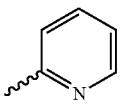 | 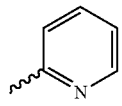 | — | — |
| 145 | S | CH | O | 0 | 0 | 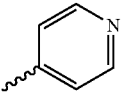 | 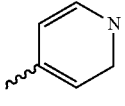 | — | — |
| 146 | S | CH | O | 0 | 0 | 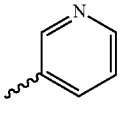 | 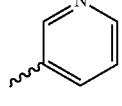 | — | — |
| 147 | S | CH | O | 0 | 0 | 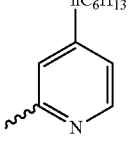 | 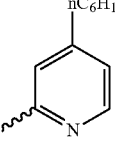 | — | — |
| 148 | S | CH | O | 0 | 0 | 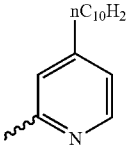 | 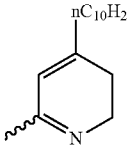 | — | — |
| 149 | S | CH | O | 0 | 0 | 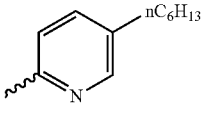 | 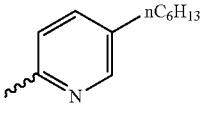 | — | — |
| 150 | S | CH | O | 0 | 0 | 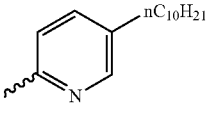 | 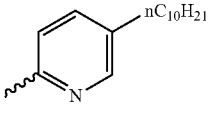 | — | — |
| 151 | S | CH | O | 0 | 0 | 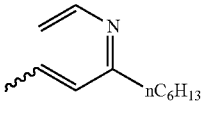 | 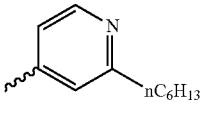 | — | — |
| 152 | S | CH | O | 0 | 0 | 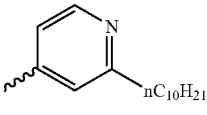 | 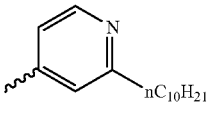 | — | — |
| 153 | S | CH | O | 0 | 0 | 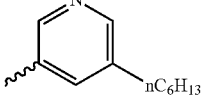 | 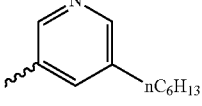 | — | — |
| 154 | S | CH | O | 0 | 0 | 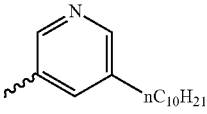 | 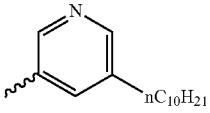 | — | — |
| 155 | S | CH | O | 2 | 2 | H | H | n-$C_6H_{13}$ | n-$C_6H_{13}$ |
| 156 | S | CH | O | 2 | 2 | H | H | n-$C_{10}H_{21}$ | n-$C_{10}H_{21}$ |
| 157 | S | CH | S | 0 | 0 | $OCH_3$ | $OCH_3$ | — | — |

TABLE 8-continued

| | | | | | | | | |
|---|---|---|---|---|---|---|---|---|
| 158 | S | CH | S | 0 | 0 | O—n-$C_4H_9$ | O—n-$C_4H_9$ | — — |
| 159 | S | CH | S | 0 | 0 | O—n-$C_5H_{11}$ | O—n-$C_5H_{11}$ | — — |
| 160 | S | CH | S | 0 | 0 | O—n-$C_6H_{13}$ | O—n-$C_6H_{13}$ | — — |

TABLE 9

| | | | | | | | | |
|---|---|---|---|---|---|---|---|---|
| 161 | S | CH | S | 0 | 0 | O—n-$C_7H_{15}$ | O—n-$C_7H_{15}$ | — — |
| 162 | S | CH | S | 0 | 0 | O—n-$C_8H_{17}$ | O—n-$C_8H_{17}$ | — — |
| 163 | S | CH | S | 0 | 0 | O—n-$C_9H_{19}$ | O—n-$C_9H_{19}$ | — — |
| 164 | S | CH | S | 0 | 0 | O—n-$C_{10}H_{21}$ | O—n-$C_{10}H_{21}$ | — — |
| 165 | S | CH | S | 0 | 0 | O—n-$C_{11}H_{23}$ | O—n-$C_{11}H_{23}$ | — — |
| 166 | S | CH | S | 0 | 0 | O—n-$C_{12}H_{25}$ | O—n-$C_{12}H_{25}$ | — — |
| 167 | S | CH | S | 0 | 0 | (2-ethylhexyloxy) | (2-ethylhexyloxy) | — — |
| 168 | S | CH | S | 0 | 0 | (propenyl) | (propenyl) | — — |
| 169 | S | CH | S | 0 | 0 | (ethynyl) | (ethynyl) | — — |
| 170 | S | CH | S | 0 | 0 | (triisopropylsilylethynyl) | (triisopropylsilylethynyl) | — — |
| 171 | S | CH | S | 0 | 0 | (phenyl) | (phenyl) | — — |
| 172 | S | CH | S | 0 | 0 | (3-$nC_6H_{13}$-phenyl) | (3-$nC_6H_{13}$-phenyl) | — — |
| 173 | S | CH | S | 0 | 0 | (3-$nC_{10}H_{21}$-phenyl) | (3-$nC_{10}H_{21}$-phenyl) | — — |
| 174 | S | CH | S | 0 | 0 | (3-(2-ethylhexyl)benzyl) | (3-(2-ethylhexyl)benzyl) | — — |
| 175 | S | CH | S | 0 | 0 | (4-$nC_6H_{13}$-phenyl) | (4-$nC_6H_{13}$-phenyl) | — — |

TABLE 9-continued

| | | | | | Ar1 | Ar2 | | |
|---|---|---|---|---|---|---|---|---|
| 176 | S | CH | S | 0 | 0 | 4-nC10H21-phenyl | 4-nC10H21-phenyl | — | — |
| 177 | S | CH | S | 0 | 0 | 3,5-di(nC6H13)-phenyl | 3,5-di(nC6H13)-phenyl | — | — |
| 178 | S | CH | S | 0 | 0 | 3,5-di(nC10H21)-phenyl | 3,5-di(nC10H21)-phenyl | — | — |
| 179 | S | CH | S | 0 | 0 | furan-2-yl | furan-2-yl | — | — |
| 180 | S | CH | S | 0 | 0 | 5-nC6H13-furan-2-yl | 5-nC6H13-furan-2-yl | — | — |

TABLE 10

| 181 | S | CH | S | 0 | 0 | 5-nC10H21-furan-2-yl | 5-nC10H21-furan-2-yl | — | — |
|---|---|---|---|---|---|---|---|---|---|
| 182 | S | CH | S | 0 | 0 | 4-nC6H13-furan-2-yl | 4-nC6H13-furan-2-yl | — | — |
| 183 | S | CH | S | 0 | 0 | 4-nC10H21-furan-2-yl | 4-nC10H21-furan-2-yl | — | — |
| 184 | S | CH | S | 0 | 0 | 1H-pyrrol-2-yl | 1H-pyrrol-2-yl | — | — |
| 185 | S | CH | S | 0 | 0 | 1-methyl-5-nC6H13-pyrrol-2-yl | 1-methyl-5-nC6H13-pyrrol-2-yl | — | — |
| 186 | S | CH | S | 0 | 0 | 1-nC6H13-pyrrol-2-yl | 1-nC6H13-pyrrol-2-yl | — | — |

TABLE 10-continued
| | | | | | | | | | |
|---|---|---|---|---|---|---|---|---|---|
| 187 | S | CH | S | 0 | 0 | 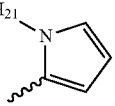 | 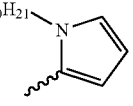 | — | — |
| 188 | S | CH | S | 0 | 0 | 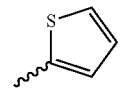 | 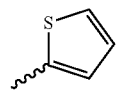 | — | — |
| 189 | S | CH | S | 0 | 0 | 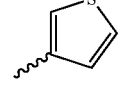 | 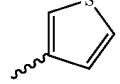 | — | — |
| 190 | S | CH | S | 0 | 0 | 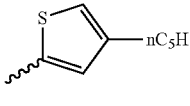 | 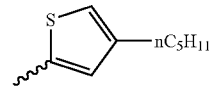 | — | — |
| 191 | S | CH | S | 0 | 0 | 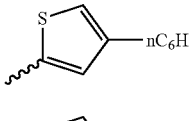 | 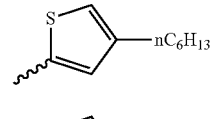 | — | — |
| 192 | S | CH | S | 0 | 0 | 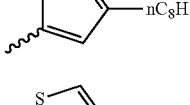 | 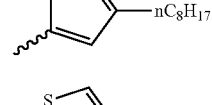 | — | — |
| 193 | S | CH | S | 0 | 0 | 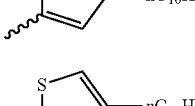 | 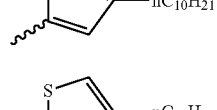 | — | — |
| 194 | S | CH | S | 0 | 0 | 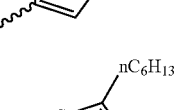 | 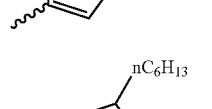 | — | — |
| 195 | S | CH | S | 0 | 0 | 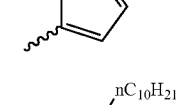 | 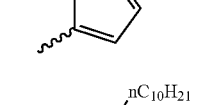 | — | — |
| 196 | S | CH | S | 0 | 0 | 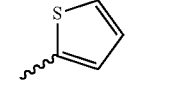 | 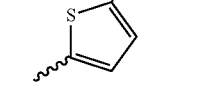 | — | — |
| 197 | S | CH | S | 0 | 0 | 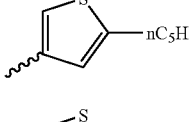 | 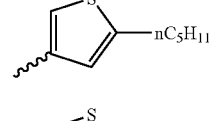 | — | — |
| 198 | S | CH | S | 0 | 0 | 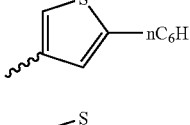 | 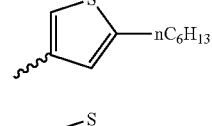 | — | — |
| 199 | S | CH | S | 0 | 0 | 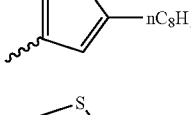 | 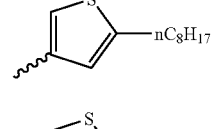 | — | — |
| 200 | S | CH | S | 0 | 0 |  | 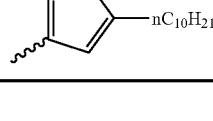 | — | — |

TABLE 11

| 201 | S | CH | S | 0 | 0 | 2-(nC₁₂H₂₅)-thiophen-5-yl | 2-(nC₁₂H₂₅)-thiophen-5-yl | — | — |
| 202 | S | CH | S | 0 | 0 | thiazol-2-yl | thiazol-2-yl | — | — |
| 203 | S | CH | S | 0 | 0 | 5-(nC₆H₁₃)-thiazol-2-yl | 5-(nC₆H₁₃)-thiazol-2-yl | — | — |
| 204 | S | CH | S | 0 | 0 | 5-(nC₁₀H₂₁)-thiazol-2-yl | 5-(nC₁₀H₂₁)-thiazol-2-yl | — | — |
| 205 | S | CH | S | 0 | 0 | 4-(nC₆H₁₃)-thiazol-2-yl | 4-(nC₆H₁₃)-thiazol-2-yl | — | — |
| 206 | S | CH | S | 0 | 0 | 4-(nC₁₀H₂₁)-thiazol-2-yl | 4-(nC₁₀H₂₁)-thiazol-2-yl | — | — |
| 207 | S | CH | S | 0 | 0 | thieno[3,2-b]thiophen-2-yl | thieno[3,2-b]thiophen-2-yl | — | — |
| 208 | S | CH | S | 0 | 0 | 5-(nC₆H₁₃)-thieno[3,2-b]thiophen-2-yl | 5-(nC₆H₁₃)-thieno[3,2-b]thiophen-2-yl | — | — |
| 209 | S | CH | S | 0 | 0 | 5-(nC₁₀H₂₁)-thieno[3,2-b]thiophen-2-yl | 5-(nC₁₀H₂₁)-thieno[3,2-b]thiophen-2-yl | — | — |
| 210 | S | CH | S | 0 | 0 | benzo[b]thiophen-2-yl | benzo[b]thiophen-2-yl | — | — |
| 211 | S | CH | S | 0 | 0 | 5-(nC₆H₁₃)-benzo[b]thiophen-2-yl | 5-(nC₆H₁₃)-benzo[b]thiophen-2-yl | — | — |
| 212 | S | CH | S | 0 | 0 | 5-(nC₁₀H₂₁)-benzo[b]thiophen-2-yl | 5-(nC₁₀H₂₁)-benzo[b]thiophen-2-yl | — | — |

TABLE 11-continued

| | | | | | | | | |
|---|---|---|---|---|---|---|---|---|
| 213 | S | CH | S | 0 | 0 | benzothiophene-2-yl, 4-nC$_6$H$_{13}$ | benzothiophene-2-yl, 4-nC$_6$H$_{13}$ | — — |
| 214 | S | CH | S | 0 | 0 | benzothiophene-2-yl, 4-nC$_{10}$H$_{21}$ | benzothiophene-2-yl, 4-nC$_{10}$H$_{21}$ | — — |
| 215 | S | CH | S | 0 | 0 | benzothiophene-6-yl | benzothiophene-6-yl | — — |
| 216 | S | CH | S | 0 | 0 | benzothiophene-6-yl, 2-nC$_6$H$_{13}$ | benzothiophene-6-yl, 2-nC$_6$H$_{13}$ | — — |
| 217 | S | CH | S | 0 | 0 | benzothiophene-6-yl, 2-nC$_{10}$H$_{21}$ | benzothiophene-6-yl, 2-nC$_{10}$H$_{21}$ | — — |
| 218 | S | CH | S | 0 | 0 | benzothiophene-6-yl, 3-nC$_6$H$_{13}$ | benzothiophene-6-yl, 3-nC$_6$H$_{13}$ | — — |
| 219 | S | CH | S | 0 | 0 | benzothiophene-6-yl, 3-nC$_{10}$H$_{21}$ | benzothiophene-6-yl, 3-nC$_{10}$H$_{21}$ | — — |
| 220 | S | CH | S | 0 | 0 | pyridin-2-yl | pyridin-2-yl | — — |

TABLE 12

| | | | | | | | | |
|---|---|---|---|---|---|---|---|---|
| 221 | S | CH | S | 0 | 0 | pyridin-4-yl | pyridin-4-yl | — — |
| 222 | S | CH | S | 0 | 0 | pyridin-3-yl | pyridin-3-yl | — — |

TABLE 12-continued
| | | | | | | | | | |
|---|---|---|---|---|---|---|---|---|---|
| 223 | S | CH | S | 0 | 0 | 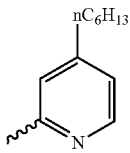 | 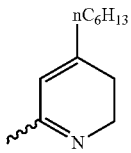 | — | — |
| 224 | S | CH | S | 0 | 0 | 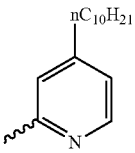 | 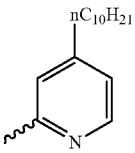 | — | — |
| 225 | S | CH | S | 0 | 0 | 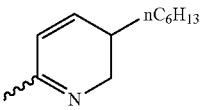 | 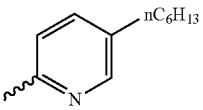 | — | — |
| 226 | S | CH | S | 0 | 0 | 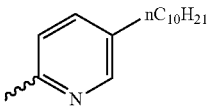 | 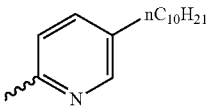 | — | — |
| 227 | S | CH | S | 0 | 0 | 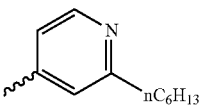 | 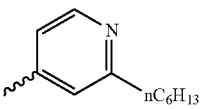 | — | — |
| 228 | S | CH | S | 0 | 0 | 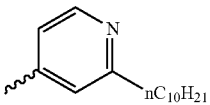 | 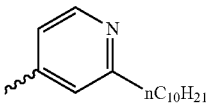 | — | — |
| 229 | S | CH | S | 0 | 0 | 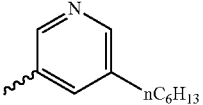 | 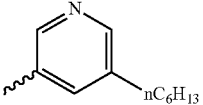 | — | — |
| 230 | S | CH | S | 0 | 0 | 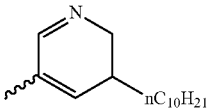 | 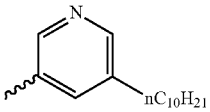 | — | — |
| 231 | S | S | CH | 0 | 0 | $CH_3$ | $CH_3$ | — | — |
| 232 | S | S | CH | 0 | 0 | $n\text{-}C_4H_9$ | $n\text{-}C_4H_9$ | — | — |
| 233 | S | S | CH | 0 | 0 | $n\text{-}C_5H_{11}$ | $n\text{-}C_5H_{11}$ | — | — |
| 234 | S | S | CH | 0 | 0 | $n\text{-}C_6H_{13}$ | $n\text{-}C_6H_{13}$ | — | — |
| 235 | S | S | CH | 0 | 0 | $n\text{-}C_7H_{15}$ | $n\text{-}C_7H_{15}$ | — | — |
| 236 | S | S | CH | 0 | 0 | $n\text{-}C_8H_{17}$ | $n\text{-}C_8H_{17}$ | — | — |
| 237 | S | S | CH | 0 | 0 | $n\text{-}C_9H_{19}$ | $n\text{-}C_9H_{19}$ | — | — |
| 238 | S | S | CH | 0 | 0 | $n\text{-}C_{10}H_{21}$ | $n\text{-}C_{10}H_{21}$ | — | — |
| 239 | S | S | CH | 0 | 0 | $n\text{-}C_{11}H_{23}$ | $n\text{-}C_{11}H_{23}$ | — | — |
| 240 | S | S | CH | 0 | 0 | $n\text{-}C_{12}H_{25}$ | $n\text{-}C_{12}H_{25}$ | — | — |
TABLE 13
| | | | | | | | | | |
|---|---|---|---|---|---|---|---|---|---|
| 241 | S | S | CH | 0 | 0 | 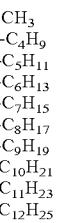 | 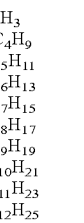 | — | — |
| 242 | S | S | CH | 0 | 0 |  |  | — | — |

TABLE 13-continued
| 243 | S | S | CH | 0 | 0 | 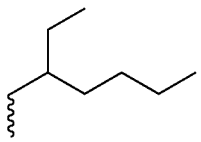 | 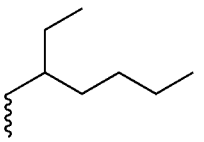 | — | — |
| 244 | S | S | CH | 0 | 0 |  | 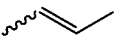 | — | — |
| 245 | S | S | CH | 0 | 0 |  |  | — | — |
| 246 | S | S | CH | 0 | 0 | 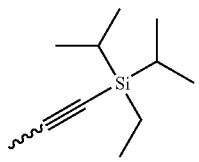 | 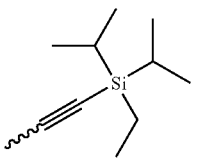 | — | — |
| 247 | S | S | CH | 0 | 0 | 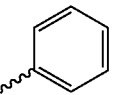 | 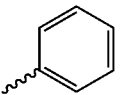 | — | — |
| 248 | S | S | CH | 0 | 0 | 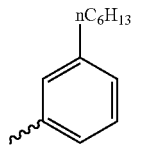 | 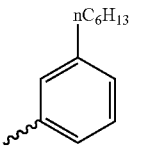 | — | — |
| 249 | S | S | CH | 0 | 0 | 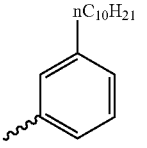 | 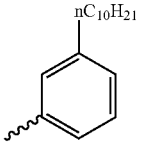 | — | — |
| 250 | S | S | CH | 0 | 0 | 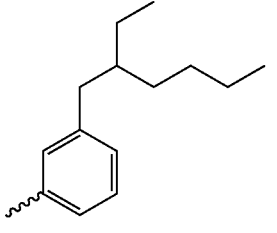 | 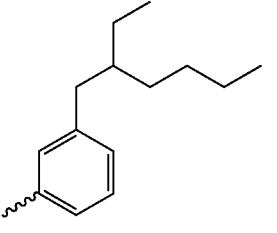 | — | — |
| 251 | S | S | CH | 0 | 0 | 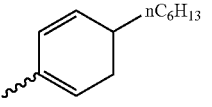 | 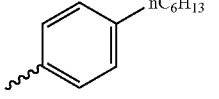 | — | — |
| 252 | S | S | CH | 0 | 0 | 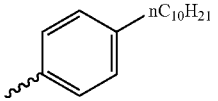 | 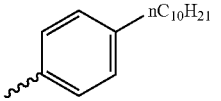 | — | — |
| 253 | S | S | CH | 0 | 0 | 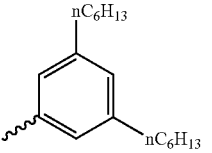 | 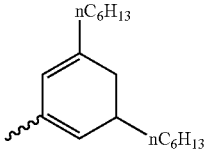 | — | — |

TABLE 13-continued
| 254 | S | S | CH | 0 | 0 | 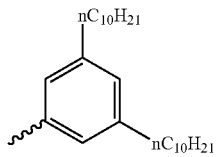 | 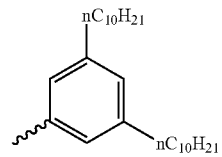 | — | — |
| 255 | S | S | CH | 0 | 0 | 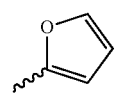 | 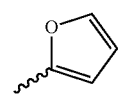 | — | — |
| 256 | S | S | CH | 0 | 0 | 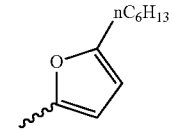 | 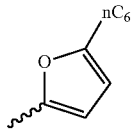 | — | — |
| 257 | S | S | CH | 0 | 0 | 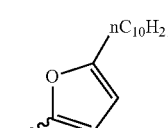 | 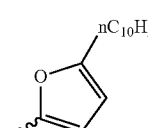 | — | — |
| 258 | S | S | CH | 0 | 0 | 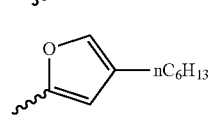 | 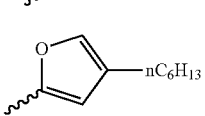 | — | — |
| 259 | S | S | CH | 0 | 0 | 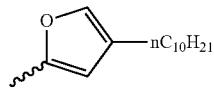 | 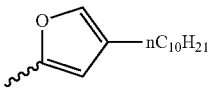 | — | — |
| 260 | S | S | CH | 0 | 0 | 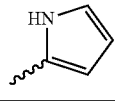 | 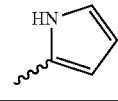 | — | — |
TABLE 14
| 261 | S | S | CH | 0 | 0 | 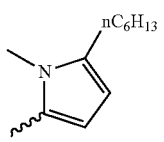 | 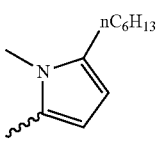 | — | — |
| 262 | S | S | CH | 0 | 0 | 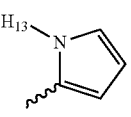 | 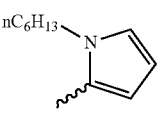 | — | — |
| 263 | S | S | CH | 0 | 0 | 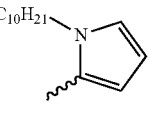 | 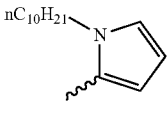 | — | — |
| 264 | S | S | CH | 0 | 0 | 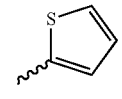 | 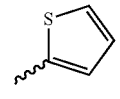 | — | — |
| 265 | S | S | CH | 0 | 0 | 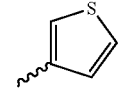 | 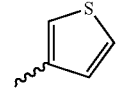 | — | — |

TABLE 14-continued
| | | | | | | | | | |
|---|---|---|---|---|---|---|---|---|---|
| 266 | S | S | CH | 0 | 0 | 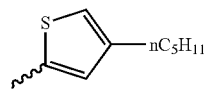 | 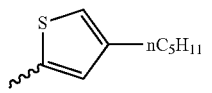 | — | — |
| 267 | S | S | CH | 0 | 0 | 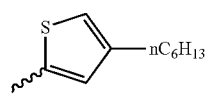 | 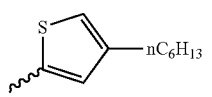 | — | — |
| 268 | S | S | CH | 0 | 0 | 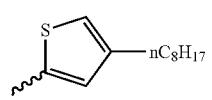 | 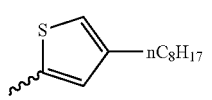 | — | — |
| 269 | S | S | CH | 0 | 0 | 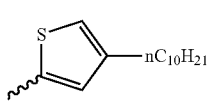 | 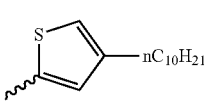 | — | — |
| 270 | S | S | CH | 0 | 0 | 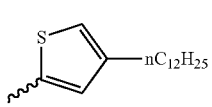 | 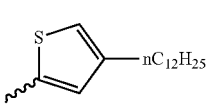 | — | — |
| 271 | S | S | CH | 0 | 0 | 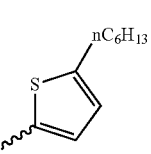 | 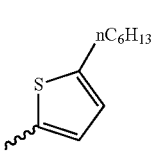 | — | — |
| 272 | S | S | CH | 0 | 0 | 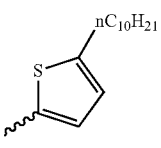 | 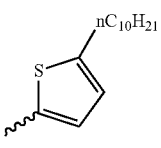 | — | — |
| 273 | S | S | CH | 0 | 0 | 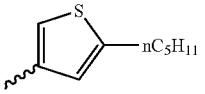 | 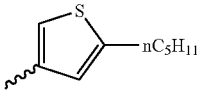 | — | — |
| 274 | S | S | CH | 0 | 0 | 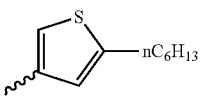 | 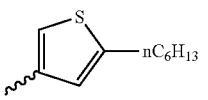 | — | — |
| 275 | S | S | CH | 0 | 0 | 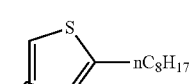 | 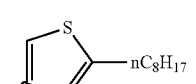 | — | — |
| 276 | S | S | CH | 0 | 0 | 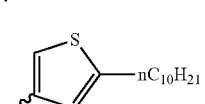 | 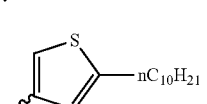 | — | — |
| 277 | S | S | CH | 0 | 0 | 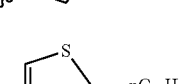 | 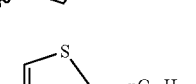 | — | — |
| 278 | S | S | CH | 0 | 0 | 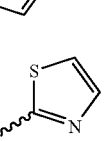 | 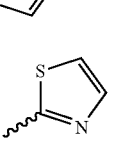 | — | — |
| 279 | S | S | CH | 0 | 0 | 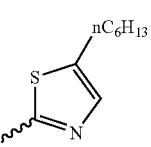 | 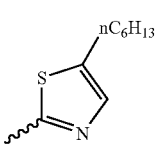 | — | — |

TABLE 14-continued
| 280 | S | S | CH | 0 | 0 | 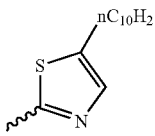 | 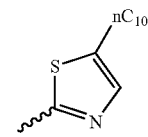 | — | — |
TABLE 15
| 281 | S | S | CH | 0 | 0 | 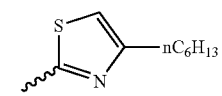 | 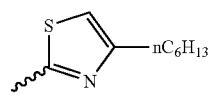 | — | — |
| 282 | S | S | CH | 0 | 0 | 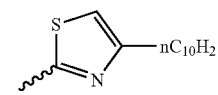 | 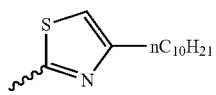 | — | — |
| 283 | S | S | CH | 0 | 0 | 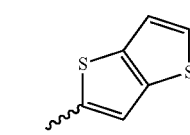 | 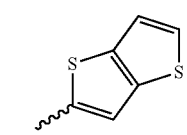 | — | — |
| 284 | S | S | CH | 0 | 0 | 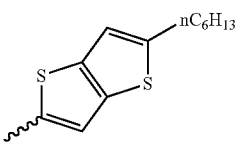 | 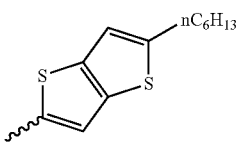 | — | — |
| 285 | S | S | CH | 0 | 0 | 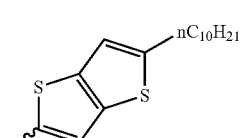 | 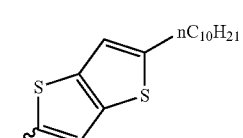 | — | — |
| 286 | S | S | CH | 0 | 0 | 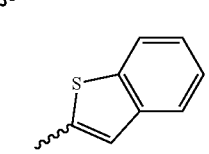 | 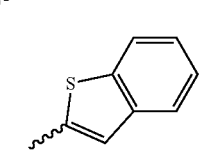 | — | — |
| 287 | S | S | CH | 0 | 0 | 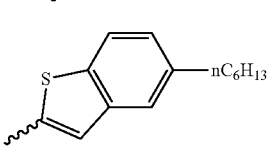 | 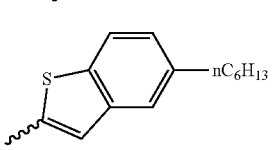 | — | — |
| 288 | S | S | CH | 0 | 0 | 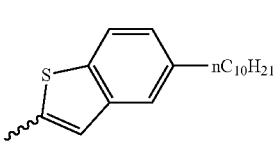 | 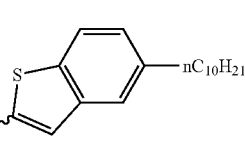 | — | — |
| 289 | S | S | CH | 0 | 0 | 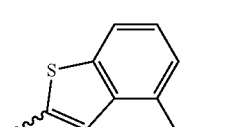 | 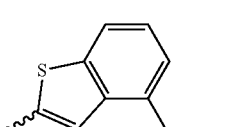 | — | — |
| 290 | S | S | CH | 0 | 0 | 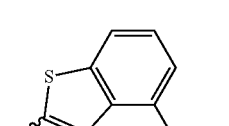 | 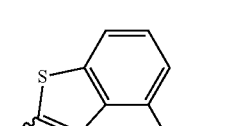 | — | — |

TABLE 15-continued
| 291 | S | S | CH | 0 | 0 | 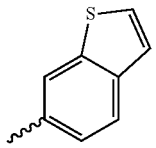 | 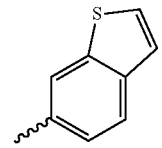 | — | — |
| 292 | S | S | CH | 0 | 0 | 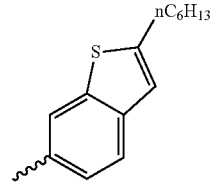 | 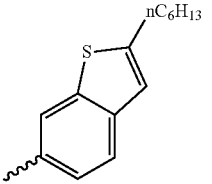 | — | — |
| 293 | S | S | CH | 0 | 0 | 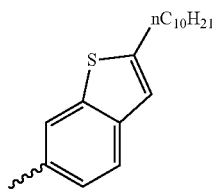 | 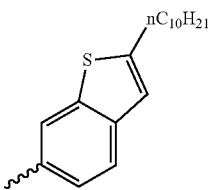 | — | — |
| 294 | S | S | CH | 0 | 0 | 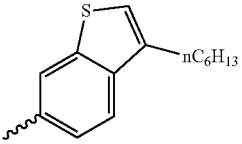 | 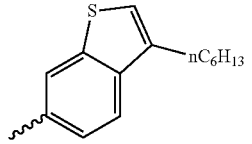 | — | — |
| 295 | S | S | CH | 0 | 0 | 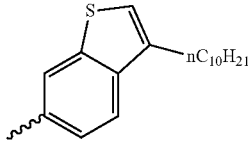 | 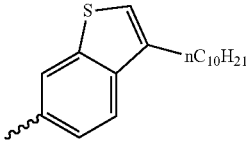 | — | — |
| 296 | S | S | CH | 0 | 0 | 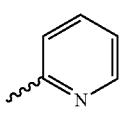 | 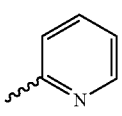 | — | — |
| 297 | S | S | CH | 0 | 0 | 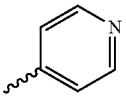 | 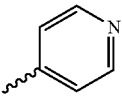 | — | — |
| 298 | S | S | CH | 0 | 0 | 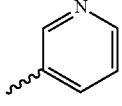 | 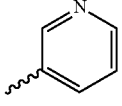 | — | — |
| 299 | S | S | CH | 0 | 0 | 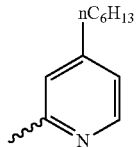 | 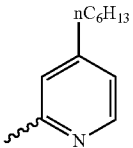 | — | — |
| 300 | S | S | CH | 0 | 0 | 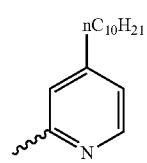 | 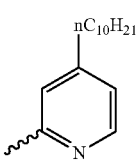 | — | — |

TABLE 16
| | | | | | | | | |
|---|---|---|---|---|---|---|---|---|
| 301 | S | S | CH | 0 | 0 | 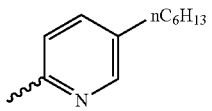 | 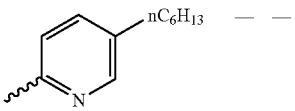 | — — |
| 302 | S | S | CH | 0 | 0 | 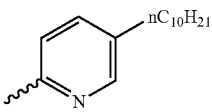 | 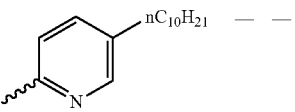 | — — |
| 303 | S | S | CH | 0 | 0 | 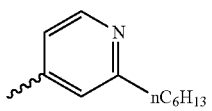 | 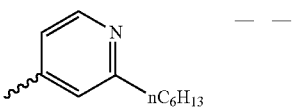 | — — |
| 304 | S | S | CH | 0 | 0 | 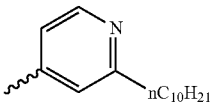 | 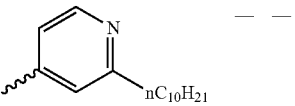 | — — |
| 305 | S | S | CH | 0 | 0 | 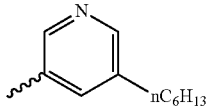 | 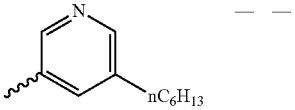 | — — |
| 306 | S | S | CH | 0 | 0 | 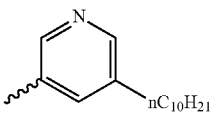 | 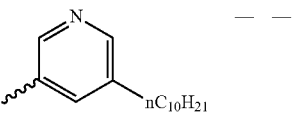 | — — |
| 307 | S | O | CH | 0 | 0 | $CH_3$ | $CH_3$ | — — |
| 308 | S | O | CH | 0 | 0 | n-$C_4H_9$ | n-$C_4H_9$ | — — |
| 309 | S | O | CH | 0 | 0 | n-$C_5H_{11}$ | n-$C_5H_{11}$ | — — |
| 310 | S | O | CH | 0 | 0 | n-$C_6H_{13}$ | n-$C_6H_{13}$ | — — |
| 311 | S | O | CH | 0 | 0 | n-$C_7H_{15}$ | n-$C_7H_{15}$ | — — |
| 312 | S | O | CH | 0 | 0 | n-$C_8H_{17}$ | n-$C_8H_{17}$ | — — |
| 313 | S | O | CH | 0 | 0 | n-$C_9H_{19}$ | n-$C_9H_{19}$ | — — |
| 314 | S | O | CH | 0 | 0 | n-$C_{10}H_{21}$ | n-$C_{10}H_{21}$ | — — |
| 315 | S | O | CH | 0 | 0 | n-$C_{11}H_{23}$ | n-$C_{11}H_{23}$ | — — |
| 316 | S | O | CH | 0 | 0 | n-$C_{12}H_{25}$ | n-$C_{12}H_{25}$ | — — |
| 317 | S | O | CH | 0 | 0 | 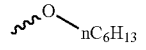 | 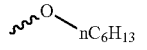 | — — |
| 318 | S | O | CH | 0 | 0 | 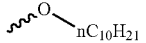 | 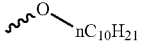 | — — |
| 319 | S | O | CH | 0 | 0 |  |  | — — |
| 320 | S | O | CH | 0 | 0 | 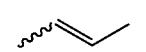 | 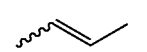 | — — |
TABLE 17
| | | | | | | | | |
|---|---|---|---|---|---|---|---|---|
| 321 | S | O | CH | 0 | 0 |  |  | — — |

TABLE 17-continued

| | | | | | | | | | |
|---|---|---|---|---|---|---|---|---|---|
| 322 | S | O | CH | 0 | 0 | triisopropylsilyl-alkyne | triisopropylsilyl-alkyne | — | — |
| 323 | S | O | CH | 0 | 0 | phenyl | phenyl | — | — |
| 324 | S | O | CH | 0 | 0 | 3-nC6H13-cyclohexadienyl | 3-nC6H13-phenyl | — | — |
| 325 | S | O | CH | 0 | 0 | 3-nC10H21-cyclohexadienyl | 3-nC10H21-phenyl | — | — |
| 326 | S | O | CH | 0 | 0 | 3-(2-ethylhexyl)phenyl | 3-(2-ethylhexyl)cyclohexadienyl | — | — |
| 327 | S | O | CH | 0 | 0 | 4-nC6H13-phenyl | 4-nC6H13-phenyl | — | — |
| 328 | S | O | CH | 0 | 0 | 4-nC10H21-phenyl | 4-nC10H21-phenyl | — | — |
| 329 | S | O | CH | 0 | 0 | 3,5-di-nC6H13-phenyl | 3,5-di-nC6H13-phenyl | — | — |
| 330 | S | O | CH | 0 | 0 | 3,5-di-nC10H21-phenyl | 3,5-di-nC10H21-cyclohexadienyl | — | — |
| 331 | S | O | CH | 0 | 0 | furan-2-yl | furan-2-yl | — | — |

TABLE 17-continued

| 332 | S | O | CH | 0 | 0 | 5-nC6H13-furan-2-yl | 5-nC6H13-furan-2-yl | — | — |
| 333 | S | O | CH | 0 | 0 | 5-nC10H21-furan-2-yl | 5-nC10H21-furan-2-yl | — | — |
| 334 | S | O | CH | 0 | 0 | 4-nC6H13-furan-2-yl | 4-nC6H13-furan-2-yl | — | — |
| 335 | S | O | CH | 0 | 0 | 4-nC10H21-furan-2-yl | 4-nC10H21-furan-2-yl | — | — |
| 336 | S | O | CH | 0 | 0 | 1H-pyrrol-2-yl | 1H-pyrrol-2-yl | — | — |
| 337 | S | O | CH | 0 | 0 | 1-methyl-5-nC6H13-pyrrol-2-yl | 1-methyl-5-nC6H13-pyrrol-2-yl | — | — |
| 338 | S | O | CH | 0 | 0 | 1-nC6H13-pyrrol-2-yl | 1-nC6H13-pyrrol-2-yl | — | — |
| 339 | S | O | CH | 0 | 0 | 1-nC10H21-pyrrol-2-yl | 1-nC10H21-pyrrol-2-yl | — | — |
| 340 | S | O | CH | 0 | 0 | thiophen-2-yl | thiophen-2-yl | — | — |

TABLE 18

| 341 | S | O | CH | 0 | 0 | thiophen-3-yl | thiophen-3-yl | — | — |
| 342 | S | O | CH | 0 | 0 | 4-nC5H11-thiophen-2-yl | 4-nC5H11-thiophen-2-yl | — | — |
| 343 | S | O | CH | 0 | 0 | 4-nC6H13-thiophen-2-yl | 4-nC6H13-thiophen-2-yl | — | — |
| 344 | S | O | CH | 0 | 0 | 4-nC8H17-thiophen-2-yl | 4-nC8H17-thiophen-2-yl | — | — |

TABLE 18-continued

| | | | | | | | | | |
|---|---|---|---|---|---|---|---|---|---|
| 345 | S | O | CH | 0 | 0 | thiophene-nC₁₀H₂₁ | thiophene-nC₁₀H₂₁ | — | — |
| 346 | S | O | CH | 0 | 0 | thiophene-nC₁₂H₂₅ | thiophene-nC₁₂H₂₅ | — | — |
| 347 | S | O | CH | 0 | 0 | thiophene-nC₆H₁₃ | thiophene-nC₆H₁₃ | — | — |
| 348 | S | O | CH | 0 | 0 | thiophene-nC₁₀H₂₁ | thiophene-nC₁₀H₂₁ | — | — |
| 349 | S | O | CH | 0 | 0 | thiophene-nC₅H₁₁ | thiophene-nC₅H₁₁ | — | — |
| 350 | S | O | CH | 0 | 0 | thiophene-nC₆H₁₃ | thiophene-nC₆H₁₃ | — | — |
| 351 | S | O | CH | 0 | 0 | thiophene-nC₈H₁₇ | thiophene-nC₈H₁₇ | — | — |
| 352 | S | O | CH | 0 | 0 | thiophene-nC₁₀H₂₁ | thiophene-nC₁₀H₂₁ | — | — |
| 353 | S | O | CH | 0 | 0 | thiophene-nC₁₂H₂₅ | thiophene-nC₁₂H₂₅ | — | — |
| 354 | S | O | CH | 0 | 0 | thiazole | thiazole | — | — |
| 355 | S | O | CH | 0 | 0 | thiazole-nC₆H₁₃ | thiazole-nC₆H₁₃ | — | — |
| 356 | S | O | CH | 0 | 0 | thiazole-nC₁₀H₂₁ | thiazole-nC₁₀H₂₁ | — | — |
| 357 | S | O | CH | 0 | 0 | thiazole-nC₆H₁₃ | thiazole-nC₆H₁₃ | — | — |

TABLE 18-continued

| 358 | S | O | CH | 0 | 0 | thiazole-nC10H21 | thiazole-nC10H21 | — | — |
| 359 | S | O | CH | 0 | 0 | thienothiophene | thienothiophene | — | — |
| 360 | S | O | CH | 0 | 0 | thienothiophene-nC6H13 | thienothiophene-nC6H13 | — | — |

TABLE 19

| 361 | S | O | CH | 0 | 0 | thienothiophene-nC10H21 | thienothiophene-nC10H21 | — | — |
| 362 | S | O | CH | 0 | 0 | benzothiophene | benzothiophene | — | — |
| 363 | S | O | CH | 0 | 0 | benzothiophene-nC6H13 | benzothiophene-nC6H13 | — | — |
| 364 | S | O | CH | 0 | 0 | benzothiophene-nC10H21 | benzothiophene-nC10H21 | — | — |
| 365 | S | O | CH | 0 | 0 | benzothiophene-nC6H13 | benzothiophene-nC6H13 | — | — |
| 366 | S | O | CH | 0 | 0 | benzothiophene-nC10H21 | benzothiophene-nC10H21 | — | — |
| 367 | S | O | CH | 0 | 0 | benzothiophene | benzothiophene | — | — |

TABLE 19-continued
| 368 | S | O | CH | 0 | 0 | 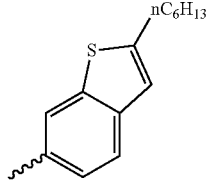 | 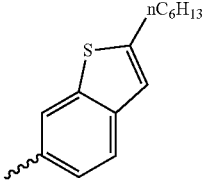 | — | — |
| 369 | S | O | CH | 0 | 0 | 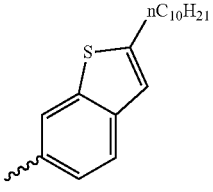 | 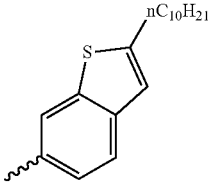 | — | — |
| 370 | S | O | CH | 0 | 0 | 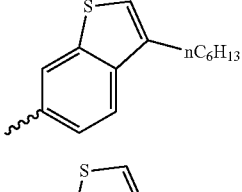 | 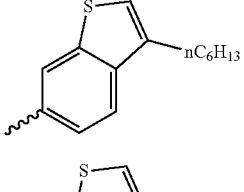 | — | — |
| 371 | S | O | CH | 0 | 0 | 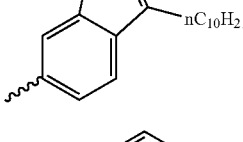 | 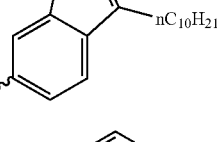 | — | — |
| 372 | S | O | CH | 0 | 0 | 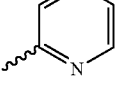 | 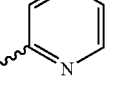 | — | — |
| 373 | S | O | CH | 0 | 0 | 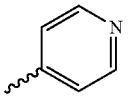 | 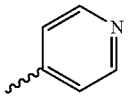 | — | — |
| 374 | S | O | CH | 0 | 0 | 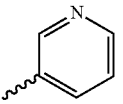 | 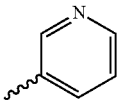 | — | — |
| 375 | S | O | CH | 0 | 0 | 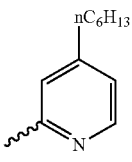 | 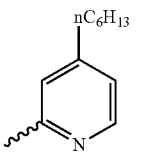 | — | — |
| 376 | S | O | CH | 0 | 0 | 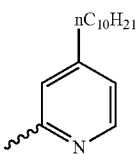 | 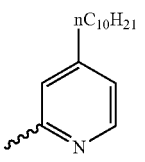 | — | — |
| 377 | S | O | CH | 0 | 0 | 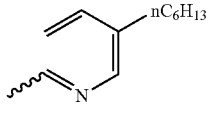 | 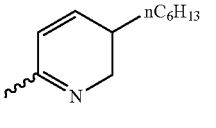 | — | — |
| 378 | S | O | CH | 0 | 0 | 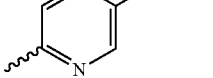 | 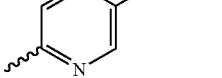 | — | — |

TABLE 19-continued
| | | | | | | | | | |
|---|---|---|---|---|---|---|---|---|---|
| 379 | S | O | CH | 0 | 0 | 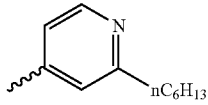 | 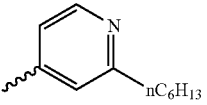 | — | — |
| 380 | S | O | CH | 0 | 0 | 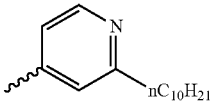 | 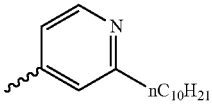 | — | — |
TABLE 20
| | | | | | | | | | |
|---|---|---|---|---|---|---|---|---|---|
| 381 | S | O | CH | 0 | 0 | 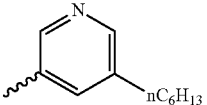 | 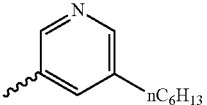 | — | — |
| 382 | S | O | CH | 0 | 0 | 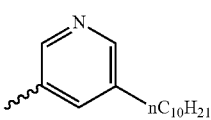 | 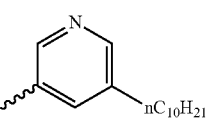 | — | — |
| 383 | S | S | N | 0 | 0 | $CH_3$ | $CH_3$ | — | — |
| 384 | S | S | N | 0 | 0 | $n\text{-}C_4H_9$ | $n\text{-}C_4H_9$ | — | — |
| 385 | S | S | N | 0 | 0 | $n\text{-}C_5H_{11}$ | $n\text{-}C_5H_{11}$ | — | — |
| 386 | S | S | N | 0 | 0 | $n\text{-}C_6H_{13}$ | $n\text{-}C_6H_{13}$ | — | — |
| 387 | S | S | N | 0 | 0 | $n\text{-}C_7H_{15}$ | $n\text{-}C_7H_{15}$ | — | — |
| 388 | S | S | N | 0 | 0 | $n\text{-}C_8H_{17}$ | $n\text{-}C_8H_{17}$ | — | — |
| 389 | S | S | N | 0 | 0 | $n\text{-}C_9H_{19}$ | $n\text{-}C_9H_{19}$ | — | — |
| 390 | S | S | N | 0 | 0 | $n\text{-}C_{10}H_{21}$ | $n\text{-}C_{10}H_{21}$ | — | — |
| 391 | S | S | N | 0 | 0 | $n\text{-}C_{11}H_{23}$ | $n\text{-}C_{11}H_{23}$ | — | — |
| 392 | S | S | N | 0 | 0 | $n\text{-}C_{12}H_{25}$ | $n\text{-}C_{12}H_{25}$ | — | — |
| 393 | S | S | N | 0 | 0 | 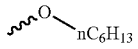 | 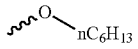 | — | — |
| 394 | S | S | N | 0 | 0 | 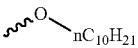 | 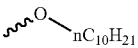 | — | — |
| 395 | S | S | N | 0 | 0 | 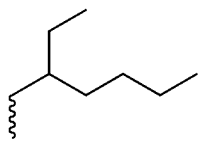 | 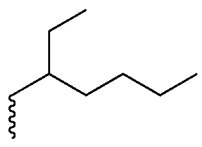 | — | — |
| 396 | S | S | N | 0 | 0 | 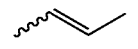 | 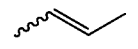 | — | — |
| 397 | S | S | N | 0 | 0 |  |  | — | — |
| 398 | S | S | N | 0 | 0 | 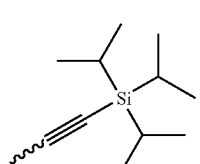 | 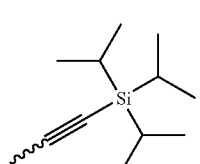 | — | — |
| 399 | S | S | N | 0 | 0 | 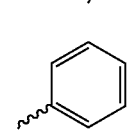 | 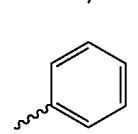 | — | — |

TABLE 20-continued
| 400 | S | S | N | 0 | 0 | 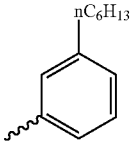 | 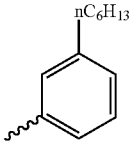 | — | — |
TABLE 21
| 401 | S | S | N | 0 | 0 | 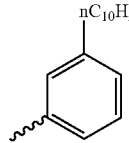 | 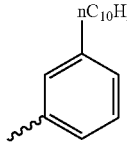 | — | — |
| 402 | S | S | N | 0 | 0 | 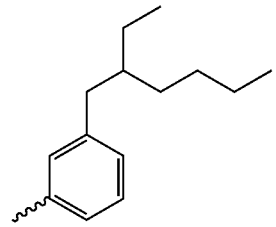 | 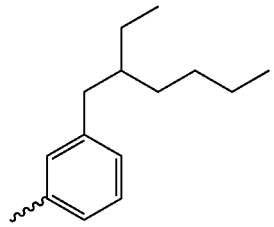 | — | — |
| 403 | S | S | N | 0 | 0 | 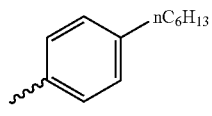 | 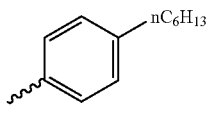 | — | — |
| 404 | S | S | N | 0 | 0 | 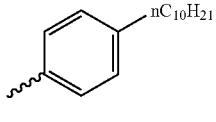 | 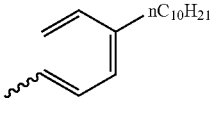 | — | — |
| 405 | S | S | N | 0 | 0 | 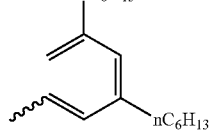 | 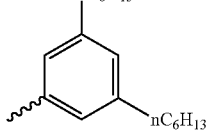 | — | — |
| 406 | S | S | N | 0 | 0 | 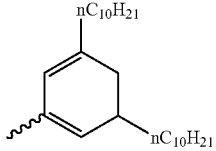 | 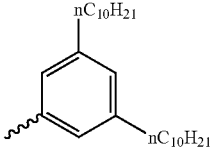 | — | — |
| 407 | S | S | N | 0 | 0 | 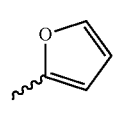 | 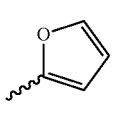 | — | — |
| 408 | S | S | N | 0 | 0 | 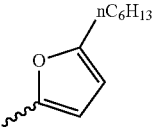 | 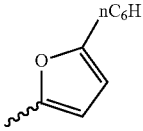 | — | — |
| 409 | S | S | N | 0 | 0 | 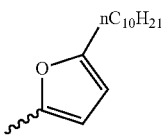 | 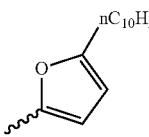 | — | — |

TABLE 21-continued
| 410 | S | S | N | 0 | 0 | 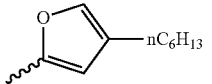 | 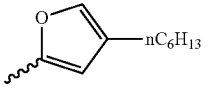 | — | — |
| 411 | S | S | N | 0 | 0 | 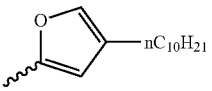 | 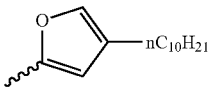 | — | — |
| 412 | S | S | N | 0 | 0 | 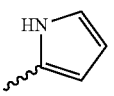 | 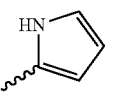 | — | — |
| 413 | S | S | N | 0 | 0 | 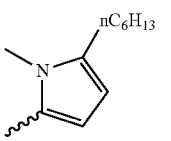 | 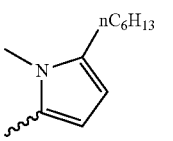 | — | — |
| 414 | S | S | N | 0 | 0 | 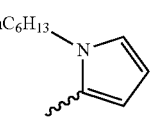 | 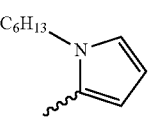 | — | — |
| 415 | S | S | N | 0 | 0 | 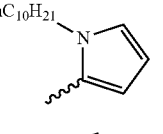 | 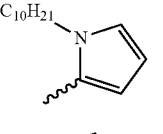 | — | — |
| 416 | S | S | N | 0 | 0 | 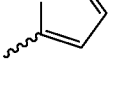 | 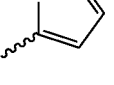 | — | — |
| 417 | S | S | N | 0 | 0 | 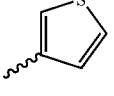 | 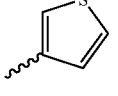 | — | — |
| 418 | S | S | N | 0 | 0 | 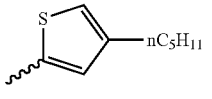 | 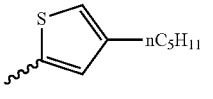 | — | — |
| 419 | S | S | N | 0 | 0 | 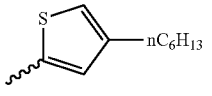 | 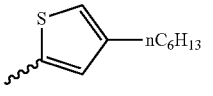 | — | — |
| 420 | S | S | N | 0 | 0 | 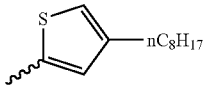 | 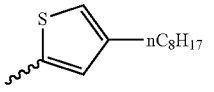 | — | — |
TABLE 22
| 421 | S | S | N | 0 | 0 | 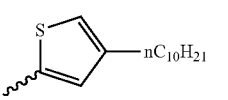 | 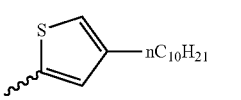 | — | — |
| 422 | S | S | N | 0 | 0 | 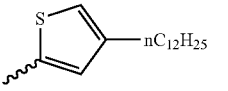 | 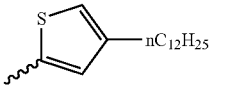 | — | — |

TABLE 22-continued
| 423 | S | S | N | 0 | 0 | 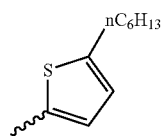 | 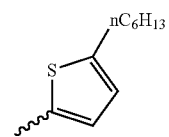 | — | — |
| 424 | S | S | N | 0 | 0 | 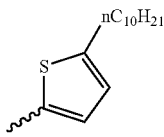 | 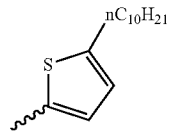 | — | — |
| 425 | S | S | N | 0 | 0 | 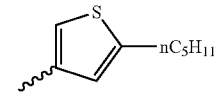 | 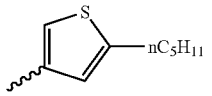 | — | — |
| 426 | S | S | N | 0 | 0 | 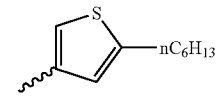 | 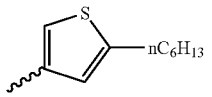 | — | — |
| 427 | S | S | N | 0 | 0 | 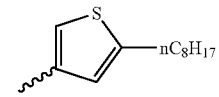 | 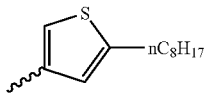 | — | — |
| 428 | S | S | N | 0 | 0 | 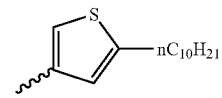 | 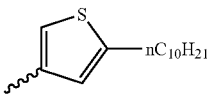 | — | — |
| 429 | S | S | N | 0 | 0 | 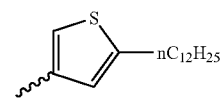 | 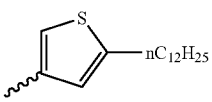 | — | — |
| 430 | S | S | N | 0 | 0 | 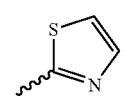 | 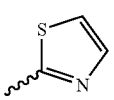 | — | — |
| 431 | S | S | N | 0 | 0 | 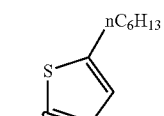 | 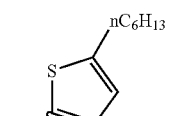 | — | — |
| 432 | S | S | N | 0 | 0 | 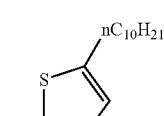 | 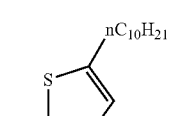 | — | — |
| 433 | S | S | N | 0 | 0 | 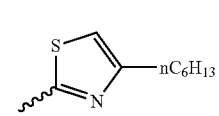 | 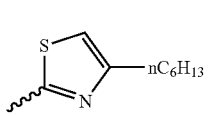 | — | — |
| 434 | S | S | N | 0 | 0 | 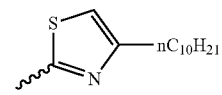 | 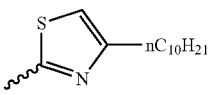 | — | — |
| 435 | S | S | N | 0 | 0 | 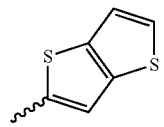 | 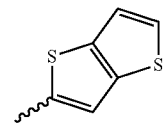 | — | — |

TABLE 22-continued

| 436 | S | S | N | 0 | 0 | thieno[3,2-b]thiophene-nC6H13 | thieno[3,2-b]thiophene-nC6H13 | — | — |
| 437 | S | S | N | 0 | 0 | thieno[3,2-b]thiophene-nC10H21 | thieno[3,2-b]thiophene-nC10H21 | — | — |
| 438 | S | S | N | 0 | 0 | benzothiophene | benzothiophene | — | — |
| 439 | S | S | N | 0 | 0 | benzothiophene-nC6H13 | benzothiophene-nC6H13 | — | — |
| 440 | S | S | N | 0 | 0 | benzothiophene-nC10H21 | benzothiophene-nC10H21 | — | — |

TABLE 23

| 441 | S | S | N | 0 | 0 | benzothiophene-nC6H13 | benzothiophene-nC6H13 | — | — |
| 442 | S | S | N | 0 | 0 | benzothiophene-nC10H21 | benzothiophene-nC10H21 | — | — |
| 443 | S | S | N | 0 | 0 | benzothiophene | benzothiophene | — | — |
| 444 | S | S | N | 0 | 0 | benzothiophene-nC6H13 | benzothiophene-nC6H13 | — | — |

TABLE 23-continued
| 445 | S | S | N | 0 | 0 | 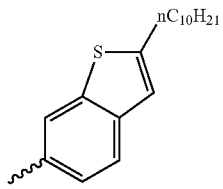 | 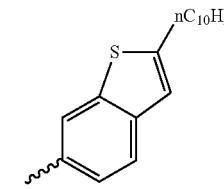 | — | — |
| 446 | S | S | N | 0 | 0 | 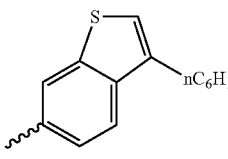 | 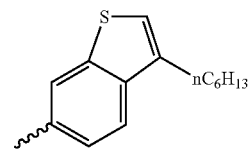 | — | — |
| 447 | S | S | N | 0 | 0 | 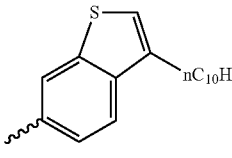 | 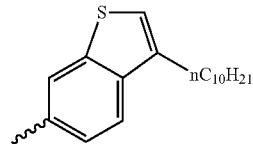 | — | — |
| 448 | S | S | N | 0 | 0 | 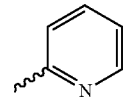 | 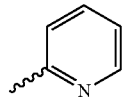 | — | — |
| 449 | S | S | N | 0 | 0 | 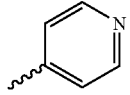 | 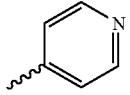 | — | — |
| 450 | S | S | N | 0 | 0 | 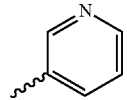 | 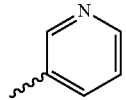 | — | — |
| 451 | S | S | N | 0 | 0 | 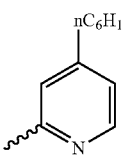 | 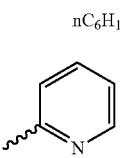 | — | — |
| 452 | S | S | N | 0 | 0 | 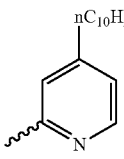 | 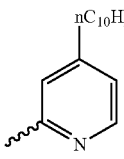 | — | — |
| 453 | S | S | N | 0 | 0 | 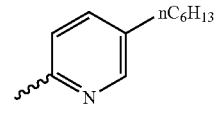 | 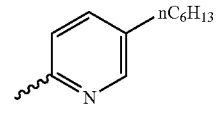 | — | — |
| 454 | S | S | N | 0 | 0 | 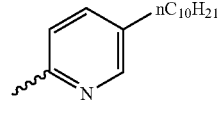 | 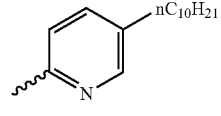 | — | — |
| 455 | S | S | N | 0 | 0 | 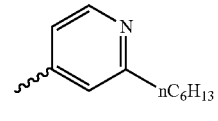 | 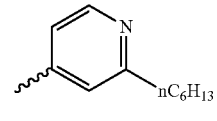 | — | — |

TABLE 23-continued
| 456 | S | S | N | 0 | 0 | 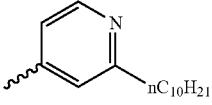 | 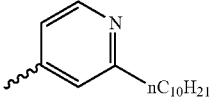 | — | — |
| 457 | S | S | N | 0 | 0 | 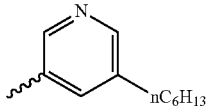 | 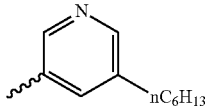 | — | — |
| 458 | S | S | N | 0 | 0 | 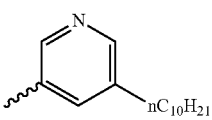 | 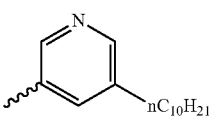 | — | — |
| 459 | S | O | S | 0 | 0 | $CH_3$ | $CH_3$ | — | — |
| 460 | S | O | S | 0 | 0 | n-$C_4H_9$ | n-$C_4H_9$ | — | — |
TABLE 24
| 461 | S | O | S | 0 | 0 | n-$C_5H_{11}$ | n-$C_5H_{11}$ | — | — |
| 462 | S | O | S | 0 | 0 | n-$C_6H_{13}$ | n-$C_6H_{13}$ | — | — |
| 463 | S | O | S | 0 | 0 | n-$C_7H_{15}$ | n-$C_7H_{15}$ | — | — |
| 464 | S | O | S | 0 | 0 | n-$C_8H_{17}$ | n-$C_8H_{17}$ | — | — |
| 465 | S | O | S | 0 | 0 | n-$C_9H_{19}$ | n-$C_9H_{19}$ | — | — |
| 466 | S | O | S | 0 | 0 | n-$C_{10}H_{21}$ | n-$C_{10}H_{21}$ | — | — |
| 467 | S | O | S | 0 | 0 | n-$C_{11}H_{23}$ | n-$C_{11}H_{23}$ | — | — |
| 468 | S | O | S | 0 | 0 | n-$C_{12}H_{25}$ | n-$C_{12}H_{25}$ | — | — |
| 469 | S | O | S | 0 | 0 | 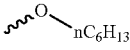 | 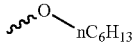 | — | — |
| 470 | S | O | S | 0 | 0 | 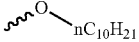 | 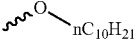 | — | — |
| 471 | S | O | S | 0 | 0 | 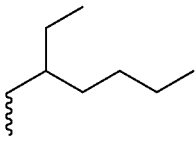 | 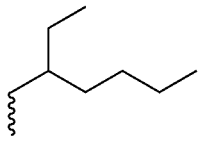 | — | — |
| 472 | S | O | S | 0 | 0 | 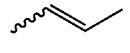 | 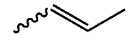 | — | — |
| 473 | S | O | S | 0 | 0 |  |  | — | — |
| 474 | S | O | S | 0 | 0 | 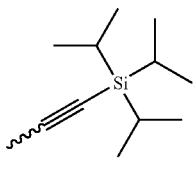 | 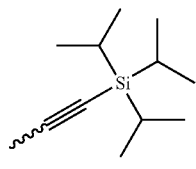 | — | — |
| 475 | S | O | S | 0 | 0 | 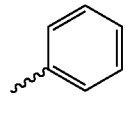 | 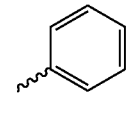 | — | — |
| 476 | S | O | S | 0 | 0 | 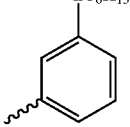 | 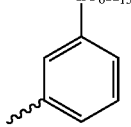 | — | — |

TABLE 24-continued

| 477 | S | O | S | 0 | 0 | 3-(nC10H21)-phenyl | 3-(nC10H21)-phenyl | — | — |
| 478 | S | O | S | 0 | 0 | 3-(2-ethylhexyl)-phenyl | 3-(2-ethylhexyl)-phenyl | — | — |
| 479 | S | O | S | 0 | 0 | 4-(nC6H13)-phenyl | 4-(nC6H13)-phenyl | — | — |
| 480 | S | O | S | 0 | 0 | 4-(nC10H21)-phenyl | 4-(nC10H21)-phenyl | — | — |

TABLE 25

| 481 | S | O | S | 0 | 0 | 2,4-bis(nC6H13)-butadienyl | 3,5-bis(nC6H13)-phenyl | — | — |
| 482 | S | O | S | 0 | 0 | 3,5-bis(nC10H21)-phenyl | 3,5-bis(nC10H21)-phenyl | — | — |
| 483 | S | O | S | 0 | 0 | 2-furyl | 2-furyl | — | — |
| 484 | S | O | S | 0 | 0 | 5-(nC6H13)-2-furyl | 5-(nC6H13)-2-furyl | — | — |
| 485 | S | O | S | 0 | 0 | 5-(nC10H21)-2-furyl | 5-(nC10H21)-2-furyl | — | — |
| 486 | S | O | S | 0 | 0 | 4-(nC6H13)-2-furyl | 4-(nC6H13)-2-furyl | — | — |

TABLE 25-continued
| 487 | S | O | S | 0 | 0 | 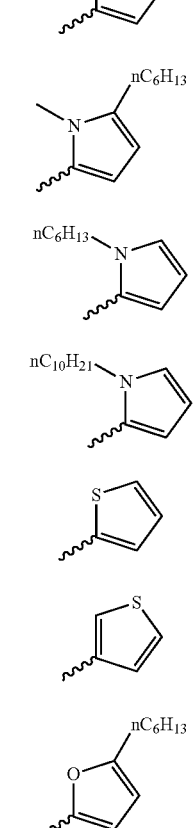 | 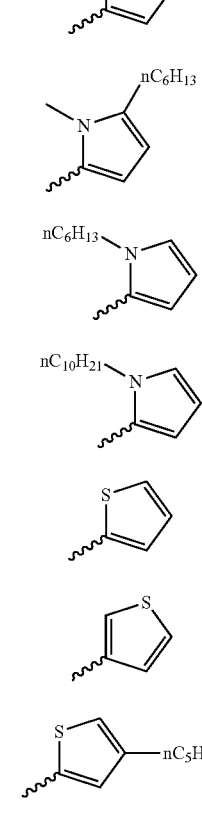 | — | — |
| 488 | S | O | S | 0 | 0 | 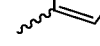 | 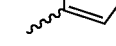 | — | — |
| 489 | S | O | S | 0 | 0 | 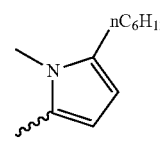 | 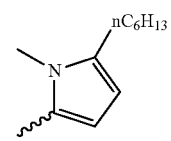 | — | — |
| 490 | S | O | S | 0 | 0 | 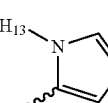 | 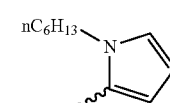 | — | — |
| 491 | S | O | S | 0 | 0 | 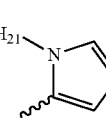 | 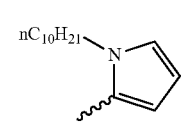 | — | — |
| 492 | S | O | S | 0 | 0 |  | 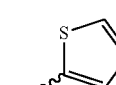 | — | — |
| 493 | S | O | S | 0 | 0 | 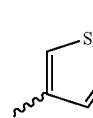 | 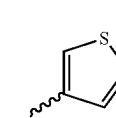 | — | — |
| 494 | S | O | S | 0 | 0 | 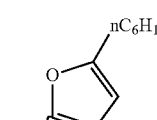 | 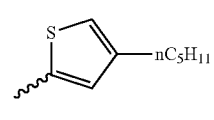 | — | — |
| 495 | S | O | S | 0 | 0 | 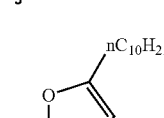 | 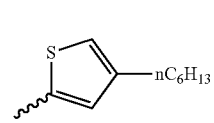 | — | — |
| 496 | S | O | S | 0 | 0 | 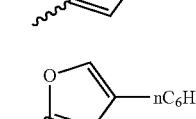 | 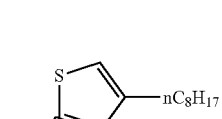 | — | — |
| 497 | S | O | S | 0 | 0 | 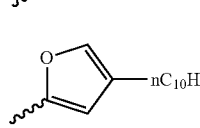 | 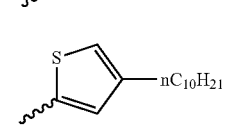 | — | — |
| 498 | S | O | S | 0 | 0 | 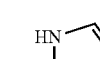 | 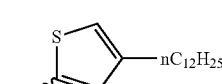 | — | — |
| 499 | S | O | S | 0 | 0 | 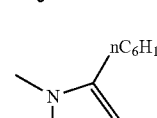 | 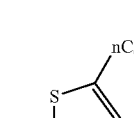 | — | — |

TABLE 25-continued
| 500 | 5 | O | S | 0 | 0 | 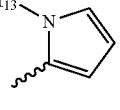 | 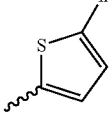 | — | — |
TABLE 26
| 501 | S | O | S | 0 | 0 | 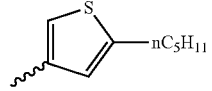 | 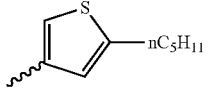 | — | — |
| 502 | S | O | S | 0 | 0 | 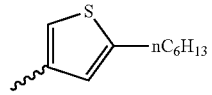 | 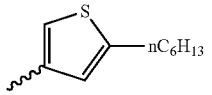 | — | — |
| 503 | S | O | S | 0 | 0 | 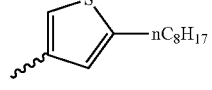 | 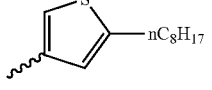 | — | — |
| 504 | S | O | S | 0 | 0 | 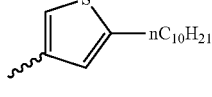 | 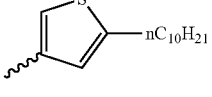 | — | — |
| 505 | S | O | S | 0 | 0 | 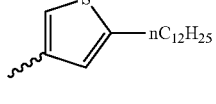 | 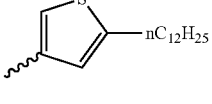 | — | — |
| 506 | S | O | S | 0 | 0 | 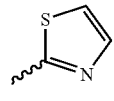 | 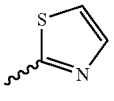 | — | — |
| 507 | S | O | S | 0 | 0 | 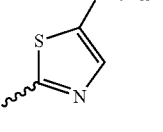 | 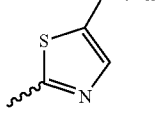 | — | — |
| 508 | S | O | S | 0 | 0 | 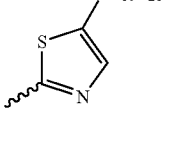 | 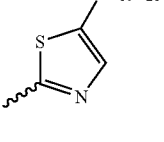 | — | — |
| 509 | S | O | S | 0 | 0 | 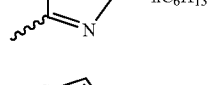 | 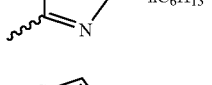 | — | — |
| 510 | S | O | S | 0 | 0 | 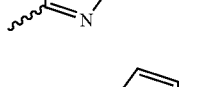 | 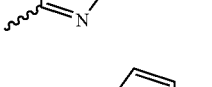 | — | — |
| 511 | S | O | S | 0 | 0 | 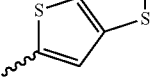 | 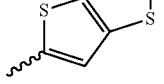 | — | — |

TABLE 26-continued
| | | | | | | | | | |
|---|---|---|---|---|---|---|---|---|---|
| 512 | S | O | S | 0 | 0 | 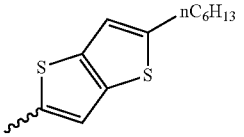 | 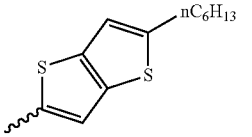 | — | — |
| 513 | S | O | S | 0 | 0 | 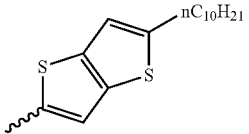 | 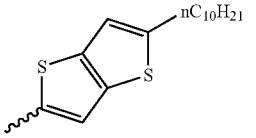 | — | — |
| 514 | S | O | S | 0 | 0 | 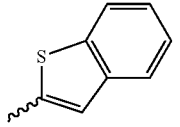 | 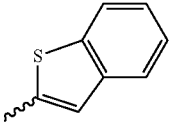 | — | — |
| 515 | S | O | S | 0 | 0 | 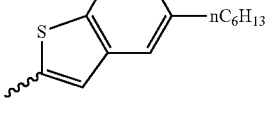 | 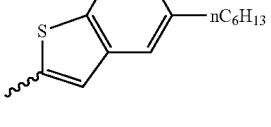 | — | — |
| 516 | S | O | S | 0 | 0 | 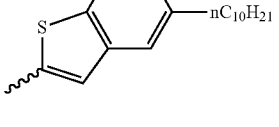 | 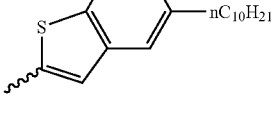 | — | — |
| 517 | S | O | S | 0 | 0 | 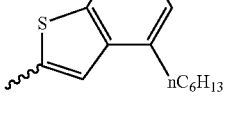 | 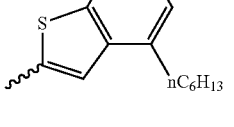 | — | — |
| 518 | S | O | S | 0 | 0 | 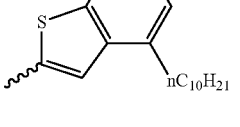 | 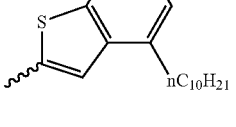 | — | — |
| 519 | S | O | S | 0 | 0 | 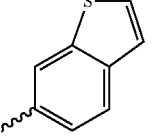 | 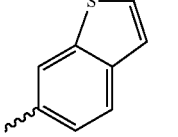 | — | — |
| 520 | S | O | S | 0 | 0 | 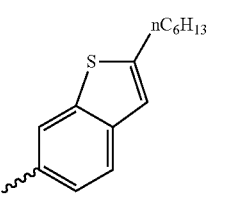 | 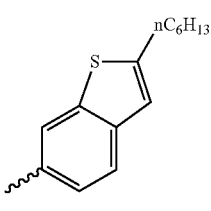 | — | — |

TABLE 27

| 521 | S | O | S | 0 | 0 | benzothiophene-2-yl-nC10H21 | benzothiophene-2-yl-nC10H21 | — | — |
| 522 | S | O | 5 | 0 | 0 | benzothiophene-3-yl-nC6H13 | benzothiophene-3-yl-nC6H13 | — | — |
| 523 | S | O | S | 0 | 0 | benzothiophene-3-yl-nC10H21 | benzothiophene-3-yl-nC10H21 | — | — |
| 524 | S | O | S | 0 | 0 | pyridin-2-yl | pyridin-2-yl | — | — |
| 525 | S | O | S | 0 | 0 | pyridin-4-yl | pyridin-4-yl | — | — |
| 526 | S | O | S | 0 | 0 | pyridin-3-yl | pyridin-3-yl | — | — |
| 527 | S | O | S | 0 | 0 | 4-nC6H13-pyridin-2-yl | 4-nC6H13-pyridin-2-yl | — | — |
| 528 | S | O | S | 0 | 0 | 4-nC10H21-pyridin-2-yl | 4-nC10H21-pyridin-2-yl | — | — |
| 529 | S | O | S | 0 | 0 | 5-nC6H13-pyridin-2-yl | 5-nC6H13-pyridin-2-yl | — | — |
| 530 | S | O | S | 0 | 0 | 5-nC10H21-pyridin-2-yl | 5-nC10H21-pyridin-2-yl | — | — |
| 531 | S | O | S | 0 | 0 | 2-nC6H13-pyridin-5-yl | 2-nC6H13-pyridin-5-yl | — | — |

TABLE 27-continued

| 532 | S | O | S | 0 | 0 | 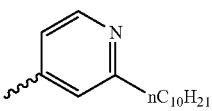 | 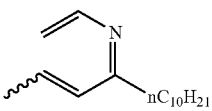 | — | — |
| 533 | S | O | S | 0 | 0 | 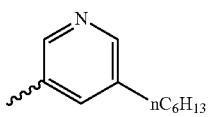 | 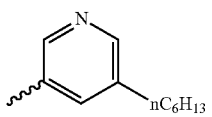 | — | — |
| 534 | S | O | S | 0 | 0 | 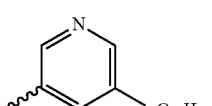 | 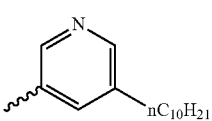 | — | — |
| 535 | Se | CH | S | 0 | 0 | $CH_3$ | $CH_3$ | — | — |
| 536 | Se | CH | S | 0 | 0 | $n\text{-}C_4H_9$ | $n\text{-}C_4H_9$ | — | — |
| 537 | Se | CH | S | 0 | 0 | $n\text{-}C_5H_{11}$ | $n\text{-}C_5H_{11}$ | — | — |
| 538 | Se | CH | S | 0 | 0 | $n\text{-}C_6H_{13}$ | $n\text{-}C_6H_{13}$ | — | — |
| 539 | Se | CH | S | 0 | 0 | $n\text{-}C_7H_{15}$ | $n\text{-}C_7H_{15}$ | — | — |
| 540 | Se | CH | S | 0 | 0 | $n\text{-}C_8H_{17}$ | $n\text{-}C_8H_{17}$ | — | — |

TABLE 28

| 541 | Se | CH | S | 0 | 0 | $n\text{-}C_9H_{19}$ | $n\text{-}C_9H_{19}$ | — | — |
| 542 | Se | CH | S | 0 | 0 | $n\text{-}C_{10}H_{21}$ | $n\text{-}C_{10}H_{21}$ | — | — |
| 543 | Se | CH | S | 0 | 0 | $n\text{-}C_{11}H_{23}$ | $n\text{-}C_{11}H_{23}$ | — | — |
| 544 | Se | OH | S | 0 | 0 | $n\text{-}C_{12}H_{25}$ | $n\text{-}C_{12}H_{25}$ | — | — |
| 545 | Se | CH | S | 0 | 0 | 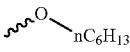 | 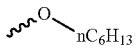 | — | — |
| 546 | Se | CH | S | 0 | 0 | 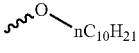 | 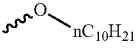 | — | — |
| 547 | Se | CH | S | 0 | 0 | 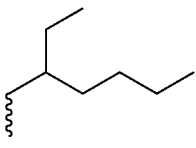 | 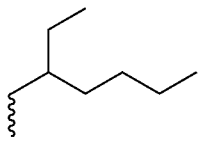 | — | — |
| 548 | Se | CH | S | 0 | 0 | 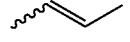 | 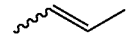 | — | — |
| 549 | Se | CH | S | 0 | 0 |  |  | — | — |
| 550 | Se | CH | S | 0 | 0 | 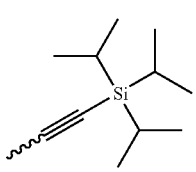 | 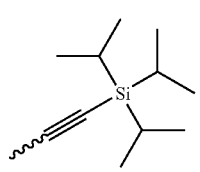 | — | — |
| 551 | Se | CH | S | 0 | 0 | 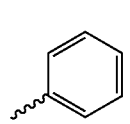 | 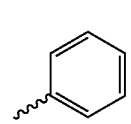 | — | — |
| 552 | Se | CH | S | 0 | 0 | 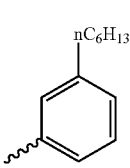 | 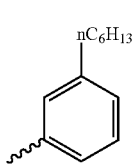 | — | — |

TABLE 28-continued
| | | | | | | | | |
|---|---|---|---|---|---|---|---|---|
| 553 | Se | CH | S | 0 0 | 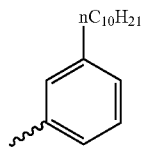 | 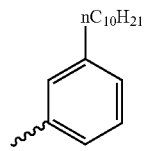 | — | — |
| 554 | Se | CH | S | 0 0 | 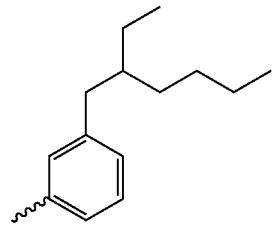 | 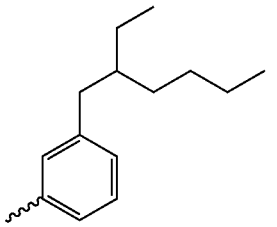 | — | — |
| 555 | Se | CH | S | 0 0 | 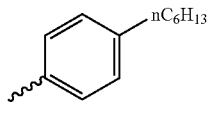 | 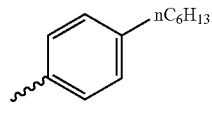 | — | — |
| 556 | Se | CH | S | 0 0 | 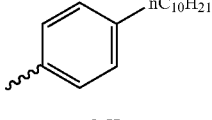 | 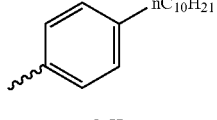 | — | — |
| 557 | Se | CH | S | 0 0 | 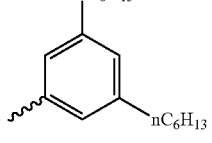 | 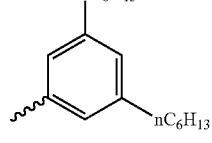 | — | — |
| 558 | Se | CH | S | 0 0 | 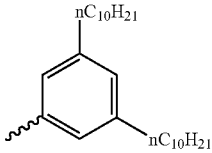 | 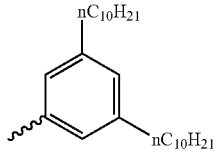 | — | — |
| 559 | Se | CH | S | 0 0 | 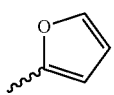 | 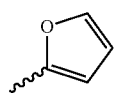 | — | — |
| 560 | Se | CH | S | 0 0 | 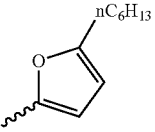 | 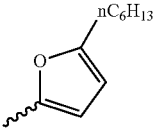 | — | — |
TABLE 29
| | | | | | | | | |
|---|---|---|---|---|---|---|---|---|
| 561 | Se | CH | S | 0 0 | 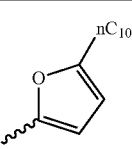 | 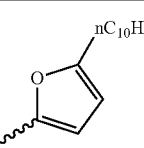 | — | — |
| 562 | Se | CH | S | 0 0 | 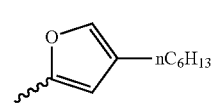 | 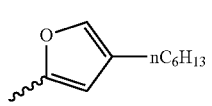 | — | — |

TABLE 29-continued
| 563 | Se | CH | S | 0 | 0 | 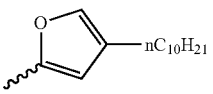 | 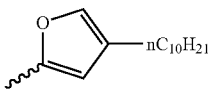 | — | — |
| 564 | Se | CH | S | 0 | 0 | 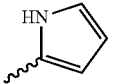 | 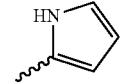 | — | — |
| 565 | Se | CH | S | 0 | 0 | 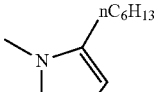 | 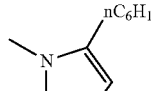 | — | — |
| 566 | Se | CH | S | 0 | 0 | 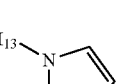 | 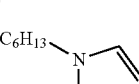 | — | — |
| 567 | Se | CH | S | 0 | 0 | 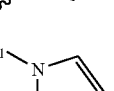 | 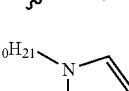 | — | — |
| 568 | Se | CH | S | 0 | 0 | 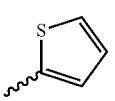 | 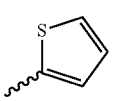 | — | — |
| 569 | Se | CH | S | 0 | 0 | 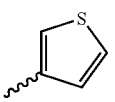 | 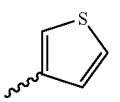 | — | — |
| 570 | Se | CH | S | 0 | 0 | 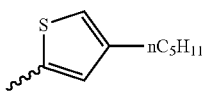 | 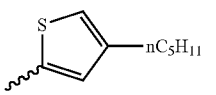 | — | — |
| 571 | Se | CH | S | 0 | 0 | 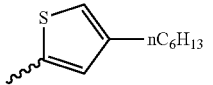 | 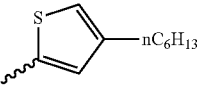 | — | — |
| 572 | Se | CH | S | 0 | 0 | 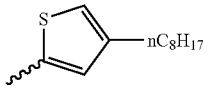 | 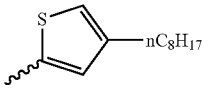 | — | — |
| 573 | Se | CH | S | 0 | 0 | 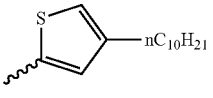 | 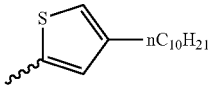 | — | — |
| 574 | Se | CH | S | 0 | 0 | 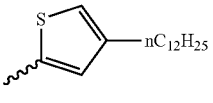 | 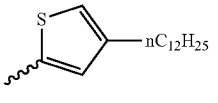 | — | — |
| 575 | Se | CH | S | 0 | 0 | 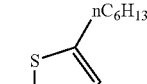 | 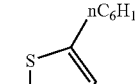 | — | — |
| 576 | Se | CH | S | 0 | 0 | 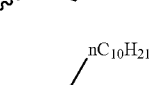 | 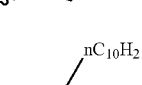 | — | — |

TABLE 29-continued
| 577 | Se | CH | S | 0 | 0 | 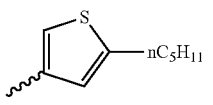 | 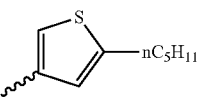 | — | — |
| 578 | Se | CH | S | 0 | 0 | 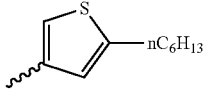 | 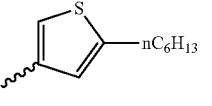 | — | — |
| 579 | Se | CH | S | 0 | 0 | 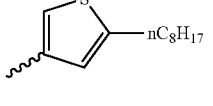 | 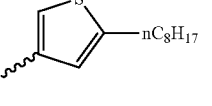 | — | — |
| 580 | Se | CH | S | 0 | 0 | 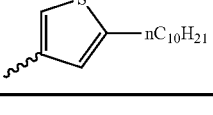 | 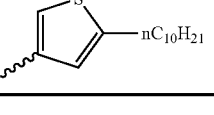 | — | — |
TABLE 30
| 581 | Se | CH | S | 0 | 0 | 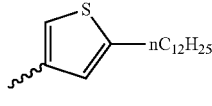 | 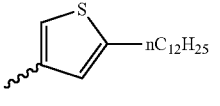 | — | — |
| 582 | Se | CH | S | 0 | 0 | 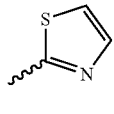 | 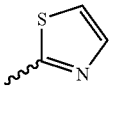 | — | — |
| 583 | Se | CH | S | 0 | 0 | 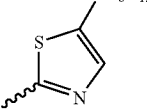 | 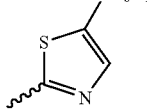 | — | — |
| 584 | Se | CH | S | 0 | 0 | 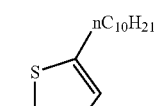 | 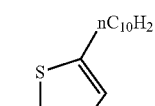 | — | — |
| 585 | Se | CH | S | 0 | 0 | 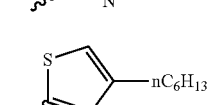 | 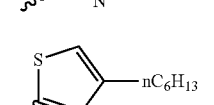 | — | — |
| 586 | Se | CH | S | 0 | 0 | 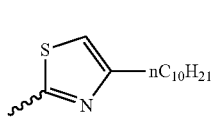 | 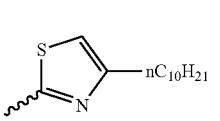 | — | — |
| 587 | Se | CH | S | 0 | 0 | 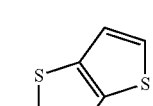 | 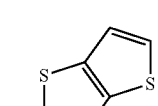 | — | — |
| 588 | Se | OH | S | 0 | 0 | 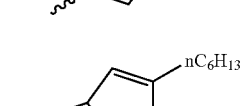 | 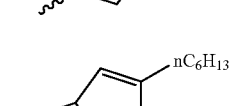 | — | — |

TABLE 30-continued

| | | | | | | | |
|---|---|---|---|---|---|---|---|
| 589 | Se | CH | S | 0 0 | (thienothiophene-nC₁₀H₂₁) | (thienothiophene-nC₁₀H₂₁) | — — |
| 590 | Se | CH | S | 0 0 | (benzothiophene) | (benzothiophene) | — — |
| 591 | Se | CH | S | 0 0 | (benzothiophene-nC₆H₁₃) | (benzothiophene-nC₆H₁₃) | — — |
| 592 | Se | CH | S | 0 0 | (benzothiophene-nC₁₀H₂₁) | (benzothiophene-nC₁₀H₂₁) | — — |
| 593 | Se | CH | S | 0 0 | (benzothiophene-nC₆H₁₃) | (benzothiophene-nC₆H₁₃) | — — |
| 594 | Se | CH | S | 0 0 | (benzothiophene-nC₁₀H₂₁) | (benzothiophene-nC₁₀H₂₁) | — — |
| 595 | Se | CH | S | 0 0 | (benzothiophene) | (benzothiophene) | — — |
| 596 | Se | CH | S | 0 0 | (benzothiophene-nC₆H₁₃) | (benzothiophene-nC₆H₁₃) | — — |
| 597 | Se | CH | S | 0 0 | (benzothiophene-nC₁₀H₂₁) | (benzothiophene-nC₁₀H₂₁) | — — |
| 598 | Se | CH | S | 0 0 | (benzothiophene-nC₆H₁₃) | (benzothiophene-nC₆H₁₃) | — — |

TABLE 30-continued
| 599 | Se | CH | S | 0 | 0 |  | 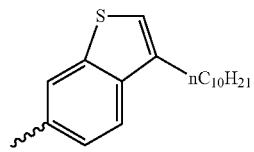 | — | — |
| 600 | Se | CH | S | 0 | 0 | 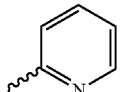 | 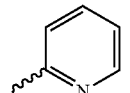 | — | — |
TABLE 31
| 601 | Se | CH | S | 0 | 0 | 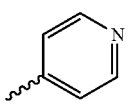 | 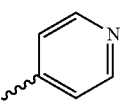 | — | — |
| 602 | Se | CH | S | 0 | 0 | 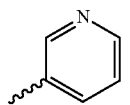 | 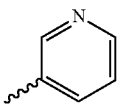 | — | — |
| 603 | Se | CH | S | 0 | 0 | 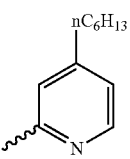 | 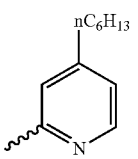 | — | — |
| 604 | Se | CH | S | 0 | 0 | 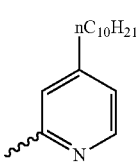 | 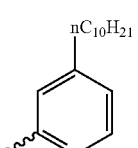 | — | — |
| 605 | Se | CH | S | 0 | 0 | 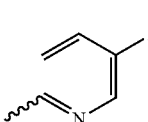 | 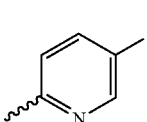 | — | — |
| 606 | Se | CH | S | 0 | 0 | 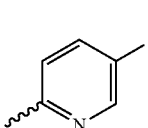 | 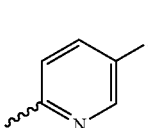 | — | — |
| 607 | Se | CH | S | 0 | 0 | 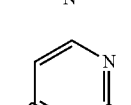 | 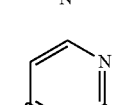 | — | — |
| 608 | Se | CH | S | 0 | 0 | 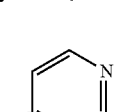 | 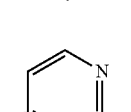 | — | — |
| 609 | Se | CH | S | 0 | 0 | 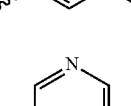 | 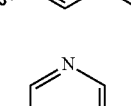 | — | — |

TABLE 31-continued

| 610 | Se | CH | S | 0 | 0 | 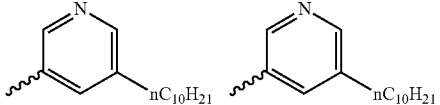 | | — | — |

| 611 | S | CH | N(n-C$_{10}$H$_{21}$) | 0 | 0 | CH$_3$ | CH$_3$ | — | — |
| 612 | S | CH | N(n-C$_{10}$H$_{21}$) | 0 | 0 | n-C$_4$H$_9$ | n-C$_4$H$_9$ | — | — |
| 613 | S | CH | N(n-C$_{10}$H$_{21}$) | 0 | 0 | n-C$_5$H$_{11}$ | n-C$_5$H$_{11}$ | — | — |
| 614 | S | CH | N(n-C$_{10}$H$_{21}$) | 0 | 0 | n-C$_6$H$_{13}$ | n-C$_6$H$_{13}$ | — | — |
| 615 | S | CH | N(n-C$_{10}$H$_{21}$) | 0 | 0 | n-C$_7$H$_{15}$ | n-C$_7$H$_{15}$ | — | — |
| 616 | S | CH | N(n-C$_{10}$H$_{21}$) | 0 | 0 | n-C$_8$H$_{17}$ | n-C$_8$H$_{17}$ | — | — |
| 617 | S | CH | N(n-C$_{10}$H$_{21}$) | 0 | 0 | n-C$_9$H$_{19}$ | n-C$_9$H$_{19}$ | — | — |
| 618 | S | CH | N(n-C$_{10}$H$_{21}$) | 0 | 0 | n-C$_{10}$H$_{21}$ | n-C$_{10}$H$_{21}$ | — | — |
| 619 | S | CH | N(n-C$_{10}$H$_{21}$) | 0 | 0 | n-C$_{11}$H$_{23}$ | n-C$_{11}$H$_{23}$ | — | — |
| 620 | S | CH | N(n-C$_{10}$H$_{21}$) | 0 | 0 | n-C$_{12}$H$_{25}$ | n-C$_{12}$H$_{25}$ | — | — |

TABLE 32

| 621 | S | CH | N(n-C$_{10}$H$_{21}$) | 0 | 0 | 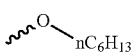 | 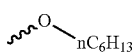 | — | — |
| 622 | S | CH | N(n-C$_{10}$H$_{21}$) | 0 | 0 | 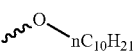 | 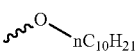 | — | — |
| 623 | S | CH | N(n-C$_{10}$H$_{21}$) | 0 | 0 | 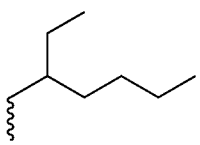 | 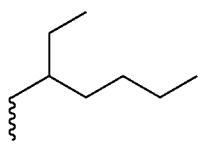 | — | — |
| 624 | S | CH | N(n-C$_{10}$H$_{21}$) | 0 | 0 | 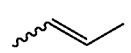 | 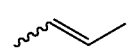 | — | — |
| 625 | S | CH | N(n-C$_{10}$H$_{21}$) | 0 | 0 |  |  | — | — |
| 626 | S | CH | N(n-C$_{10}$H$_{21}$) | 0 | 0 | 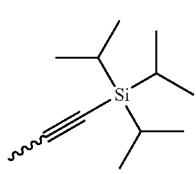 | 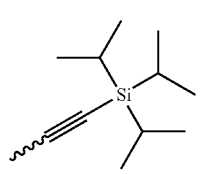 | — | — |
| 627 | S | CH | N(n-C$_{10}$H$_{21}$) | 0 | 0 | 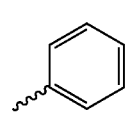 | 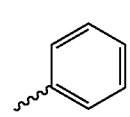 | — | — |
| 628 | S | CH | N(n-C$_{10}$H$_{21}$) | 0 | 0 | 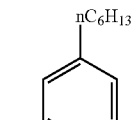 | 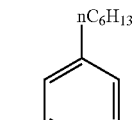 | — | — |
| 629 | S | CH | N(n-C$_{10}$H$_{21}$) | 0 | 0 | 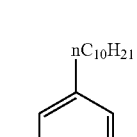 | 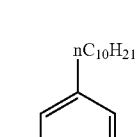 | — | — |

TABLE 32-continued
| | | | | | | | | |
|---|---|---|---|---|---|---|---|---|
| 630 | S | CH | N(n-C$_{10}$H$_{21}$) | 0 | 0 | 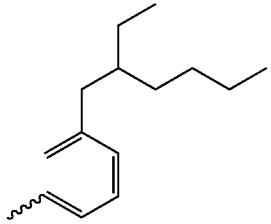 | 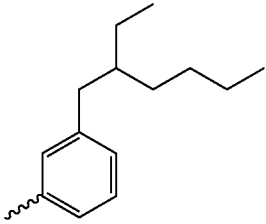 | — — |
| 631 | S | CH | N(n-C$_{10}$H$_{21}$) | 0 | 0 | 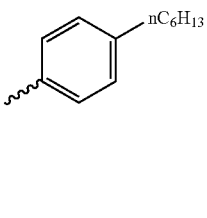 | 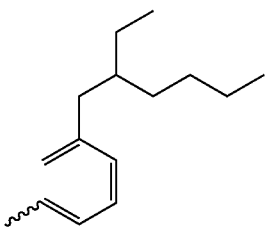 | — — |
| 632 | S | CH | N(n-C$_{10}$H$_{21}$) | 0 | 0 | 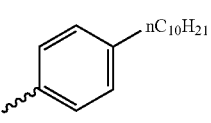 | 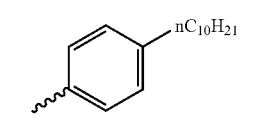 | — — |
| 633 | S | CH | N(n-C$_{10}$H$_{21}$) | 0 | 0 | 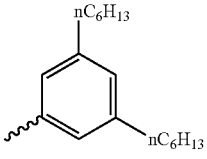 | 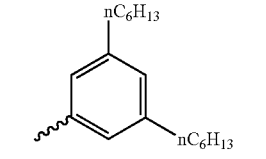 | — — |
| 634 | S | CH | N(n-C$_{10}$H$_{21}$) | 0 | 0 | 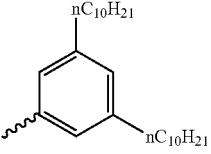 | 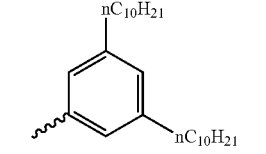 | — — |
| 635 | S | CH | N(n-C$_{10}$H$_{21}$) | 0 | 0 | 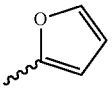 | 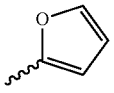 | — — |
| 636 | S | CH | N(n-C$_{10}$H$_{21}$) | 0 | 0 | 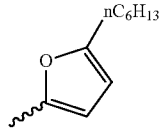 | 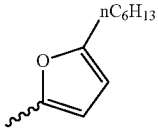 | — — |
| 637 | S | CH | N(n-C$_{10}$H$_{21}$) | 0 | 0 | 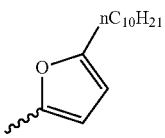 | 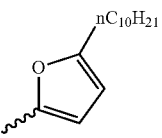 | — — |
| 638 | S | CH | N(n-C$_{10}$H$_{21}$) | 0 | 0 | 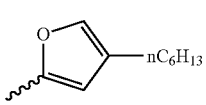 | 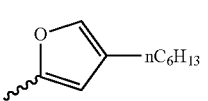 | — — |
| 639 | S | CH | N(n-C$_{10}$H$_{21}$) | 0 | 0 | 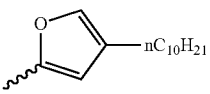 | 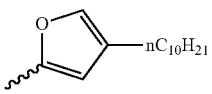 | — — |
| 640 | S | CH | N(n-C$_{10}$H$_{21}$) | 0 | 0 | 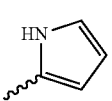 | 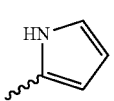 | — — |

TABLE 33

| | | | | | | | | | |
|---|---|---|---|---|---|---|---|---|---|
| 641 | S | CH | N(n-C$_{10}$H$_{21}$) | 0 | 0 | 1-methyl-2-(nC$_6$H$_{13}$)-pyrrol-5-yl | 1-methyl-2-(nC$_6$H$_{13}$)-pyrrol-5-yl | — | — |
| 642 | S | CH | N(n-C$_{10}$H$_{21}$) | 0 | 0 | 1-(nC$_6$H$_{13}$)-pyrrol-2-yl | 1-(nC$_6$H$_{13}$)-pyrrol-2-yl | — | — |
| 643 | S | CH | N(n-C$_{10}$H$_{21}$) | 0 | 0 | 1-(nC$_{10}$H$_{21}$)-pyrrol-2-yl | 1-(nC$_{10}$H$_{21}$)-pyrrol-2-yl | — | — |
| 644 | S | CH | N(n-C$_{10}$H$_{21}$) | 0 | 0 | thiophen-2-yl | thiophen-2-yl | — | — |
| 645 | S | CH | N(n-C$_{10}$H$_{21}$) | 0 | 0 | thiophen-3-yl | thiophen-3-yl | — | — |
| 646 | S | CH | N(n-C$_{10}$H$_{21}$) | 0 | 0 | 4-(nC$_5$H$_{11}$)-thiophen-2-yl | 4-(nC$_5$H$_{11}$)-thiophen-2-yl | — | — |
| 647 | S | CH | N(n-C$_{10}$H$_{21}$) | 0 | 0 | 4-(nC$_6$H$_{13}$)-thiophen-2-yl | 4-(nC$_6$H$_{13}$)-thiophen-2-yl | — | — |
| 648 | S | CH | N(n-C$_{10}$H$_{21}$) | 0 | 0 | 4-(nC$_8$H$_{17}$)-thiophen-2-yl | 4-(nC$_8$H$_{17}$)-thiophen-2-yl | — | — |
| 649 | S | CH | N(n-C$_{10}$H$_{21}$) | 0 | 0 | 4-(nC$_{10}$H$_{21}$)-thiophen-2-yl | 4-(nC$_{10}$H$_{21}$)-thiophen-2-yl | — | — |
| 650 | S | CH | N(n-C$_{10}$H$_{21}$) | 0 | 0 | 4-(nC$_{12}$H$_{25}$)-thiophen-2-yl | 4-(nC$_{12}$H$_{25}$)-thiophen-2-yl | — | — |
| 651 | S | CH | N(n-C$_{10}$H$_{21}$) | 0 | 0 | 5-(nC$_6$H$_{13}$)-thiophen-2-yl | 5-(nC$_6$H$_{13}$)-thiophen-2-yl | — | — |
| 652 | S | CH | N(n-C$_{10}$H$_{21}$) | 0 | 0 | 5-(nC$_{10}$H$_{21}$)-thiophen-2-yl | 5-(nC$_{10}$H$_{21}$)-thiophen-2-yl | — | — |
| 653 | S | CH | N(n-C$_{10}$H$_{21}$) | 0 | 0 | 2-(nC$_5$H$_{11}$)-thiophen-4-yl | 2-(nC$_5$H$_{11}$)-thiophen-4-yl | — | — |

TABLE 33-continued
| 654 | S | CH | N(n-C10H21) | 0 | 0 | 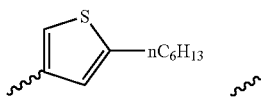 | 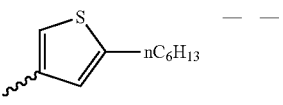 | — | — |
| 655 | S | CH | N(n-C10H21) | 0 | 0 | 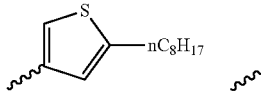 | 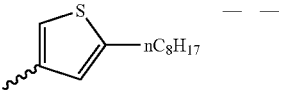 | — | — |
| 656 | S | CH | N(n-C10H21) | 0 | 0 | 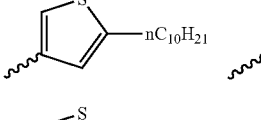 | 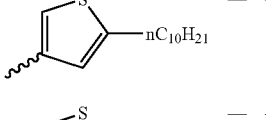 | — | — |
| 657 | S | CH | N(n-C10H21) | 0 | 0 | 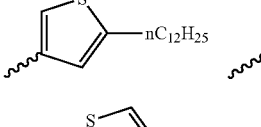 | 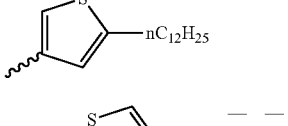 | — | — |
| 658 | S | CH | N(n-C10H21) | 0 | 0 | 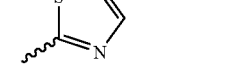 | 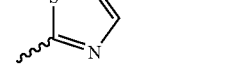 | — | — |
| 659 | S | CH | N(n-C10H21) | 0 | 0 | 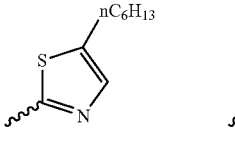 | 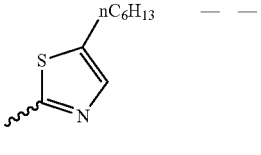 | — | — |
| 660 | S | CH | N(n-C10H21) | 0 | 0 | 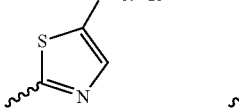 | 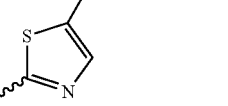 | — | — |
TABLE 34
| 661 | S | CH | N(n-C10H21) | 0 | 0 | 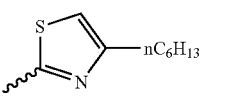 | 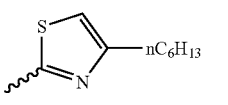 | — | — |
| 662 | S | CH | N(n-C10H21) | 0 | 0 | 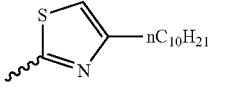 | 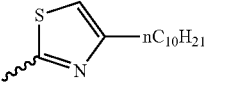 | — | — |
| 663 | S | CH | N(n-C10H21) | 0 | 0 | 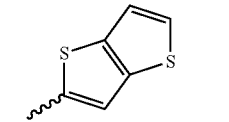 | 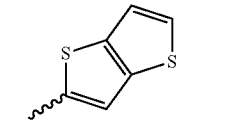 | — | — |
| 664 | S | CH | N(n-C10H21) | 0 | 0 | 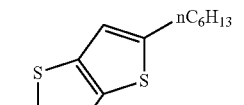 | 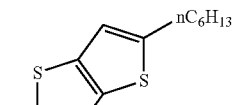 | — | — |
| 665 | S | CH | N(n-C10H21) | 0 | 0 | 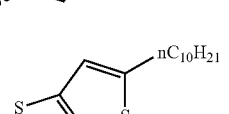 | 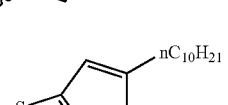 | — | — |

TABLE 34-continued

| | | | | | | | | | |
|---|---|---|---|---|---|---|---|---|---|
| 666 | S | CH | N(n-C$_{10}$H$_{21}$) | 0 | 0 | (benzothiophene-2-yl) | (benzothiophene-2-yl) | — | — |
| 667 | S | CH | N(n-C$_{10}$H$_{21}$) | 0 | 0 | (5-nC$_6$H$_{13}$-benzothiophene-2-yl) | (5-nC$_6$H$_{13}$-benzothiophene-2-yl) | — | — |
| 668 | S | CH | N(n-C$_{10}$H$_{21}$) | 0 | 0 | (5-nC$_{10}$H$_{21}$-benzothiophene-2-yl) | (5-nC$_{10}$H$_{21}$-benzothiophene-2-yl) | — | — |
| 669 | S | CH | N(n-C$_{10}$H$_{21}$) | 0 | 0 | (4-nC$_6$H$_{13}$-benzothiophene-2-yl) | (4-nC$_6$H$_{13}$-benzothiophene-2-yl) | — | — |
| 670 | S | CH | N(n-C$_{10}$H$_{21}$) | 0 | 0 | (4-nC$_{10}$H$_{21}$-benzothiophene-2-yl) | (4-nC$_{10}$H$_{21}$-benzothiophene-2-yl) | — | — |
| 671 | S | CH | N(n-C$_{10}$H$_{21}$) | 0 | 0 | (benzothiophene-6-yl) | (benzothiophene-6-yl) | — | — |
| 672 | S | CH | N(n-C$_{10}$H$_{21}$) | 0 | 0 | (2-nC$_6$H$_{13}$-benzothiophene-6-yl) | (2-nC$_6$H$_{13}$-benzothiophene-6-yl) | — | — |
| 673 | S | CH | N(n-C$_{10}$H$_{21}$) | 0 | 0 | (2-nC$_{10}$H$_{21}$-benzothiophene-6-yl) | (2-nC$_{10}$H$_{21}$-benzothiophene-6-yl) | — | — |
| 674 | S | CH | N(n-C$_{10}$H$_{21}$) | 0 | 0 | (3-nC$_6$H$_{13}$-benzothiophene-6-yl) | (3-nC$_6$H$_{13}$-benzothiophene-6-yl) | — | — |
| 675 | S | CH | N(n-C$_{10}$H$_{21}$) | 0 | 0 | (3-nC$_{10}$H$_{21}$-benzothiophene-6-yl) | (3-nC$_{10}$H$_{21}$-benzothiophene-6-yl) | — | — |

115 116
TABLE 34-continued
| 676 | S | CH | N(n-C$_{10}$H$_{21}$) | 0 | 0 | 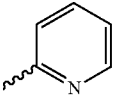 | 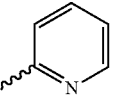 | — | — |
| 677 | S | CH | N(n-C$_{10}$H$_{21}$) | 0 | 0 | 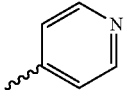 | 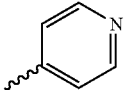 | — | — |
| 678 | S | CH | N(n-C$_{10}$H$_{21}$) | 0 | 0 | 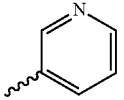 | 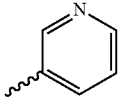 | — | — |
| 679 | S | CH | N(n-C$_{10}$H$_{21}$) | 0 | 0 | 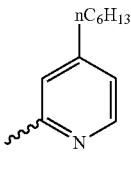 | 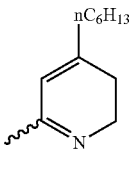 | — | — |
| 680 | S | CH | N(n-C$_{10}$H$_{21}$) | 0 | 0 | 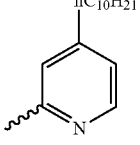 | 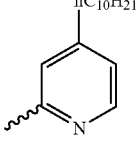 | — | — |
TABLE 35
| 681 | S | CH | N(n-C$_{10}$H$_{21}$) | 0 | 0 | 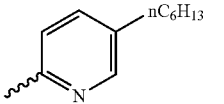 | 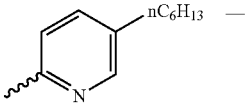 | — | — |
| 682 | S | CH | N(n-C$_{10}$H$_{21}$) | 0 | 0 | 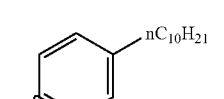 | 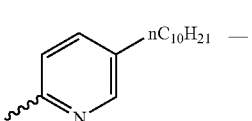 | — | — |
| 683 | S | CH | N(n-C$_{10}$H$_{21}$) | 0 | 0 | 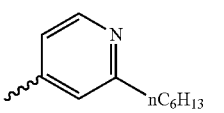 | 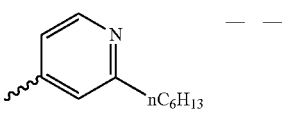 | — | — |
| 684 | S | CH | N(n-C$_{10}$H$_{21}$) | 0 | 0 | 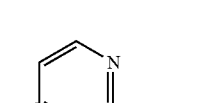 | 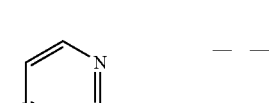 | — | — |
| 685 | S | CH | N(n-C$_{10}$H$_{21}$) | 0 | 0 | 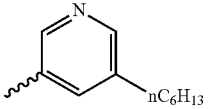 | 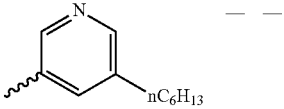 | — | — |
| 686 | S | CH | N(n-C$_{10}$H$_{21}$) | 0 | 0 | 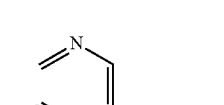 | 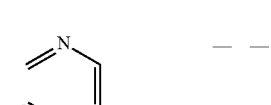 | — | — |

A method of synthesizing the compound represented by Formula 1 is not particularly limited and the compound represented by Formula 1 can be synthesized with reference to well-known methods.

Examples of the synthesis method preferably include a method including a step of causing a compound represented by Formula 6 or 7 to react with a compound represented by Formula 8 in existence of a transition metal catalyst and an organic solvent.

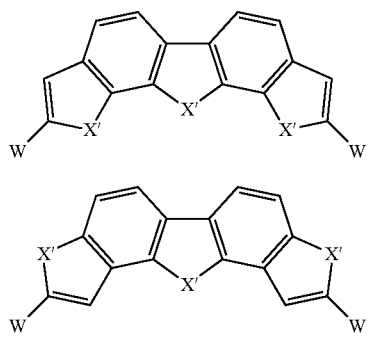

In Formulae 6 and 7,

X"'s each independently represent an oxygen atom, a sulfur atom, or a selenium atom, and W's each independently represent a halogen atom or a perfluoroalkylsulfonyloxy group.

In Formula 8, $R^{11}$ represents an alkyl group, an alkenyl group, an alkynyl group, an aryl group, or a heteroaryl group and may further have a sub stituent, M represents magnesium, silicon, boron, tin, or zinc, $R^{12}$'s each independently represent a halogen atom, an alkyl group, an alkenyl group, an alkynyl group, an alkoxy group, or a hydroxyl group, may be identical to or different from each other, and may form a ring with each other, and i represents an integer of 1 to 3 and a valence of M-1. Here, in a case where M is boron, i is most preferably 3.

The transition metal catalyst is not particularly limited, and a transition metal catalyst used in coupling reaction such as Kumada-Tamao-Corriu coupling, Hiyama coupling, Suzuki-Miyaura coupling, Midori-Kosugi-Stille coupling, Sonogashira-Hagiwara coupling, Mizoroki-Heck reaction, and Negishi coupling can be suitably used. Among these, a palladium catalyst or a nickel catalyst is preferable, and a palladium catalyst is more preferable. The metal catalyst can have an arbitrary ligand, depending on the reaction.

The organic solvent is not particularly limited and can be suitably selected, depending on a substrate or a catalyst.

The amounts used of the compounds represented by Formulae 6 to 8, the transition metal catalyst, and the organic solvent are not particularly limited and suitably selected, if necessary.

The heating temperature at the time of reaction is not particularly limited, but is preferably 25° C. to 200° C. and more preferably 40° C. to 150° C.

Only one type of the compound represented by Formula 1 may be contained in the semiconductor active layer according to the organic semiconductor element of the present invention, or two or more types thereof may be contained. However, in view of alignment, it is preferable that only one type of compound represented by Formula 1 is contained.

Only one type of the compound represented by Formula 1 may be contained in the organic semiconductor film, the material for forming an organic semiconductor film, or the composition for forming an organic semiconductor film described below, or two or more types thereof may be contained. However, in view of alignment, it is preferable that only one type of compound represented by Formula 1 is contained.

In the semiconductor active layer of the organic semiconductor element according to the present invention or an organic semiconductor film according to the present invention described below, an entire content of the compound represented by Formula 1 is preferably 30 to 100 mass %, more preferably 50 to 100 mass %, and even more preferably 70 to 100 mass %. In a case where a binder polymer described below is not contained, the total content is preferably 90 to 100 mass % and more preferably 95 to 100 mass %.

<Binder Polymer>

A semiconductor active layer of an organic semiconductor element according to the present invention may contain a binder polymer.

The organic semiconductor element according to the present invention may be an organic semiconductor element having the semiconductor active layer and a layer including a binder polymer.

The types of binder polymer are not particularly limited, and well-known binder polymers can be used.

Examples of the binder polymer include a polystyrene resin, an acrylic resin, rubber, and a thermoplastic elastomer.

Among these, as the binder polymer, a polymer compound (a polymer having a monomer unit having a benzene ring group) having a benzene ring is preferable. The content of the monomer unit having a benzene ring group is not particularly limited. However, the content is preferably 50 mol % or greater, more preferably 70 mol % or greater, and even more preferably 90 mol % or greater with respect to the entire monomer unit. The upper limit is not particularly limited, but examples of the upper limit include 100 mol %.

Examples of the binder polymer include polystyrene, poly(α-methylstyrene), polyvinyl cinnamate, poly(4-vinylphenyl), and poly(4-methyl styrene).

A weight-average molecular weight of the binder polymer is not particularly limited, but is preferably 1,000 to 2,000,000, more preferably 3,000 to 1,000,000, and even more preferably 5,000 to 600,000.

In a case where a solvent described below is used, it is preferable that the binder polymer exhibits solubility higher than the solubility of the specific compound in a used solvent. If the above aspect is adopted, mobility and heat stability of the obtained organic semiconductor are further improved.

A content of the binder polymer in the semiconductor active layer of the organic semiconductor element of the present invention is preferably 1 to 200 parts by mass, more preferably 10 to 150 parts by mass, and even more preferably 20 to 120 parts by mass with respect to 100 parts by mass of the compound represented by Formula 1. If the content is within the above range, mobility and heat stability of the obtained organic semiconductor are further improved.

<Other Components>

Other components may be included other than the compound represented by Formula 1 and the binder polymer in the semiconductor active layer in the organic semiconductor element of the present invention.

As other components, known additives and the like can be used.

In the semiconductor active layer, a content of the components other than the compound represented by Formula 1 and the binder polymer is preferably 10 mass % or less, more preferably 5 mass % or less, even more preferably 1 mass % or less, and particularly preferably 0.1 mass % or less. If the content of other components is within the above range, film formability is improved, and mobility and heat stability of the obtained organic semiconductor are further improved.

The method of forming the semiconductor active layer according to the organic semiconductor element of the present invention is not particularly limited. However, a desired semiconductor active layer can be formed by applying the composition for forming an organic semiconductor according to the present invention described below to a source electrode, a drain electrode, and a gate insulating film and performing a drying treatment, if necessary.

The organic semiconductor element of the present invention is preferably manufactured using the composition for forming an organic semiconductor film of the present invention described below.

A method of manufacturing an organic semiconductor film or an organic semiconductor element by using the composition for forming an organic semiconductor film of the present invention is not particularly limited, and known methods can be adopted. Examples thereof include a method of manufacturing an organic semiconductor film by applying the composition onto a predetermined base material and if necessary, performing a drying treatment.

The method of applying the composition onto a base material is not particularly limited, and known methods can be adopted. Examples thereof include an ink jet printing method, a flexographic printing method, a bar coating method, a spin coating method, a knife coating method, a doctor blade method, and the like. Among these, an ink jet printing method and a flexographic printing method are preferable.

Preferred examples of the flexographic printing method include an aspect in which a photosensitive resin plate is used as a flexographic printing plate. By printing the composition onto a substrate according to the aspect, a pattern can be easily formed.

Among these, the method of manufacturing the organic semiconductor element according to the present invention preferably includes a step of coating a substrate with the composition for forming an organic semiconductor film according to the present invention and manufacturing the semiconductor active layer by drying.

The organic composition for forming an organic semiconductor film according to the present invention described below preferably includes a solvent and more preferably includes an organic solvent.

As the solvent, well-known solvents can be used.

Specifically, examples thereof include a hydrocarbon-based solvent such as hexane, octane, decane, toluene, xylene, mesitylene, ethylbenzene, decalin, and 1-methyl-naphthalene, a ketone-based solvent such as acetone, methyl ethyl ketone, methyl isobutyl ketone, and cyclohexanone, a halogenated hydrocarbon-based solvent such as dichloromethane, chloroform, tetrachloromethane, dichloroethane, trichloroethane, tetrachloroethane, chlorobenzene, dichlorobenzene, and chlorotoluene, an ester-based solvent such as ethyl acetate, butyl acetate, and amyl acetate, an alcohol-based solvent such as methanol, propanol, butanol, pentanol, hexanol, cyclohexanol, methyl cellosolve, ethyl cellosolve, and ethylene glycol, an ether-based solvent such as dibutyl ether, tetrahydrofuran, dioxane, and anisole, an amide-based solvent such as N,N-dimethylformamide and N,N-dimethylacetamide, an imide-based solvent such as 1-methyl-2-pyrrolidone and 1-methyl-2-imidazolidinone, a sulfoxide-based solvent such as dimethylsulfoxide, and a nitrile-based solvent such as acetonitrile.

The solvent may be used singly or two or more types thereof may be used in combination.

Among these, a hydrocarbon-based solvent, a halogenated hydrocarbon-based solvent, and/or an ether-based solvent are preferable, and toluene, xylene, mesitylene, tetralin, dichlorobenzene, and anisole are more preferable.

In a case where the solvent is contained, the content of the compound represented by in Formula 1 in the organic composition for forming an organic semiconductor film of the present invention is preferably 0.01 to 80 mass %, more preferably 0.05 to 10 mass %, and even more preferably 0.1 to 5 mass %. The content of the binder polymer is preferably 0.01 to 80 mass %, more preferably 0.05 to 10 mass %, and even more preferably 0.1 to 5 mass %. If the content is in the range described above, coating properties are excellent, and thus an organic semiconductor film can be easily formed.

The drying treatment in the above step is a treatment performed if necessary, and the optimal treatment conditions are appropriately selected according to the type of the specific compound and the solvent used. In view of further improving mobility and heat stability of the obtained organic semiconductor and improving productivity, a heating temperature is preferably 30° C. to 200° C. and more preferably 40° C. to 150° C., and a heating time is preferably 10 to 300 minutes and more preferably 30 to 180 minutes.

A thickness of the formed semiconductor active layer is not particularly limited. From the viewpoint of mobility and heat stability of the obtained organic semiconductor, the film thickness is preferably 10 to 500 nm and more preferably 20 to 200 nm.

The organic semiconductor element is not particularly limited, but is preferably an organic semiconductor element having 2 to 5 terminals, and more preferably an organic semiconductor element having 2 or 3 terminals.

It is preferable that the organic semiconductor element is not a photoelectric conversion element.

The organic semiconductor element according to the present invention is preferably a non-luminous organic semiconductor element.

Examples of a 2-terminal element include a rectifier diode, a constant voltage diode, a PIN diode, a Schottky barrier diode, a surge protection diode, a diac, a varistor, a tunnel diode, and the like.

Examples of a 3-terminal element include a bipolar transistor, a Darlington transistor, a field effect transistor, insulated gate bipolar transistor, a uni-junction transistor, a static induction transistor, a gate turn-off thyristor, a triac, a static induction thyristor, and the like.

Among these, a rectifier diode and transistors are preferable, and a field effect transistor is more preferable.

As the field effect transistor, an organic thin film transistor is preferable.

An aspect of the organic thin film transistor of the present invention will be described with reference to the drawings.

In FIG. 1, an organic semiconductor layer 14 corresponds to a film (semiconductor active layer) formed from the composition.

The laminate structure of an organic field effect transistor is not particularly limited, and the organic field effect transistor can be caused to have various well-known structures.

Examples of the structure of the organic thin film transistor according to the present invention include a structure (bottom gate-top contact type) in which an electrode, an insulator layer, a semiconductor active layer (organic semiconductor layer), and two electrodes are sequentially arranged on an upper surface of a substrate on the lowermost layer. In this structure, electrodes on the upper surface of the substrate on the lowermost layer are provided at a portion of the substrate, and the insulator layer is arranged so as to come into contact with the substrate at a portion other than the electrodes. Two electrodes provided on the upper surface of the semiconductor active layer are provided so as to be separated from each other.

A configuration of a bottom gate-top contact type element is illustrated in FIG. 1.

FIG. 1 is a schematic view illustrating a cross-section of an exemplary structure in an organic thin film transistor manufactured as a substrate for measuring FET characteristics in an example.

In the organic thin film transistor of FIG. 1, a substrate 11 is arranged on the lowermost layer, the electrode 12 is provided in a portion of the upper surface, the electrode 12 is further coated, and the insulator layer 13 is provided so as to come into contact with the substrate 11 at a portion other than the electrode 12. A semiconductor active layer 14 is provided on the upper surface of the insulator layer 13, and two electrodes 15a and 15b are provided at a portion of the upper surface thereof.

In the organic thin film transistor illustrated in FIG. 1, the electrode 12 is a gate, and the electrode 15a and the electrode 15b are respectively a drain and a source. The organic thin film transistor illustrated in FIG. 1 is an insulating gate-type FET in which a portion between a gate and a channel which is a current path between a drain and a source is insulated.

Examples of the structure of the organic thin film transistor according to the present invention include a bottom gate-bottom contact type element.

Figure 2:
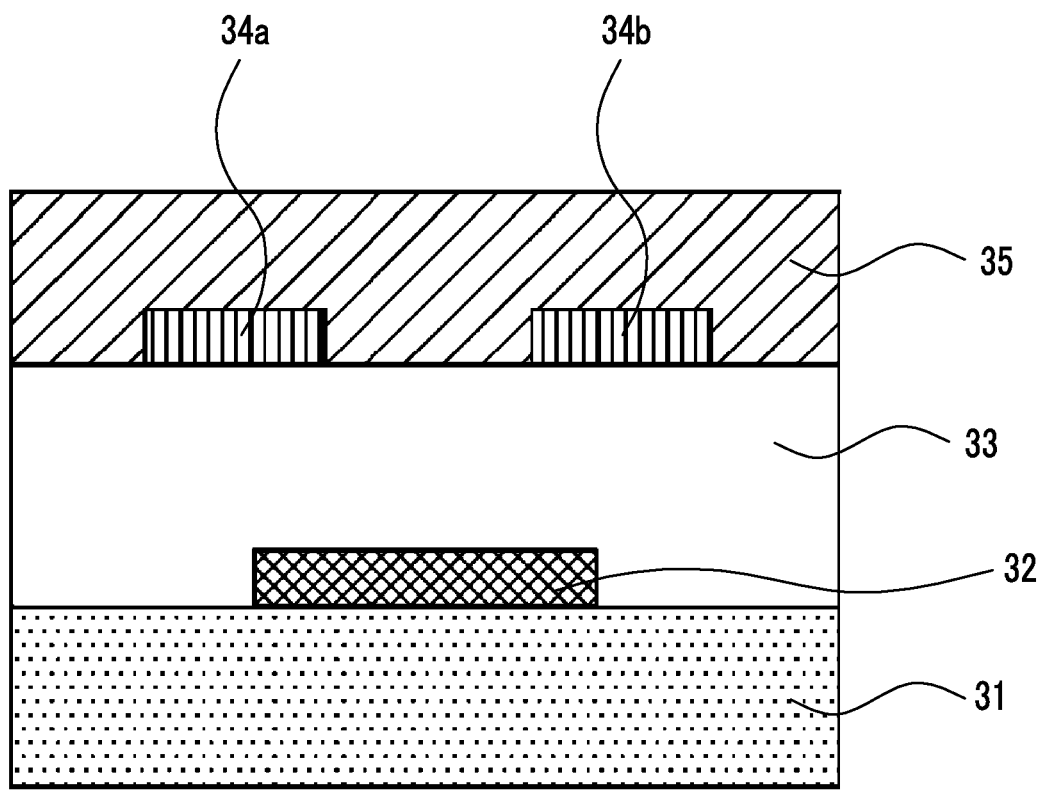
FIG. 2 is a schematic cross-sectional view of another aspect of the organic semiconductor element according to the present invention.

A configuration of the bottom gate-bottom contact type element is illustrated in FIG. 2.

FIG. 2 is a schematic view illustrating a cross section of a structure of an organic thin film transistor manufactured as a substrate for measuring FET characteristics in the example.

In the organic thin film transistor in FIG. 2, a substrate 31 is provided on the lowermost layer, an electrode 32 is provided in a portion of the upper surface thereof, the electrode 32 is further coated, and an insulator layer 33 is provided so as to come into contact with the substrate 31 at a portion other than the electrode 32. A semiconductor active layer 35 is provided on the upper surface of the insulator layer 33, and two electrodes 34a and 34b are provided at a lower portion of the semiconductor active layer 35.

In the organic thin film transistor illustrated in FIG. 2, the electrode 32 is a gate, and the electrode 34a and the electrode 34b are respectively a drain and a source. In the organic thin film transistor illustrated in FIG. 2, an insulating gate-type FET in which a portion between a gate and a channel which is a current path between a drain and a source is insulated.

Hereinafter, the substrate, the gate electrode, the gate insulating film, the source electrode, the drain electrode, the sealing layer, and methods for forming each of these will be specifically described.

<Substrate>

The substrate plays a role of supporting the gate electrode, the source electrode, the drain electrode, and the like which will be described later.

The type of the substrate is not particularly limited, and examples thereof include a plastic substrate, a glass substrate, a ceramic substrate, and the like. Among these, from the viewpoint of applicability to each device and costs, a plastic substrate or a ceramic substrate is preferable.

Examples of materials of the plastic substrate include a thermosetting resin (for example, an epoxy resin, a phenol resin, a polyimide resin, or a polyester resin (for example, polyethylene terephthalate (PET) or polyethylene naphthalate (PEN)) and a thermoplastic resin (for example, a phenoxy resin, a polyethersulfone, polysulfone, or polyphenylene sulfone).

Examples of materials of the ceramic substrate include alumina, aluminum nitride, zirconia, silicon, silicon nitride, silicon carbide, and the like.

Examples of materials of the glass substrate include soda lime glass, potash glass, borosilicate glass, quartz glass, aluminosilicate glass, lead glass, and the like.

<Gate Electrode, Source Electrode, and Drain Electrode>

Examples of materials of the gate electrode, the source electrode, and the drain electrode include a metal such as gold (Au), silver, aluminum (Al), copper, chromium, nickel, cobalt, titanium, platinum, tantalum, magnesium, calcium, barium, or sodium; a conductive oxide such as $InO_2$, $SnO_2$, or indium tin oxide (ITO); a conductive polymer such as polyaniline, polypyrrole, polythiophene, polyacetylene, or polydiacetylene; a semiconductor such as silicon, germanium, or gallium arsenide; a carbon material such as fullerene, carbon nanotubes, or graphite; and the like. Among these, gold, silver, chrome, or silicon are more preferable.

A thickness of each of the gate electrode, the source electrode, and the drain electrode is not particularly limited, but is preferably 10 to 500 nm.

A method of forming the gate electrode, the source electrode, and the drain electrode is not particularly limited, but examples thereof include a method of vacuum vapor-depositing or sputtering an electrode material onto a substrate, a method of coating a substrate with a composition for forming an electrode, a method of printing a composition for forming an electrode onto a substrate, and the like. Furthermore, in a case where the electrode is patterned, examples of the patterning method include a photolithography method; a printing method such as ink jet printing, screen printing, offset printing, or relief printing; a mask vapor deposition method; and the like.

<Gate Insulating Film>

Examples of the material of the gate insulating film include a polymer such as polymethyl methacrylate, polystyrene, polyvinyl phenol, polyimide, polycarbonate, polyester, polyvinyl alcohol, polyvinyl acetate, polyurethane, polysulfone, polybenzoxazole, polysilsesquioxane, an epoxy resin, and a phenolic resin, a fluorine polymer-based insulating material such as polytetrafluoroethylene (PTFE) and a cyclic transparent optical polymer (CYTOP, amorphous fluororesin), oxide such as silicon dioxide, aluminum oxide, and titanium oxide; and nitrides such as silicon nitride. Among these materials, silicon dioxide is preferable.

For example, the upper surface of the insulating film may be surface-treated. For example, an insulating film surface-treated by coating the silicon dioxide surface with hexamethyldisilazane (HIVID S), octadecyltrichlorosilane (OTS), or β-phenethyltrimethoxysilane can be preferably used, and an insulating film surface-treated by coating the surface with β-phenethyltrimethoxysilane can be more preferably used.

In a case where a polymer is used as the material of the gate insulating film, it is preferable to use a cross-linking agent (for example, melamine) in combination. If the cross-linking agent is used in combination, the polymer is cross-linked, and durability of the formed gate insulating film is improved.

A film thickness of the gate insulating film is not particularly limited, but is preferably 100 to 1,000 nm.

A method of forming the gate insulating film is not particularly limited, but examples thereof include a method of coating a substrate, on which the gate electrode is formed, with a composition for forming a gate insulating film, a method of vapor-depositing or sputtering the material of the gate insulating film onto a substrate on which the gate electrode is formed, and the like. A method of coating the aforementioned substrate with the composition for forming a gate insulating film is not particularly limited, and it is possible to use a known method (a bar coating method, a spin coating method, a knife coating method, or a doctor blade method).

In a case where the gate insulating film is formed by coating the substrate with the composition for forming a gate insulating film, for the purpose of removing the solvent, causing cross-linking, or the like, the composition may be heated (baked) after coating.

<Binder Polymer Layer>

The organic semiconductor element of the present invention preferably has a layer of the aforementioned binder polymer between a layer containing the semiconductor active layer and an insulating film, and more preferably has the aforementioned binder polymer between the semiconductor active layer and the gate insulating film. A film thickness of the binder polymer layer is not particularly limited, but is preferably 20 to 500 nm. The binder polymer layer should be a layer containing the aforementioned polymer, and is preferably a layer composed of the aforementioned binder polymer.

A method of forming the binder polymer layer is not particularly limited, and a known method (a bar coating method, a spin coating method, a knife coating method, a doctor blade method, or an ink jet method) can be used.

In a case where the binder polymer layer is formed by performing coating by using a composition for forming a binder polymer layer, for the purpose of removing a solvent, causing cross-linking, or the like, the composition may be heated (baked) after coating.

<Sealing Layer>

From the viewpoint of durability, the organic semiconductor element of the present invention preferably comprises a sealing layer as an outermost layer. In the sealing layer, a known sealant can be used.

A thickness of the sealing layer is not particularly limited, but is preferably 0.2 to 10 μm.

A method of forming the sealing layer is not particularly limited, but examples thereof include a method of coating a substrate, on which the gate electrode, the gate insulating film, the source electrode, the drain electrode, and the organic semiconductor film are formed, with a composition for forming a sealing layer, and the like. Specific examples of the method of coating the substrate with the composition for forming a sealing layer are identical to the examples of the method of coating the substrate with the composition for forming a gate insulating film. In a case where the sealing layer is formed by coating the substrate with the composition for forming a sealing layer, for the purpose of removing the solvent, causing cross-linking, or the like, the composition may be heated (baked) after coating.

The substrate, the gate electrode, the gate insulating film, the source electrode, the drain electrode, the organic semiconductor film, and the sealing layer are as described above.

In FIGS. 1 and 2, the aspects of the bottom gate-top contact type organic thin film transistor and the bottom gate-bottom contact type organic thin film transistor were specifically described. However, the organic semiconductor element of the present invention can also suitably used in a top gate-bottom contact type organic thin film transistor and a top gate-top contact type organic thin film transistor.

The organic thin film transistor described above can be suitably used for electronic paper and a display device.

(Composition for Forming Organic Semiconductor Film)

The composition for forming an organic semiconductor film according to the present invention contains the compound represented by Formula 1 (compound according to the present invention).

The composition for forming an organic semiconductor film according to the present invention preferably contains a solvent.

The compound represented by Formula 1, the binder polymer, and the solvent in the composition for forming an organic semiconductor film according to the present invention are identical to the compound represented by Formula 1, the binder polymer, and the solvent, and preferable aspects thereof are also identical.

The composition for forming an organic semiconductor film according to the present invention may include components other than the compound represented by Formula 1 and the binder polymer.

As the components, well-known additives may be used.

The content of the components in addition to the compound represented by Formula 1 and the binder polymer in the composition for forming an organic semiconductor film according to the present invention is preferably 10 mass % or less, more preferably 5 mass % or less, even more preferably 1 mass % or less, and particularly preferably 0.1 mass % or less with respect to the total solid content. If the content is in the range described above, film formability is improved, and mobility and heat stability of the obtained organic semiconductor are further improved. The solid content is an amount of the components excluding the volatile component such as the solvent.

The viscosity of the composition for forming an organic semiconductor film according to the present invention is preferably 3 to 100 mPa·s, more preferably 5 to 50 mPa·s, and even more preferably 9 to 40 mPa·s at 25° C.

As a method of measuring the viscosity, a measuring method in conformity of JIS Z8803 is preferable.

The method of manufacturing the composition for forming an organic semiconductor film according to the present invention is not particularly limited, and well-known methods can be employed. For example, a desired composition can be obtained by adding the compound represented by Formula 1 in a predetermined amount to the solvent and suitably performing a stirring treatment. In a case where the binder polymer is used, the compound represented by Formula 1 and the binder polymer may be simultaneously or sequentially added so as to suitably manufacture the composition.

(Organic Semiconductor Material for Forming Organic Semiconductor Element)

The organic semiconductor material for forming an organic semiconductor element according to the present invention contains the compound represented by Formula 1 (the compound according to the present invention).

The organic semiconductor material for forming an organic semiconductor element according to the present invention preferably contains the binder polymer.

The organic semiconductor material for forming an organic semiconductor element according to the present invention preferably is an organic semiconductor material for an organic thin film transistor.

The compound represented by Formula 1 and the binder polymer in the organic semiconductor material for forming an organic semiconductor element according to the present invention are identical to the compound represented by Formula 1 and the binder polymer in the organic semiconductor element according to the present invention described above, and preferable aspects thereof are also identical.

The organic semiconductor material for forming an organic semiconductor element according to the present invention may include other components in addition to the compound represented by Formula 1 and the binder polymer.

As the component, well-known additives may be used.

The content of the component in addition to the specific compound, the compound represented by Formula 1, and the binder polymer in the organic semiconductor films according to the present invention preferably 10 mass % or less, more preferably 5 mass % or less, even more preferably 1 mass % or less, and particularly preferably 0.1 mass % or less. If the content is in the range above, film formability is improved, and mobility and heat stability of the obtained organic semiconductor are further improved. The solid content is an amount of components other than the volatile components such as the solvent.

(Organic Semiconductor Film)

The organic semiconductor film according to the present invention contains the compound represented by Formula 1 (the compound according to the present invention).

The organic semiconductor film according to the present invention is preferably the organic semiconductor film for the organic semiconductor element.

The compound represented by Formula 1 and the binder polymer in the organic semiconductor film according to the present invention are identical to the compound represented by Formula 1 and the binder polymer in the organic semiconductor element according to the present invention described above, and preferable aspects thereof are also identical.

The composition for forming an organic semiconductor film according to the present invention may include components other than the compound represented by Formula 1 and the binder polymer.

As the other components, well-known additives and the like can be used.

The content of the components other than the compound represented by Formula 1 and the binder polymer in the organic semiconductor film according to the present invention is preferably 10 mass % or less, more preferably 5 mass % or less, even more preferably 1 mass % or less, and particularly preferably 0.1 mass % or less. In this range, film formability is excellent, and mobility and heat stability of the obtained organic semiconductor are more excellent. The solid content refers to an amount of components excluding volatile components such as the solvent.

The film thickness of the organic semiconductor film according to the present invention is not particularly limited. However, in view of mobility and heat stability of the obtained organic semiconductor, the film thickness is preferably 10 to 500 nm and more preferably 20 to 200 nm.

The organic semiconductor film according to the present invention can be suitably used in the organic semiconductor element, and can be particularly suitably used in the organic transistor (organic thin film transistor).

The organic semiconductor film according to the present invention can be suitably manufactured by using the composition for forming an organic semiconductor film according to the present invention.

(Method of Manufacturing Organic Semiconductor Film)

The method of manufacturing an organic semiconductor film according to the present invention is not particularly limited and can be performed by well-known methods, but is preferably a method described below.

That is, the method of manufacturing the organic semiconductor film according to the present invention preferably includes a step of dropwise adding the composition for forming an organic semiconductor film according to the present invention to a portion of an in-plane of a substrate A so as to come into contact with both of the substrate A and a member B, while maintaining a state in which a distance between the substrate A and the member B that is not in contact with the substrate A is maintained to be constant or a state in which the substrate A and the member B are in contact with each other, and a step of forming the semiconductor active layer by gradually drying the dropwise added composition (a drying time is suitably adjusted to be preferably one hour or longer, more preferably three hours or longer, and even more preferably five hours or longer) and precipitating crystals of the compound.

In the manufacturing method, as long as a state in which a distance between the substrate A and the member B is maintained to be constant or a state in which the substrate A and the member B are in contact with each other is maintained, at the time of dropwise adding and/or drying the composition, the positional relationship between the substrate A and the member B may be still or move. The state according to the present invention in which the distance between the substrate A and the member B is maintained to be constant refers to the fact that an angle of the member B to the substrate A is maintained to be constant, and the angle of the member B to the substrate A is preferably 20 degrees or greater, more preferably 30 degrees or greater, and even more preferably 60 degrees or greater.

Hereinafter, with reference to FIG. 3, an example of the method of manufacturing the organic semiconductor film according to the present invention is described.

Figure 3:
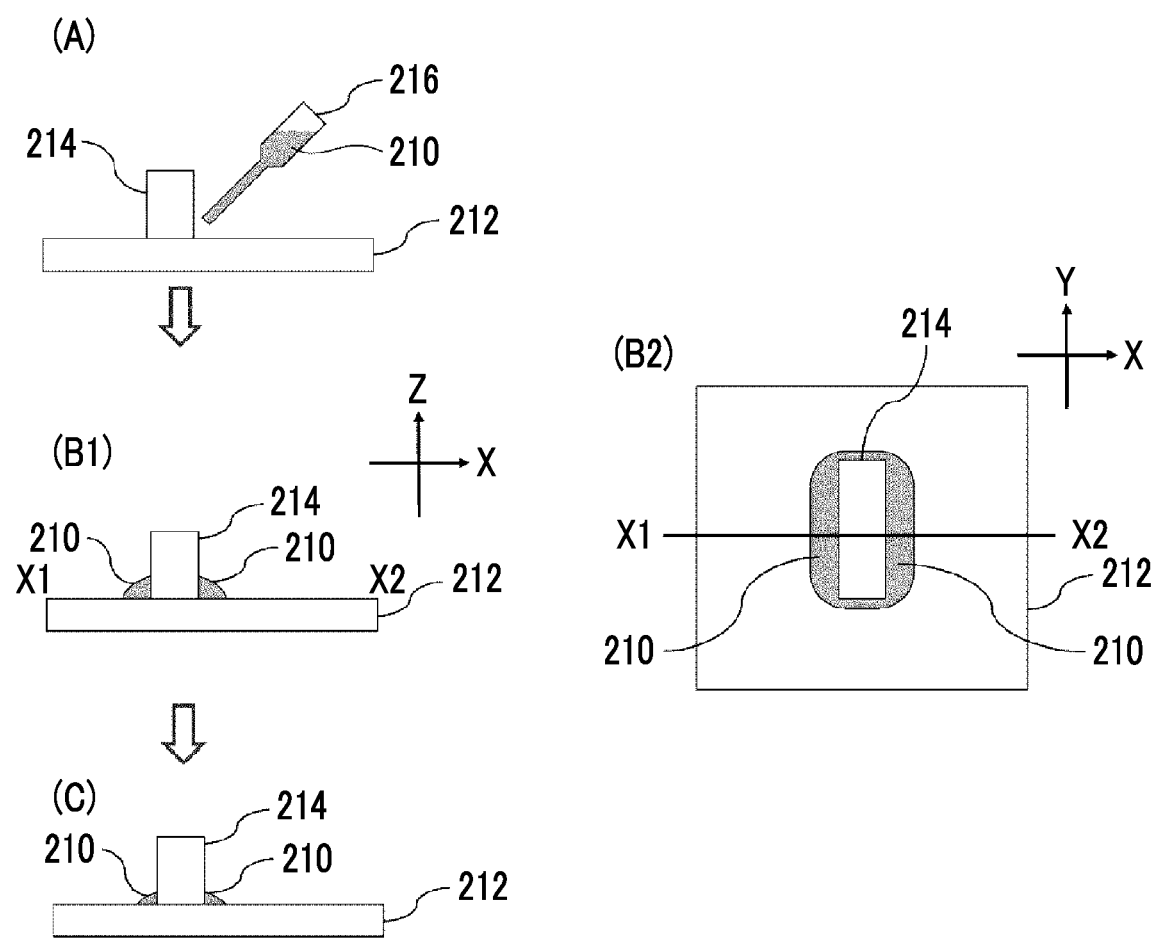
FIG. 3 is a schematic view of an example of a method of manufacturing an organic semiconductor film according to the present invention.

FIG. 3 is a schematic view illustrating an example of the method of manufacturing the organic semiconductor film according to the present invention.

The member 214 was arranged on a surface of a substrate 212 in the center of the substrate 212 as illustrated in FIG. 3(A) in a state in which the substrate 212 and the member 214 are in contact with each other. As the member 214, a member of 10 mm longitudinally×2 mm horizontally×5 mm in height is used, a left-right direction (X axis direction) of FIG. 3(A) is a horizontal direction of the member 214, an upper-lower direction (Z axis direction) of FIG. 3(A) is a height direction of the member 214, and an upper-lower direction (Y axis direction) of FIG. 3(B2) is a machine direction of the member 214.

If the substrate 212 is heated, one drop (about 0.05 ml) of a coating liquid 210 (the composition for forming an organic semiconductor film according to the present invention) is dripped from the side portion of the member 214 by using a pipette 216, so as to come into contact with both of the substrate 212 and the member 214 in FIG. 3(A), the coating liquid 210 is dropwise added to a portion of the in-plane of the substrate 212 as illustrated in FIGS. 3(B1) and 3(B2), and a concave meniscus is formed in an interface with the member 214.

As illustrated in FIG. 3(C), while a state in which the substrate 212 and the member 214 are in contact with each other is maintained, in a state in which a positional relationship between the substrate 212 and the member 214 is still, the coating liquid 210 is dried, the crystals of the compound according to the present invention are precipitated, and the organic semiconductor film can be formed. It is possible to check whether the crystals are precipitated by observation with a polarizing microscope.

As long as a state the substrate 212 and the member 214 are in contact with each other is maintained, at the time of dropwise adding and/or drying the coating liquid 210, a positional relationship between the substrate 212 and the member 214 may be caused to be still or move.

In the method above, even in the plane direction of the film, an opening portion or the like can be easily manufactured in an arbitrary form.

EXAMPLES

Hereinafter, the present invention will be more specifically described based on examples. The materials and the amount thereof used, the proportion of the materials, the content and procedure of treatments, and the like described in the following examples can be appropriately changed within a scope that does not depart from the gist of the present invention. Accordingly, the scope of the present invention is not limited to the following specific examples. Herein, unless otherwise specified, "part" and "%" are based on mass.

Examples 1 and 2, and Comparative Examples 1 to 3

<Synthesis Method>

A compound 1 according to the present invention is synthesized according to a scheme below.

<Synthesis of Intermediate 1>

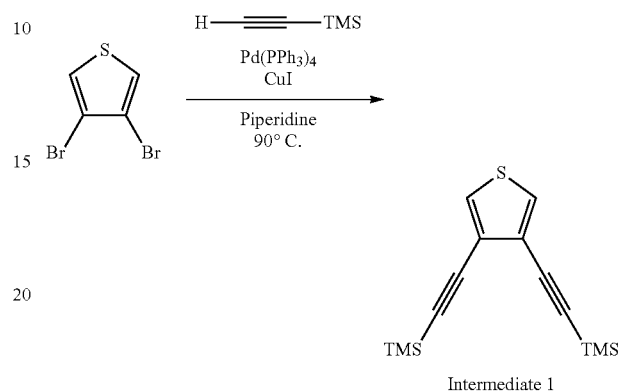

Intermediate 1

50.0 g (207 mmol) of 3,4-dibromonaphthalene, 1.58 g (8.28 mmol) of copper (I) iodide, and 9.57 g (8.28 mmol) of tetrakistriphenylphosphine palladium (0) (Pd(PPh$_3$)$_4$) were added while 1,035 ml of piperidine was degassed by argon bubbling (for 30 minutes), 91.7 ml (662 mmol) of trimethylsilylacetylene (TMS acetylene) was added after degassing was stopped, stirring was performed for 30 minutes at room temperature, heating was performed at 60° C. for 30 minutes, and heating was performed at 90° C. for five hours. After the reaction was completed, the reaction liquid passed through silica gel and celite and was eluted with toluene, and concentration was performed by using an evaporator. The crude product was purified by column chromatography (hexane:toluene=9:1) and further divided, and distillation under reduced pressure was performed a plurality of times by Kugelrohr, so as to obtain 50.15 g (181 mmol, yield: 87%) of an object (Intermediate 1) which is a yellow solid.

$^1$H-NMR (CDCl$_3$, 400 MHz) δ=0.26 (18H, s), 7.39 (2H, s).

<Synthesis of Intermediate 2>

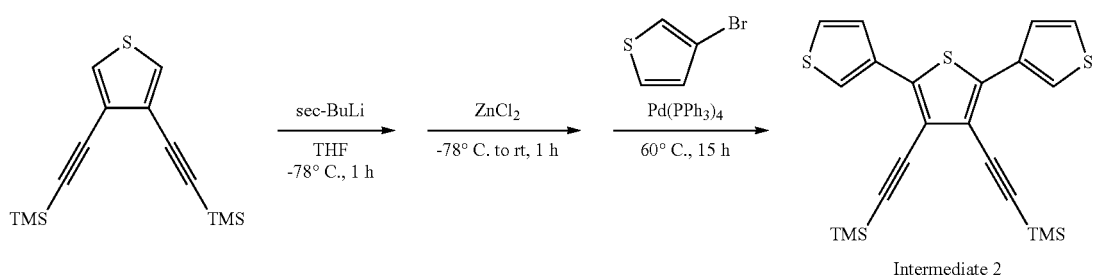 [SMILES: C[Si](C)(C)C#Cc1cscc1C#C[Si](C)(C)C ; "ZnCl2" ; Brc1ccsc1 ; C[Si](C)(C)C#Cc1c(-c2ccsc2)sc(-c2ccsc2)c1C#C[Si](C)(C)C ; "Pd(PPh3)4"]

Intermediate 2

40.0 g (145 mmol) of Intermediate 1 was dissolved in 483 ml of tetrahydrofuran (THF) and cooled to −78° C., and 296 ml (304.5 mmol) of sec-butyllithium (sec-BuLi, 1.03 M cyclohexane/hexane solution) was dropwise added, and stirring was performed for 60 seconds. Thereafter, 305 ml of zinc chloride (II) (1.0 M tetrahydrofuran solution) individually prepared was dropwise added, stirring was performed for 20 minutes, and heating was performed to room temperature. Thereafter, 70.9 g (435 mmol) of 3-bromothiophene 8.38 g (7.25 mmol) of tetrakistriphenylphosphine palladium were added, and heating was performed at 60° C. for 15 hours. After cooling was performed to room temperature, the reaction liquid passed through silica gel and celite was eluted with toluene, and concentration was performed by using an evaporator. The crude product was purified by column chromatography (hexane:toluene=95:5), and re-crystallization was performed with methylene chloride/methanol, so as to obtain 38.9 g (88.3 mmol, yield: 61%) of an object (Intermediate 2) which was a yellow solid.

$^1$H-NMR (CDCl$_3$, 400 MHz) δ=0.30 (18H, s), 7.35 (2H, dd, J=3.0 Hz, 5.0 Hz), 7.59 (2H, dd, J=1.0 Hz, 5.0 Hz), 7.97 (2H, dd, J=1.0 Hz, 3.0 Hz).

<Synthesis of Intermediate 3>

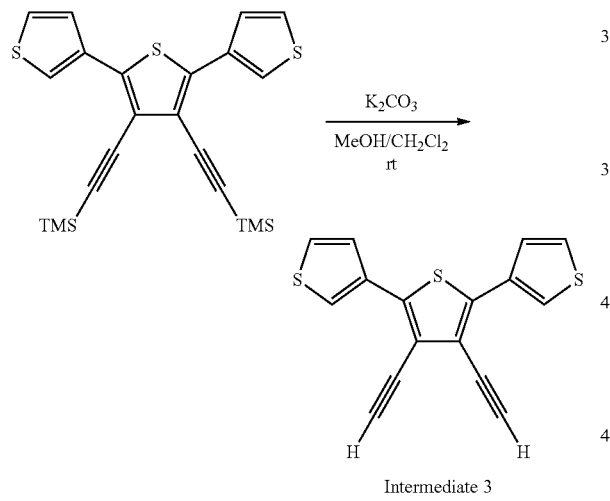

Intermediate 3

38.0 g (86.2 mmol) of Intermediate 2 was dissolved in 345 ml of methylene chloride and 172 ml of methanol (MeOH), 4.77 g (34.5 mmol) of potassium carbonate was added, and stirring was performed at room temperature (rt, 25° C.). After the reaction was completed, concentration was performed by using an evaporator, 300 ml of methylene chloride was added, the reaction liquid passed through silica gel and celite and was eluted with methylene chloride, and concentration was performed by using an evaporator. The crude product was purified by column chromatography (hexane:toluene=9:1) and further divided, and re-crystallization was performed with methylene chloride/methanol, so as to obtain 23.9 g (80.7 mmol, yield: 94%) of an object (Intermediate 3) which was a yellow solid.

$^1$H-NMR (CDCl$_3$, 400 MHz) δ=3.49 (2H, s), 7.38 (2H, dd, J=3.2 Hz, 4.8 Hz), 7.58 (2H, dd, J=1.0 Hz, 5.4 Hz), 7.96 (2H, dd, J=1.0 Hz, 3.0 Hz).

<Synthesis of Intermediate 4>

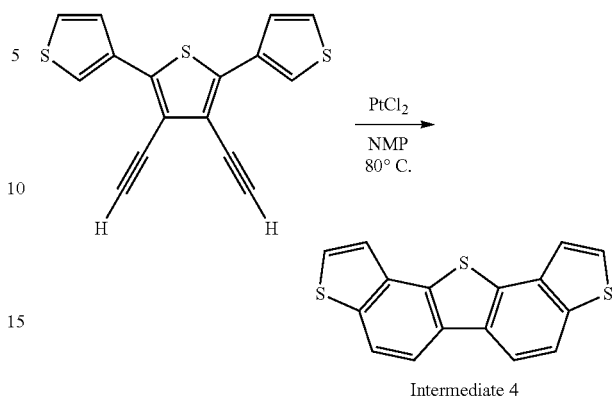

Intermediate 4

23.5 g (79.3 mmol) of Intermediate 3 and 3.17 g (11.9 mmol) of platinum chloride were added to 400 ml of N-methyl pyrrolidone, and heated to 80° C. for nine hours. After the reaction was completed, methanol was excessively added, precipitate was precipitated, filtration was performed, heating and dissolving were performed with o-dichlorobenzene, the resultant passed through silica gel and celite to perform elution, concentration was performed by using an evaporator, and re-crystallization was performed with toluene, so as to obtain 10.4 g (35.1 mmol, yield: 44%) of an object (Intermediate 4) which was a white solid.

$^1$H-NMR (CDCl$_3$, 400 MHz) δ=7.64 (4H, m), 7.97 (2H, d, J=8.0 Hz), 8.16 (2H, d, J=8.8 Hz).

<Synthesis of Intermediate 5>

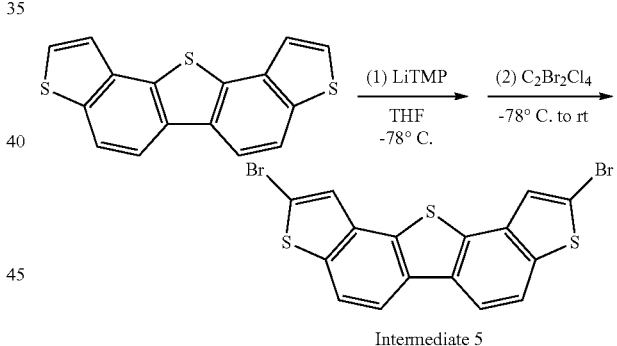

Intermediate 5

26 ml of tetrahydrofuran was added to 4.46 ml (26.2 mmol) of tetramethylpiperidine (TMP), stirring was performed at −78° C., 15.7 ml (25.1 mmol) of n-butyllithium (1.6 M hexane solution) was added, the temperature was raised to 0° C., and stirring was performed for one hour, so as to prepare a lithium reagent I (LiTMP).

114 ml of tetrahydrofuran was heated to 3.00 g (11.4 mmol) of Intermediate 4, stirring was performed at −78° C., the lithium reagent I was dropwise added at −78° C. for using a cannula, and stirring was performed for two hours, so as to prepare a lithium reagent II. 14.8 g (45.6 mmol) of dibromotetrachloroethane was dissolved in 45 ml of tetrahydrofuran in another flask, the solution was prepared, and cooling was performed at −78° C. The lithium reagent II was dropwise added to this solution by using a cannula. Thereafter, the reaction liquid was gradually heated to room temperature, and stirring was performed at 15 hours. Thereafter, excessive methanol was added, and precipitate was filtrated. The filtrated solid was re-crystallized with o-dichlorobenzene, so as to obtain 3.62 g (7.97 mmol, yield: 70%) of an object (Intermediate 5) which was a yellow solid.

$^1$H-NMR (tetrachloroethane-$d_2$, 400 MHz) δ=7.60 (2H, s), 7.81 (2H, d, J=8.0 Hz), 8.09 (2H, d, J=8.0 Hz).

<Synthesis of Example Compound 1>

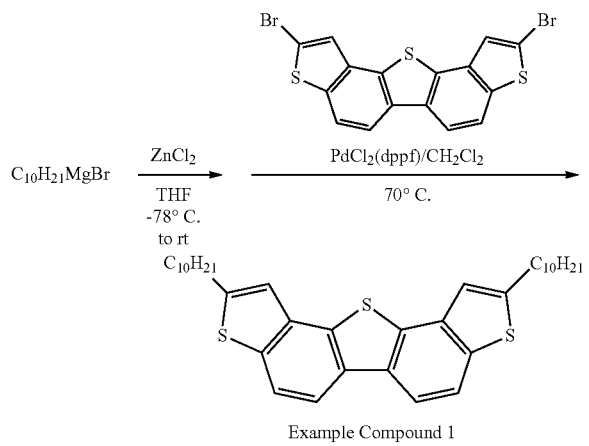

Example Compound 1

1.8 ml (1.8 mmol) of decyl magnesium bromide (1.0 M diethyl ether solution) was cooled to 0° C., 1.8 ml of zinc chloride (II) (1.0 M tetrahydrofuran solution) individually prepared was dropwise added, and an organic zinc reagent was prepared. 200 mg (0.44 mmol) of Intermediate 5 and 18 mg (0.022 mmol) of a dichlorodiphenylphosphinoferrocene palladium methylene chloride adduct (PdCl$_2$ (dppf)/CH$_2$Cl$_2$) were added to this organic zinc reagent, 4.4 ml of tetrahydrofuran was further added, and heating was performed to 70° C. After the reaction was completed, methanol was added, precipitate was precipitated, filtration was performed. The crude product was purified by column chromatography (hexane:toluene=95:5), and re-crystallization was performed with toluene/ethanol, so as to obtain 217 mg (0.376 mmol, yield: 85%) of an object (Example Compound 1) which was a white solid. The structure of obtained Example Compound 1 was identified by $^1$H-NMR.

$^1$H-NMR (tetrachloroethane-$d_2$, 400 MHz) δ=0.82 (6H, t, J=6.8 Hz), 1.22-1.41 (28H, m), 1.75 (4H, quin, J=7.4 Hz), 2.94 (4H, t, J=7.6 Hz), 7.21 (2H, s), 7.81 (2H, d, J=8.8 Hz), 8.00 (2H, d, J=8.4 Hz).

<Synthesis of Example Compound 2>

In the same manner as in the synthesis of Example Compound 1 except for using hexyl magnesium bromide, Example Compound 2 which was a white compound was obtained.

$^1$H-NMR (Tetrachloroethane-$d_2$, 400 MHz) δ=0.85 (6H, t, J=7.0 Hz), 1.27-1.43 (12H, m), 1.75 (4H, quin, J=7.4 Hz), 2.94 (4H, t, J=7.4 Hz), 7.21 (2H, s), 7.80 (2H, d, J=8.4 Hz), 8.00 (2H, d, J=8.8 Hz).

Example Compound 2

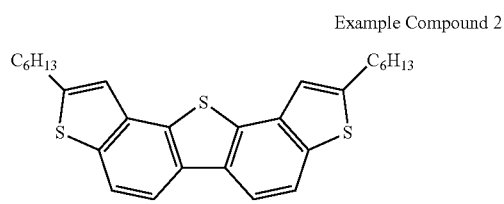

<Synthesis of Comparative Compound 1>

Comparative Compound 1 in a structure below was synthesized according to a synthesis method disclosed in WO2014/057684A.

Comparative Compound 1

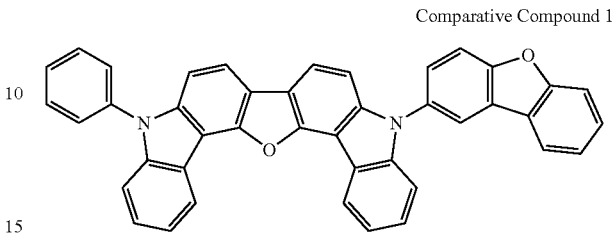

<Synthesis of Comparative Compounds 2 and 3>

Comparative Compounds 2 and 3 were synthesized with reference to JP2013-235903A and US2012/0168734A. With respect to Comparative Compound 2, as a result of gel permeation chromatography (GPC) measurement, a weight-average molecular weight Mw was 40,000.

Comparative Compound 2

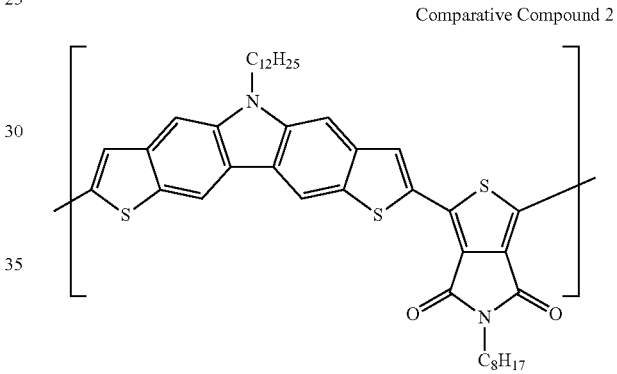

Comparative Compound 3

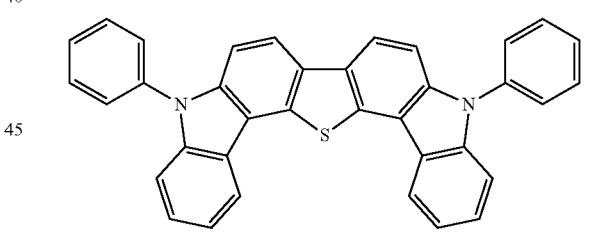

<Manufacturing and Evaluating Element>

It was checked that a material used in the manufacturing of the element has purity (absorption intensity area ratio of 254 nm) of 99.0% or greater by high performance liquid chromatography.

<Forming of Semiconductor Active Layer (Organic Semiconductor Layer) with Compound Singly>

0.1 mass % solution of any one of Example Compounds 1 and 2 and Comparative Compounds 1 to 3 was prepared by using anisole as a solvent, and the resultant heated to 50° C. was set as a coating solution for an organic semiconductor device.

In Examples 1 and 2 and Comparative Examples 1 to 3, an organic semiconductor film was formed by the method disclosed in FIG. 3. Details thereof are provided below.

200 nm of a SiO$_2$ thermal oxide film was formed on the surface of an n-type silicon substrate (thickness of 0.4 mm), a 25 mm×25 mm substrate was used as the substrate A (the substrate 212 of FIG. 3). The surface of the thermal oxide film of the substrate A was cleaned by ultraviolet (UV)-ozone cleaning, and a β-phenethyltrimethoxysilane treatment was performed.

The member B was arranged on the β-phenethyltrimethoxysilane treatment surface of the substrate A in the center of the substrate A as illustrated in FIG. 3(A) so as to be in a state in which the substrate A and the member B (the member 214 of FIG. 3) are in contact with each other. The member B was made of glass, a member of 10 mm longitudinally×2 mm horizontally×5 mm in height was used, a left-right direction (X axis direction) of FIG. 3(A) was a horizontal direction of the member B, an upper-lower direction (Z axis direction) of FIG. 3(A) is a height direction of the member B, and an upper-lower direction (Y axis direction) of FIG. 3(B2) is a machine direction of the member B.

The substrate was heated to 50° C., one drop (about 0.05 ml) of a coating liquid prepared by the method described above was dripped to this from the side portion of the member B so as to come into contact with both of the substrate A and the member B as illustrated in FIG. 3(A), by using a pipette. As illustrated in FIGS. 3(B1) and 3(B2), the coating liquid was dropwise added to a portion of the in-plane of the substrate A. A concave meniscus was formed in an interface with the member B.

As illustrated in FIG. 3(C), while a state in which the substrate A and the member B were in contact with each other was maintained, in a state in which a positional relationship between the substrate A and the member B was caused to be still, a coating liquid was naturally dried. Thereafter, drying was performed at 60° C. for eight hours under reduced pressure of $10^{-3}$ MPa, and crystals of any one of Example Compounds 1 and 2 and Comparative Compounds 1 to 3 were precipitated, so as to form an organic semiconductor film. It was checked that whether the crystals were precipitated by observation with a polarizing microscope.

The obtained organic semiconductor film was used as a semiconductor active layer, a mask was further attached, and 1 nm of F4-TCNQ and 40 nm of a gold electrode were respectively vapor deposited as a charge injection acceptor, so as to obtain an organic thin film transistor element for measuring FET characteristics. The obtained organic thin film transistor elements were set as organic thin film transistor elements of Examples 1 and 2, and Comparative Examples 1 to 3 (hereinafter, respectively referred to as Elements 1 and 2 and Comparative Elements 1 to 3).

<Evaluation>

The field effect transistor (FET) characteristics of the organic thin film transistor elements of Examples 1 and 2 and Comparative Example 1 to 3 were evaluated under the normal pressure and the normal atmosphere by employing a semiconductor parameter analyzer (manufactured by Agilent, 4156C) to which a semi automatic prober (manufactured by Vector Semiconductor Co., Ltd., AX-2000) was connected.

The obtained results are provided in Table 36.

(a) Carrier mobility

A voltage of −80 V was applied between source electrodes and drain electrodes of respective organic thin film transistor elements (organic TFT element), a gate voltage was changed in the range of 20 V to −100 V, carrier mobility μ was calculated by using Equation $I_d=(w/2L)\mu C_i(V_g-V_{th})^2$ (in the equation, L represents a gate length, W represents a gate width, $C_i$ represents capacity per unit area of an insulating layer, $V_g$ represents a gate voltage, and $V_{th}$ represents a threshold voltage) representing a drain current $I_d$, carrier mobility of $10^{-1}$ cm$^2$/Vs or greater was evaluated as A, carrier mobility of $10^{-3}$ to $10^{-2}$ cm$^2$/Vs was evaluated as B, and carrier mobility of $10^{-3}$ cm$^2$/Vs or less was evaluated as C.

TABLE 36

| Element number | Organic semiconductor material | Carrier mobility (cm$^2$/Vs) | Remark |
|---|---|---|---|
| Element 1 | Example Compound 1 | A | Present Invention |
| Element 2 | Example Compound 2 | A | Present Invention |
| Comparative Element 1 | Comparative Compound 1 | B | Comparative Example |
| Comparative Element 2 | Comparative Compound 2 | C | Comparative Example |
| Comparative Element 3 | Comparative Compound 3 | B | Comparative Example |

In Table 36, it was found that the organic thin film transistor elements of respective examples in which the compound according to the present invention was used had high carrier mobility and were preferably used as an organic semiconductor material.

Meanwhile, it was found that the organic thin film transistor elements in which Comparative Compounds 1 to 3 which were out of the range of Formula 1 were used as organic semiconductor materials in a semiconductor active layer had low carrier mobility.

Examples 3 and 4 and Comparative Examples 4 to 6

In Examples 3 and 4 and Comparative Examples 4 to 6, bottom gate-bottom contact type organic thin film transistor elements were manufactured. Details thereof are provided as below.

A 0.1 mass % anisole solution of Example Compound 1 was heated to 100° C. and cast to a substrate for measuring FET characteristics heated to 90° C. under the nitrogen atmosphere so as to obtain a non-luminescent organic thin film transistor element 3. As the substrate for measuring FET characteristics, a silicon substrate in a bottom gate-bottom contact structure including chromium/gold (gate width W=100 mm, gate length L=100 μm) arranged in a comb-shape as source and drain electrodes and SiO$_2$ (film thickness: 200 nm) as an insulating film was used. The obtained element 3 was an organic thin film transistor element of Example 3.

Element 4 and Comparative Element 4 to 6 were manufactured in the same manner as in Element 3, except for using any one of Example Compound 2 and Comparative Compounds 1 to 3 instead of Example Compound 1. Element 4 obtained was set as an organic thin film transistor element of Example 4, and Comparative Elements 4 to 6 were set as organic thin film transistor elements of Comparative Examples 4 to 6.

<Evaluation>

The FET characteristics of the organic thin film transistor elements of Elements 3 and 4 and Comparative Elements 4 to 6 were evaluated in the same method as Example 1. The results thereof are provided in Table 37.

TABLE 37

| Element number | Organic semiconductor material | Carrier mobility (cm²/Vs) | Remark |
|---|---|---|---|
| Element 3 | Example Compound 1 | B | Present Invention |
| Element 4 | Example Compound 2 | B | Present Invention |
| Comparative Element 4 | Comparative Compound 1 | C | Comparative Example |
| Comparative Element 5 | Comparative Compound 2 | C | Comparative Example |
| Comparative Element 6 | Comparative Compound 3 | C | Comparative Example |

Examples 5 and 6 and Comparative Examples 7 to 9

<Manufacturing of Bottom Gate-Bottom Contact Type Element Using Polymer Binder>

A bottom gate-bottom contact type element 5 was manufactured in the same manner as in Example 3 except for using a material (a material 1') containing Example Compound 1 and poly α-methylstyrene instead of Example Compound 1 in the example in a mass ratio of 1:1. Element 5 obtained was set as an organic thin film transistor element of in the example.

In the manufacturing of Element 5, Element 6 and Comparative Elements 7 to 9 were manufactured in the same manner as in Element 5, except for using any one of Example Compound 2 and Comparative Compounds 1 to 3, instead of Example Compound 1. Element 6 obtained was set as the organic thin film transistor element of Example 6 and Comparative Elements 7 to 9 obtained were set as organic thin film transistor elements of Comparative Example 7 to 9.

<Evaluation>

FET characteristics of the organic thin film transistor elements of Elements 5 and 6 and Comparative Elements 7 to 9 were evaluated in the same method as Example 1. The results are provided in Table 38.

TABLE 38

| Element number | Organic semiconductor material | Carrier mobility (cm²/Vs) | Remark |
|---|---|---|---|
| Element 5 | Example Compound 1 | B | Present Invention |
| Element 6 | Example Compound 2 | B | Present Invention |
| Comparative Element 7 | Comparative Compound 1 | C | Comparative Example |
| Comparative Element 8 | Comparative Compound 2 | C | Comparative Example |
| Comparative Element 9 | Comparative Compound 3 | C | Comparative Example |

According to Tables 37 and 38, it was found that the organic thin film transistor elements of the respective examples using the compound according to the present invention have high carrier mobility even in a case of bottom gate-bottom contact type elements and in a case where polymer binders were used, and were preferably used as an organic semiconductor material.

Meanwhile, it was found that an organic thin film transistor element in which any one of Comparative Compound 1 to 3 out of the range of Formula 1 was used in a semiconductor active layer as an organic semiconductor material has low carrier mobility.

EXPLANATION OF REFERENCES

11: substrate
12: gate electrode
13: insulator layer
14: semiconductor active layer (organic layer, organic semiconductor layer)
15a, 15b: source/drain electrode
31: substrate
32: gate electrode
33: insulator layer
34a, 34b: source/drain electrode
35: semiconductor active layer (organic layer, organic semiconductor layer)
210: coating liquid
212: substrate
214: member
216: pipette

What is claimed is:
1. An organic semiconductor element comprising:
a semiconductor active layer including a compound that is represented by Formula 1 and has a molecular weight of 3,000 or less,

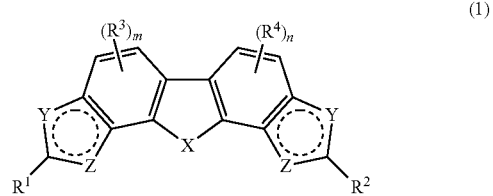

wherein, in Formula 1:
X represents an oxygen atom, a sulfur atom, a selenium atom, or a tellurium atom,
Y and Z each independently represent $CR^5$, an oxygen atom, a sulfur atom, a selenium atom, a nitrogen atom, or $NR^6$, two Y's may be identical to or different from each other, and two Z's may be identical to or different from each other, all rings including Y and Z are aromatic hetero rings, the aromatic hetero rings including $R^1$ and $R^2$ and Y and Z may be bonded to each other via the following group A of divalent linking groups, $R^3$, $R^4$, and a benzene ring may be bonded to each other via the following group A of divalent linking groups, the group A of divalent linking groups represents any one divalent linking group of —O—, —S—, —$NR^7$—, —CO—, —SO—, and —$SO_2$— or a divalent linking group obtained by bonding two or more of these divalent linking groups, m and n each independently represent an integer of 0 to 2, $R^1$, $R^2$, $R^5$, $R^6$, and $R^7$ each independently represent a hydrogen atom, an alkyl group, an alkenyl group, an alkynyl group, an aryl group, or a heteroaryl group, $R^3$ and $R^4$ each independently represent an alkyl group, an alkenyl group, an alkynyl group, an aryl group, or a heteroaryl group, in a case where there are two $R^3$'s, the two $R^3$'s may be identical to or different from each other, and in a case where there are two $R^4$'s, the two $R^4$'s may be identical to or different from each other, each Z is a nitrogen atom, when each Y is independently an oxygen atom, a sulfur atom, a selenium atom, or $NR^6$, and each Z is an oxygen atom, a selenium atom, a nitrogen atom, or $NR^6$, when each Y is —CH—.

2. The organic semiconductor element according to claim 1, wherein the aromatic hetero rings including Y and Z are each independently a thiophene ring, a furan ring, a pyrrole ring, a selenophene ring, a thiazole ring, or an oxazole ring.

3. The organic semiconductor element according to claim 1, wherein the numbers of carbon atoms of $R^1$ and $R^2$ are each independently 1 to 30.

4. The organic semiconductor element according to claim 1, wherein both of m and n are 0.

5. The organic semiconductor element according to claim 1, wherein $R^1$ and $R^2$ each independently represent an alkyl group having 1 to 20 carbon atoms, an aryl group having 6 to 20 carbon atoms, and an heteroaryl group having 3 to 20 carbon atoms.

6. The organic semiconductor element according to claim 1, wherein $R^1$ and $R^2$ are identical to each other, $R^3$ and $R^4$ are identical to each other, and m and n are identical to each other.

7. The organic semiconductor element according to claim 1, wherein the compound that is represented by Formula 1 and has a molecular weight of 3,000 or less is a compound that is represented by Formula 2 or 3 and has a molecular weight of 3,000 or less,

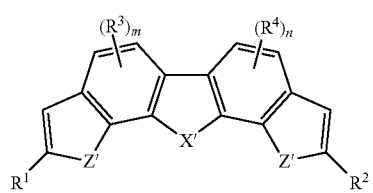

(2)

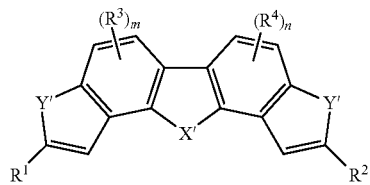

(3)

in Formulae 2 and 3, each X' independently represents an oxygen atom, a sulfur atom, or a selenium atom, Y' and Z' each independently represent $NR^8$, an oxygen atom, a sulfur atom, or a selenium atom, $R^1$ and $R^2$ and aromatic hetero rings including Y' or Z' may be bonded to each other via the following group A of divalent linking groups, $R^3$, $R^4$, and a benzene ring may be bonded to each other via the following group A of divalent linking groups, the group A of divalent linking groups represents any one divalent linking group of —O—, —S—, —$NR^9$—, —CO—, —SO—, and —$SO_2$— or a divalent linking group obtained by bonding two or more of these divalent linking groups, m and n each independently represent an integer of 0 to 2, $R^1$, $R^2$, $R^8$, and $R^9$ each independently represent a hydrogen atom, an alkyl group, an alkenyl group, an alkynyl group, an aryl group, or a heteroaryl group, and $R^3$ and $R^4$ each independently represent an alkyl group, an alkenyl group, an alkynyl group, an aryl group, or a heteroaryl group, in a case where there are two $R^3$'s, the two $R^3$'s may be identical to or different from each other, and in a case where there are two $R^4$'s, the two $R^4$'s may be identical to or different from each other.

8. The organic semiconductor element according to claim 1, wherein the compound that is represented by Formula 1 and has a molecular weight of 3,000 or less is a compound that is represented by Formula 4 or 5 and has a molecular weight of is 3,000 or less,

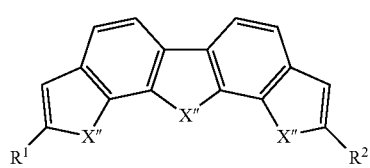

(4)

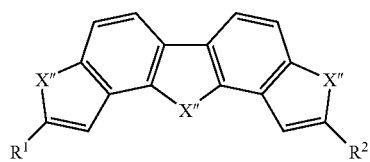

(5)

in Formulae 4 and 5, each X" independently represents an oxygen atom, a sulfur atom, or a selenium atom, $R^1$ and $R^2$ and aromatic hetero rings including X" may be bonded to each other via the following group A of divalent linking groups, the group A of divalent linking groups represents any one divalent linking group of —O—, —S—, —$NR^{10}$—, —CO—, —SO—, and —SO$_2$— or a divalent linking group obtained by bonding two or more of these divalent linking groups, and R$^1$, R$^2$, and R$^{10}$ each independently represent a hydrogen atom, an alkyl group, an alkenyl group, an alkynyl group, an aryl group, or a heteroaryl group.

9. The organic semiconductor element according to claim 1,
wherein R$^1$ and R$^2$ are each independently a group at least having an alkyl group, an alkenyl group, or an alkynyl group.

10. The organic semiconductor element according to claim 1,
wherein R$^1$ and R$^2$ are each independently a linear alkyl group.

11. The organic semiconductor element according to claim 1,
wherein each Y independently represents CR$^5$ or a nitrogen atom, and each Z independently represents an oxygen atom, a sulfur atom, a selenium atom, or NR$^6$.

12. A composition for forming an organic semiconductor film, comprising:
a compound that is represented by Formula 1 and has a molecular weight of 3,000 or less, and
a solvent,

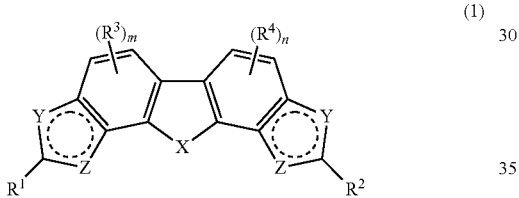

wherein, in Formula 1:
X represents an oxygen atom, a sulfur atom, a selenium atom, or a tellurium atom,
Y and Z each independently represent CR$^5$, an oxygen atom, a sulfur atom, a selenium atom, a nitrogen atom, or NR$^6$, two Y's may be identical to or different from each other, and two Z's may be identical to or different from each other,
all rings including Y and Z are aromatic hetero rings,
the aromatic hetero rings including R$^1$ and R$^2$ and Y and Z may be bonded to each other via the following group A of divalent linking groups,
R$^3$, R$^4$, and a benzene ring may be bonded to each other via the following group A of divalent linking groups,
the group A of divalent linking groups represents any one divalent linking group of —O—, —S—, —NR$^1$—, —CO—, —SO—, and —SO$_2$— or a divalent linking group obtained by bonding two or more of these divalent linking groups,
m and n each independently represent an integer of 0 to 2,
R$^1$, R$^2$, R$^5$, R$^6$, and R$^7$ each independently represent a hydrogen atom, an alkyl group, an alkenyl group, an alkynyl group, an aryl group, or a heteroaryl group,
R$^3$ and R$^4$ each independently represent an alkyl group, an alkenyl group, an alkynyl group, an aryl group, or a heteroaryl group, in a case where there are two R$^3$'s, the two R$^3$'s may be identical to or different from each other, and in a case where there are two R$^4$'s, the two R$^4$'s may be identical to or different from each other,
each Z is a nitrogen atom, when each Y is independently an oxygen atom, a sulfur atom, a selenium atom, or NR$^6$, and
each Z is an oxygen atom, a selenium atom, a nitrogen atom, or NR$^6$, when each Y is —CH—.

13. A method of manufacturing an organic semiconductor element, comprising:
a step of manufacturing a semiconductor active layer by coating a substrate with the composition for forming an organic semiconductor film according to claim 12 and drying the composition.

14. A method of manufacturing an organic semiconductor film, comprising:
a step of dropwise adding the composition for forming an organic semiconductor film according to claim 12 to a portion of an in-plane of a substrate A so as to be in contact with both of the substrate A and a member B that is not in contact with the substrate A, while maintaining a state in which a distance between the substrate A and the member B is maintained to be constant or a state in which the substrate A and the member B are brought into contact with each other; and
a step of precipitating crystals of the compound by drying the dropwise added composition to form a semiconductor active layer.

* * * * *